(12) United States Patent
Leabman

(10) Patent No.: US 11,844,596 B2
(45) Date of Patent: Dec. 19, 2023

(54) METHODS AND SYSTEMS FOR MONITORING BLOOD PRESSURE IN A PERSON USING RADIO WAVES

(71) Applicant: MOVANO INC., San Ramon, CA (US)

(72) Inventor: Michael A. Leabman, San Ramon, CA (US)

(73) Assignee: Movano Inc., Pleasanton, CA (US)

( * ) Notice: Subject to any disclaimer, the term of this patent is extended or adjusted under 35 U.S.C. 154(b) by 323 days.

(21) Appl. No.: 17/071,967

(22) Filed: Oct. 15, 2020

(65) Prior Publication Data

US 2021/0038091 A1    Feb. 11, 2021

Related U.S. Application Data

(63) Continuation of application No. 16/682,899, filed on Nov. 13, 2019.

(Continued)

(51) Int. Cl.
*A61B 5/05* (2021.01)
*H01Q 21/06* (2006.01)
(Continued)

(52) U.S. Cl.
CPC ............ *A61B 5/0245* (2013.01); *A61B 5/021* (2013.01); *A61B 5/022* (2013.01); *A61B 5/02141* (2013.01); *A61B 5/02438* (2013.01); *A61B 5/02444* (2013.01); *A61B 5/05* (2013.01); *A61B 5/0507* (2013.01); *A61B 5/14532* (2013.01); *A61B 5/489* (2013.01); *A61B 5/681* (2013.01); *A61B 5/6898* (2013.01); *A61B 5/725* (2013.01);
(Continued)

(58) Field of Classification Search
CPC ... A61B 5/0245; A61B 5/021; A61B 5/02141; A61B 5/022; A61B 5/02438; A61B 5/02444; A61B 5/05; A61B 5/0507; A61B 5/14532; A61B 5/489; A61B 5/681; A61B 5/6898; A61B 5/725; A61B 5/7257; A61B 5/7267; A61B 5/742; A61B 5/02108; A61B 2562/0228; G01S 7/025; G01S 13/53; G01S 13/87; G01S 13/88; G01S 7/028; G06F 1/163; G06N 20/00; H01Q 1/273; H01Q 21/061; H01Q 21/065
See application file for complete search history.

(56) References Cited

U.S. PATENT DOCUMENTS

| | | |
|---|---|---|
| 2011/0221519 A1 | 9/2011 | Katoh et al. |
| 2013/0297223 A1 | 11/2013 | Fischer |

(Continued)

*Primary Examiner* — Matthew Kremer
*Assistant Examiner* — Kyle W. Kretzer
(74) *Attorney, Agent, or Firm* — LOZA & LOZA, LLP

(57) ABSTRACT

Methods and systems for monitoring blood pressure in a person are disclosed. A method for monitoring a blood pressure in a person involves transmitting millimeter range radio waves over a three-dimensional (3D) space below the skin surface of a person, receiving radio waves on multiple receive antennas, the received radio waves including a reflected portion of the transmitted radio waves that is reflected by blood in a blood vessel in the 3D space, isolating a signal that corresponds to the portion of the transmitted radio waves that is reflected by blood in the blood vessel in response to receiving the radio waves on the multiple receive antennas, and outputting a signal that corresponds to a blood pressure level in the person in response to the isolated signal.

19 Claims, 39 Drawing Sheets

Related U.S. Application Data

(60) Provisional application No. 62/894,741, filed on Aug. 31, 2019, provisional application No. 62/781,523, filed on Dec. 18, 2018.

(51) Int. Cl.

| | | |
|---|---|---|
| *A61B 5/00* | (2006.01) | |
| *A61B 5/021* | (2006.01) | |
| *A61B 5/024* | (2006.01) | |
| *G01S 13/53* | (2006.01) | |
| *A61B 5/0507* | (2021.01) | |
| *H01Q 1/22* | (2006.01) | |
| *A61B 5/0245* | (2006.01) | |
| *A61B 5/145* | (2006.01) | |
| *H01Q 1/27* | (2006.01) | |
| *G01S 7/02* | (2006.01) | |
| *G01S 13/88* | (2006.01) | |
| *G06N 20/00* | (2019.01) | |
| *A61B 5/022* | (2006.01) | |
| *G01S 13/87* | (2006.01) | |
| *G06F 1/16* | (2006.01) | |

(52) U.S. Cl.
CPC .......... *A61B 5/7257* (2013.01); *A61B 5/7267* (2013.01); *A61B 5/742* (2013.01); *G01S 7/025* (2013.01); *G01S 13/53* (2013.01); *G01S 13/87* (2013.01); *G01S 13/88* (2013.01); *G06F 1/163* (2013.01); *G06N 20/00* (2019.01); *H01Q 1/2283* (2013.01); *H01Q 1/273* (2013.01); *H01Q 21/061* (2013.01); *A61B 5/02108* (2013.01); *A61B 2562/0228* (2013.01); *G01S 7/028* (2021.05); *H01Q 21/065* (2013.01)

(56) References Cited

U.S. PATENT DOCUMENTS

| | | | |
|---|---|---|---|
| 2014/0134959 | A1 | 5/2014 | Tasic et al. |
| 2016/0228010 | A1* | 8/2016 | Kim ................ A61B 5/021 |
| 2016/0345845 | A1* | 12/2016 | Ravid ............. A61B 5/0507 |
| 2017/0065184 | A1* | 3/2017 | Barak ............. A61B 5/02438 |
| 2017/0238835 | A1* | 8/2017 | Melamed ........... A61B 5/4312 |
| 2017/0303858 | A1* | 10/2017 | Barak ............. A61B 5/02125 |
| 2019/0008422 | A1* | 1/2019 | Leath ............. A61B 5/6898 |
| 2019/0216393 | A1* | 7/2019 | Baheti ............ G01S 7/415 |
| 2019/0282106 | A1* | 9/2019 | Shay .............. A61B 5/681 |
| 2020/0022607 | A1* | 1/2020 | Pratt ............. A61B 5/6891 |
| 2020/0187813 | A1* | 6/2020 | Leabman .......... G01S 13/0209 |

\* cited by examiner

IMPULSE

CHIRP

STEPPED

| | |
|---|---|
| Time (absolute) | variable (controlled) |
| TX/RX frequency | variable (controlled) |
| TX1 – state (active/inactive (e.g., PA on/off)) | variable (controlled) |
| TX2 – state (active/inactive (e.g., PA on/off)) | variable (controlled) |
| RX1 – state (active/inactive) | variable (controlled) |
| RX1 – detected amplitude | variable (detected) |
| RX1 – detected phase | variable (detected) |
| RX2 – state (active/inactive) | variable (controlled) |
| RX2 – detected amplitude | variable (detected) |
| RX2 – detected phase | variable (detected) |
| RX3 – state (active/inactive) | variable (controlled) |
| RX3 – detected amplitude | variable (detected) |
| RX3 – detected phase | variable (detected) |
| RX4 – state (active/inactive) | variable (controlled) |
| RX4 – detected amplitude | variable (detected) |
| RX4 – detected phase | variable (detected) |
| TX1 – antenna 2D position | fixed |
| TX1 – antenna orientation (polarization) | fixed |
| TX2 – antenna 2D position | fixed |
| TX2 – antenna orientation (polarization) | fixed |
| RX1 – antenna 2D position | fixed |
| RX1 – antenna orientation (polarization) | fixed |
| RX2 – antenna 2D position | fixed |
| RX2 – antenna orientation (polarization) | fixed |
| RX3 – antenna 2D position | fixed |
| RX3 – antenna orientation (polarization) | fixed |
| RX4 – antenna 2D position | fixed |
| RX4 – antenna orientation (polarization) | fixed |

FIG. 23

| | |
|---|---|
| Time (absolute) | t1 |
| TX/RX frequency | X GHz |
| TX1 – state (active/inactive (e.g., PA on/off)) | active |
| TX2 – state (active/inactive (e.g., PA on/off)) | inactive |
| RX1 – state (active/inactive) | active |
| RX1 – detected amplitude | amp1 |
| RX1 – detected phase | ph1 |
| RX2 – state (active/inactive) | inactive |
| RX2 – detected amplitude | n/a |
| RX2 – detected phase | n/a |
| RX3 – state (active/inactive) | inactive |
| RX3 – detected amplitude | n/a |
| RX3 – detected phase | n/a |
| RX4 – state (active/inactive) | active |
| RX4 – detected amplitude | amp4 |
| RX4 – detected phase | ph4 |
| TX1 – antenna 2D position | left |
| TX1 – antenna orientation (polarization) | vertical |
| TX2 – antenna 2D position | right |
| TX2 – antenna orientation (polarization) | horizontal |
| RX1 – antenna 2D position | upper-left |
| RX1 – antenna orientation (polarization) | vertical |
| RX2 – antenna 2D position | upper-right |
| RX2 – antenna orientation (polarization) | horizontal |
| RX3 – antenna 2D position | lower-left |
| RX3 – antenna orientation (polarization) | horizontal |
| RX4 – antenna 2D position | lower-right |
| RX4 – antenna orientation (polarization) | vertical |

FIG. 24

| Time (absolute) | t1 |
|---|---|
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 26

| Time (absolute) | t1 |
|---|---|
| Known Glucose level | Z mg/dL |
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 29

| | |
|---|---|
| Time (absolute) | t1 |
| Glucose level | Z1 |
| TX/RX frequency | X GHz |
| RX1 – detected amplitude | amp1 |
| RX1 – detected phase | ph1-t1 |
| RX2 – detected amplitude | amp2-t1 |
| RX2 – detected phase | ph2-t1 |
| RX3 – detected amplitude | amp3-t1 |
| RX3 – detected phase | ph3-t1 |
| RX4 – detected amplitude | amp4-t1 |
| RX4 – detected phase | ph4-t1 |

FIG. 30A

| | |
|---|---|
| Time (absolute) | t2 |
| Glucose level | Z2 |
| TX/RX frequency | X GHz + $\Delta f$ |
| RX1 – detected amplitude | amp1-t2 |
| RX1 – detected phase | ph1-t2 |
| RX2 – detected amplitude | amp2-t2 |
| RX2 – detected phase | ph2-t2 |
| RX3 – detected amplitude | amp3-t2 |
| RX3 – detected phase | ph3-t2 |
| RX4 – detected amplitude | amp4-t2 |
| RX4 – detected phase | ph4-t2 |

FIG. 30B

| Time (absolute) | t3 |
|---|---|
| Glucose level | Z3 |
| TX/RX frequency | X GHz + $2\Delta f$ |
| RX1 – detected amplitude | amp1-t3 |
| RX1 – detected phase | ph1-t3 |
| RX2 – detected amplitude | amp2-t3 |
| RX2 – detected phase | ph2-t3 |
| RX3 – detected amplitude | amp3-t3 |
| RX3 – detected phase | ph3-t3 |
| RX4 – detected amplitude | amp4-t3 |
| RX4 – detected phase | ph4-t3 |

FIG. 30C

| Time (absolute) | tn |
|---|---|
| Glucose level | Zn |
| TX/RX frequency | X GHz + $(n-1)\Delta f$ |
| RX1 – detected amplitude | amp1-tn |
| RX1 – detected phase | ph1-tn |
| RX2 – detected amplitude | amp2-tn |
| RX2 – detected phase | ph2-tn |
| RX3 – detected amplitude | amp3-tn |
| RX3 – detected phase | ph3-tn |
| RX4 – detected amplitude | amp4-tn |
| RX4 – detected phase | ph4-tn |

FIG. 30D

METHODS AND SYSTEMS FOR MONITORING BLOOD PRESSURE IN A PERSON USING RADIO WAVES

BACKGROUND

Diabetes is a medical disorder in which a person's blood glucose level, also known as blood sugar level, is elevated over an extended period of time. If left untreated, diabetes can lead to severe medical complications such as cardiovascular disease, kidney disease, stroke, foot ulcers, and eye damage. It has been estimated that the total cost of diabetes in the U.S. in 2017 was $327 billion, American Diabetes Association, "Economic Costs of Diabetes in the U.S. in 2017," published online on Mar. 22, 2018.

Diabetes is typically caused by either the pancreas not producing enough insulin, referred to as "Type 1" diabetes, or because the cells of the person do not properly respond to insulin that is produced, referred to as "Type 2" diabetes. Managing diabetes may involve monitoring a person's blood glucose level and administering insulin when the person's blood glucose level is too high to bring the blood glucose level down to a desired level. A person may need to measure their blood glucose level up to ten times a day depending on many factors, including the severity of the diabetes and the person's medical history. Billions of dollars are spent each year on equipment and supplies used to monitor blood glucose levels.

SUMMARY

A method for monitoring a blood pressure in a person is disclosed. The method involves transmitting millimeter range radio waves over a three-dimensional (3D) space below the skin surface of a person, receiving radio waves on multiple receive antennas, the received radio waves including a reflected portion of the transmitted radio waves that is reflected by blood in a blood vessel in the 3D space, isolating a signal that corresponds to the portion of the transmitted radio waves that is reflected by blood in the blood vessel in response to receiving the radio waves on the multiple receive antennas, and outputting a signal that corresponds to a blood pressure level in the person in response to the isolated signal.

In an embodiment, the transmit frequency is in the range of 122-126 GHz.

In an embodiment, isolating a signal that corresponds to the portion of the transmitted radio waves that is reflected by blood in the blood vessel in response to receiving the radio waves on the multiple receive antennas involves implementing beamforming signal processing to isolate a signal that corresponds to radio waves reflected from blood in the blood vessel.

In an embodiment, isolating a signal that corresponds to the portion of the transmitted radio waves that is reflected by blood in the blood vessel in response to receiving the radio waves on the multiple receive antennas involves using beamforming to focus a receive beam on the blood vessel.

In an embodiment, the transmitting, receiving, isolating, and outputting occurs in a wearable device that is attached to the person.

In an embodiment, the millimeter range radio waves are transmitted from at least one transmit antenna configured for radio waves in a frequency range of 122-126 GHz and the received radio waves are received on multiple receive antennas that are configured for radio waves in a frequency range of 122-126 GHz.

In an embodiment, transmitting millimeter range radio waves over a 3D space below the skin surface of a person involves transmitting from a first transmit antenna and then from a second transmit antenna such that the first transmission does not overlap in time with the second transmission.

In an embodiment, transmitting millimeter range radio waves over a 3D space below the skin surface of a person involves transmitting the millimeter range radio waves in a stepped frequency pattern.

In an embodiment, transmitting millimeter range radio waves over a 3D space below the skin surface of a person involves transmitting the millimeter range radio waves in a stepped frequency pattern in which the frequency is changed by a fixed increment at each step, wherein the transmit frequency is in the range of 122-126 GHz and wherein the fixed increment ranges from 15.625 MHz to 62.5 MHz.

In an embodiment, isolating a signal that corresponds to the portion of the transmitted radio waves that is reflected by blood in the blood vessel in response to receiving the radio waves on the multiple receive antennas involves using Doppler effect processing, including fast Fourier transform (FFT) processing, to isolate signals that correspond to relative movement.

In an embodiment, isolating a signal that corresponds to the portion of the transmitted radio waves that is reflected by blood in the blood vessel in response to receiving the radio waves on the multiple receive antennas involves digitally combining received signals from the multiple receive antennas.

In an embodiment, millimeter range radio waves are transmitted from two transmit antennas and received at four receive antennas.

In an embodiment, radio waves are transmitted at an initial power such that the initial power is diminished by at least one-half at a penetration depth below the skin surface of 6 mm or less.

In an embodiment, the method involves outputting a signal that corresponds to a heart rate in the person in response to the isolated signal.

Another method for monitoring a blood pressure level in a person is disclosed. The method involves transmitting radio waves below the skin surface of a person and across a range of stepped frequencies, receiving radio waves on a two-dimensional array of receive antennas, the received radio waves including a reflected portion of the transmitted radio waves across the range of stepped frequencies that is reflected by blood in a blood vessel below the skin surface of the person, generating data that corresponds to a change in reflectivity of the blood in the blood vessel in response to the reflected portion of the transmitted radio waves that is reflected by the blood in the blood vessel, and determining a value that is indicative of a blood pressure level in the person in response to the generated data.

In an embodiment, the generated data includes amplitude and phase data, and wherein the phase data corresponds to a phase shift in the received radio waves.

In an embodiment, radio waves are transmitted from transmit antennas that have at least two different polarization orientations and wherein radio waves are received on antennas in the two-dimensional array of receive antennas that have polarization orientations that correspond to the transmit antennas.

A system for monitoring a blood pressure level in a person is also disclosed. The system includes at least one transmit antenna configured to transmit millimeter range radio waves over a 3D space below the skin surface of a person, multiple receive antennas configured to receive radio waves, the received radio waves including a reflected portion of the transmitted radio waves that is reflected by blood in a blood vessel in the 3D space, and means for isolating a signal that corresponds to the portion of the transmitted radio waves that is reflected by blood in the blood vessel in response to receiving the radio waves on the multiple receive antennas and outputting a signal that corresponds to a blood pressure level of the person in response to the isolated signal.

In an embodiment, the at least one transmit antenna and the multiple receive antennas are configured for radio waves in a frequency range of 122-126 GHz.

In an embodiment, the system further includes a semiconductor substrate with at least one transmit component and multiple receive components, wherein the at least one transmit component and the at least one transmit antenna comprise at least two transmit components and at least two transmit antennas and wherein the multiple receive components and multiple receive antennas comprises four receive components and four receive antennas.

In an embodiment, the at least two transmit antennas are configured to transmit radio waves at two different polarization orientations and wherein a first set of the at least four receive antennas is configured to receive radio waves at one of the at least two different polarization orientations and a second set of the at least four receive antennas is configured to receive radio waves at a different one of the at least two different polarization orientations.

Other aspects in accordance with the invention will become apparent from the following detailed description, taken in conjunction with the accompanying drawings, illustrated by way of example of the principles of the invention.

BRIEF DESCRIPTION OF THE DRAWINGS

FIG. 23 is a table of parameters related to stepped frequency scanning in a system such as the above-described system.

FIG. 24 is a table of parameters similar to the table of FIG. 23 in which examples are associated with each parameter for a given step in a stepped frequency scanning operation in order to give some context to the table.

FIG. 26 is a table of raw data that is generated during stepped frequency scanning.

FIG. 29 is an example of a table of a raw data record generated during stepped frequency scanning that is used to generate the training data.

FIGS. 30A-30D are tables of at least portions of raw data records that are generated during a learning process that spans the time of t1-tn, where n corresponds to the number of time intervals, T, in the stepped frequency scanning.

Throughout the description, similar reference numbers may be used to identify similar elements.

DETAILED DESCRIPTION

Figure 1A:
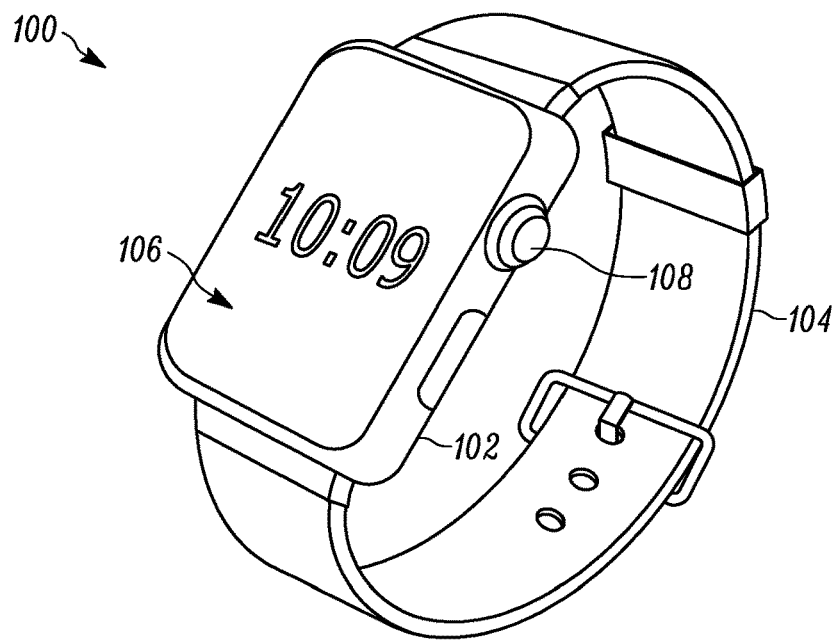
FIGS. 1A and 1B are perspective views of a smartwatch.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

Traditional blood glucose level monitoring is accomplished by pricking a finger to draw blood and measuring the blood glucose level with a blood glucose meter, or "glucometer." Continuous glucose monitoring can be accomplished by applying a continuous glucose monitor (CGM) to an area on the body such as the torso. The continuous glucose monitor utilizes a needle that is continuously embedded through the skin to obtain access to blood. Although blood glucose meters and continuous glucose monitors work well to monitor blood glucose levels, both techniques are invasive in nature in that they require physical penetration of the skin by a sharp object.

Various non-invasive techniques for monitoring blood glucose levels have been explored. Example techniques for monitoring blood glucose levels include techniques based on infrared (IR) spectroscopy, near infrared (NIR) spectroscopy, mid infrared (MIR) spectroscopy, photoacoustic spectroscopy, fluorescence spectroscopy, Raman spectroscopy, optical coherence tomography (OCT), and microwave sensing, Ruochong Zhang et al., "Noninvasive Electromagnetic Wave Sensing of Glucose," Oct. 1, 2018.

In the category of microwave sensing, millimeter range radio waves have been identified as useful for monitoring blood glucose levels. An example of using millimeter range radio waves to monitor blood glucose levels is described by Peter H. Siegel et al., "Millimeter-Wave Non-Invasive Monitoring of Glucose in Anesthetized Rats," 2014 International Conference on Infrared, Millimeter, and Terahertz Waves, Tucson, AZ, Sep. 14-19, 2014. Here, Siegel et al. describes using the Ka band (27-40 GHz) to measure blood glucose levels through the ear of a lab rat.

Another example of using millimeter range radio waves to monitor blood glucose levels is described by George Shaker et al., "Non-Invasive Monitoring of Glucose Level Changes Utilizing a mm-Wave Radar System," International Journal of Mobile Human Computer Interaction, Volume 10, Issue 3, July-September 2018. Here, Shaker et al. utilizes a millimeter range sensing system referred to as "Soli," (see Jaime Lien et. al., "Soli: Ubiquitous Gesture Sensing with Millimeter Wave Radar," ACM Trans. Graph. 35, 4 Article 142, July 2016) to monitor blood glucose levels. Shaker et al. utilizes radio waves in the 57-64 GHz frequency range to monitor blood glucose levels. Although the Soli sensor system includes transmit (TX) and receive (RX) antennas on the same integrated circuit (IC) device (i.e., the same "chip") and thus in the same plane, Shaker et al. concludes that for blood glucose monitoring, a radar sensing system configuration would ideally have its antennas placed on opposite sides of the sample under test to be able to effectively monitor blood glucose levels. When the transmit (TX) and receive (RX) antennas were on the same side of the sample under test, Shaker et al. was not able to find any discernible trend in the magnitude or phase of the sensor signals.

Another example of using millimeter range radio waves to monitor blood glucose levels is described by Shimul Saha et al., "A Glucose Sensing System Based on Transmission Measurements at Millimeter Waves using Micro strip Patch Antennas," Scientific Reports, published online Jul. 31, 2017. Here, Saha et al. notes that millimeter wave spectroscopy in reflection mode has been used for non-invasive glucose sensing through human skin, but concludes that signals from reflection mode detection yield information that is insufficient for tracking the relevant changes in blood glucose levels. Saha et al. investigates radio waves in the range of 20-100 GHz for monitoring blood glucose levels and concludes that an optimal sensing frequency is in the range of 40-80 GHz.

Although blood glucose level monitoring using millimeter range radio waves has been shown to be technically feasible, implementation of practical monitoring methods and systems has yet to be realized. For example, a practical realization of a monitoring system may include a monitoring system that can be integrated into a wearable device, such as a smartwatch.

In accordance with an embodiment of the invention, methods and systems for monitoring the blood glucose level of a person using millimeter range radio waves involve transmitting millimeter range radio waves below the skin surface, receiving a reflected portion of the radio waves on multiple receive antennas, isolating a signal from a particular location in response to the received radio waves, and outputting a signal that corresponds to a blood glucose level in the person in response to the isolated signals. In an embodiment, beamforming is used in the receive process to isolate radio waves that are reflected from a specific location (e.g., onto a specific blood vessel) to provide a high-quality signal that corresponds to blood glucose levels in the specific blood vessel. In another embodiment, Doppler effect processing can be used to isolate radio waves that are reflected from a specific location (e.g., reflected from a specific blood vessel) to provide a high-quality signal that corresponds to blood glucose levels in the specific blood vessel. Analog and/or digital signal processing techniques can be used to implement beamforming and/or Doppler effect processing and digital signal processing of the received signals can be used to dynamically adjust (or "focus") a received beam onto the desired location. In still another embodiment, beamforming and Doppler effect processing can be used together to isolate radio waves that are reflected from a specific location (e.g., reflected from a specific blood vessel) to provide a high-quality signal that corresponds to blood glucose levels in the specific blood vessel.

As described above, Siegal et al., Shaker et al., and Saha et al., utilize radio waves in the range of about 27-80 GHz, commonly around 60 GHz, to monitor blood glucose levels. Saha et al. discloses that a frequency of around 60 GHz is desirable for glucose detection using electromagnetic transmission data and notes that for increasingly higher frequencies, the losses are prohibitively high for the signal-to-noise ratio (SNR) to exceed the noise level of a sensing instrument such as a Vector Network Analyzer (VNA).

In contrast to conventional techniques, it has been discovered that using a higher frequency range, e.g., 122-126 GHz, to monitor blood glucose levels can provide certain benefits that heretofore have not been recognized. For example, transmitting millimeter range radio waves in the frequency range of 122-126 GHz results in a shallower penetration depth within a human body than radio waves in the frequency range around 60 GHz for a similar transmission power. A shallower penetration depth can reduce undesirable reflections (e.g., reflections off of bone and dense tissue such as tendons, ligaments, and muscle), which can reduce the signal processing burden and improve the quality of the desired signal that is generated from the location of a blood vessel.

Additionally, transmitting millimeter range radio waves in the frequency range of 122-126 GHz enables higher resolution sensing than radio waves at around 60 GHz due to the shorter wavelengths, e.g., 2.46-2.38 mm for 122-126 GHz radio waves versus 5 mm for 60 GHz radio waves. Higher resolution sensing allows a receive beam to be focused more precisely (e.g., through beamforming and/or Doppler effect processing) onto a particular blood vessel, such as the basilic vein on the posterior of the wrist, which can also improve the quality of the desired signal.

Additionally, utilizing millimeter range radio waves in the frequency range of 122-126 GHz to monitor blood glucose levels enables the size of the corresponding transmit and receive antennas to be reduced in comparison to techniques that utilize radio waves in the frequency range of 20-80 GHz. For example, the size of antennas can be reduced by a factor of approximately two by using radio waves in the 122-126 GHz frequency range instead of radio waves in the 60 GHz frequency range, which can enable a smaller form factor for the antennas and for the overall sensor system. Additionally, the frequency range of 122-126 GHz is an unlicensed band of the industrial, scientific, and medical (ISM) radio bands as defined by the International Telecommunication Union (ITU) Radio Regulations. Thus, methods and systems for monitoring blood glucose levels that are implemented using a frequency range of 122-126 GHz do not require a license.

Figure 1B:
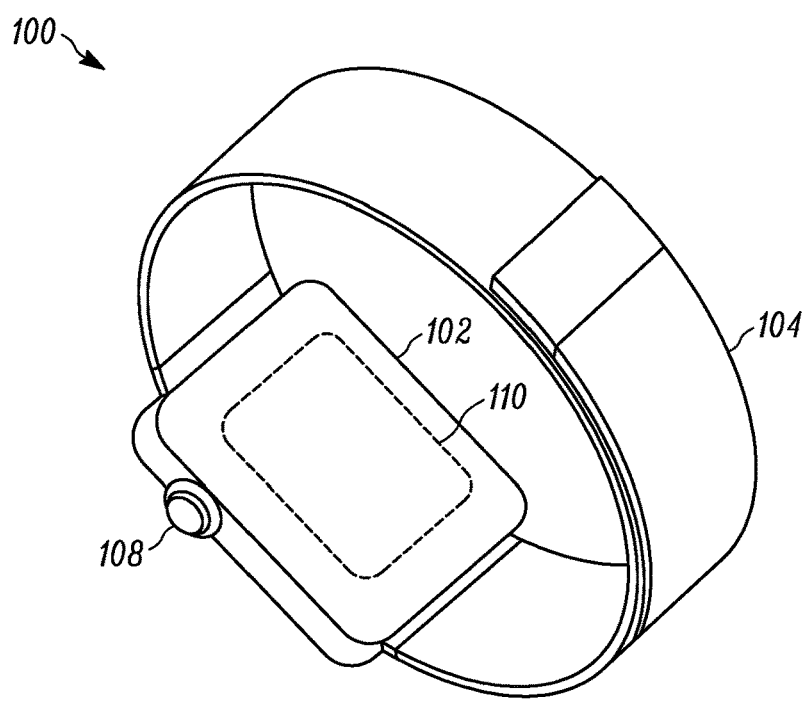

FIGS. 1A and 1B are perspective views of a smartwatch 100, which is a device that provides various computing functionality beyond simply giving the time. Smartwatches are well known in the field. The smartwatch includes a case 102 (also referred to as a "housing") and a strap 104 (e.g., an attachment device) and the strap is typically attached to the case by lugs (not shown). FIG. 1A is a top perspective view of the smartwatch that shows a front face 106 of the case and a crown 108 and FIG. 1B is a back perspective view of the smartwatch that shows a back plate of the case. FIG. 1B also includes a dashed line block 110 that represents a sensor system, such as a sensor system for health monitoring. The sensor system may be partially or fully embedded within the case. In some embodiments, the sensor system may include a sensor integrated circuit (IC) device or IC devices with transmit and/or receive antennas integrated therewith. In some embodiments, the back plate of the case may have openings that allow radio waves to pass more easily to and from smartwatch. In some embodiments, the back plate of the case may have areas of differing materials that create channels through which radio waves can pass more easily. For example, in an embodiment, the back plate of the case may be made primarily of metal with openings in the metal at locations that correspond to sensor antennas that are filled with a material (e.g., plastic or glass) that allows radio waves to pass to and from the smartwatch more easily than through the metal case.

Although a smartwatch is described as one device in which a millimeter range radio wave sensing system can be included, a millimeter range radio wave sensing system can be included in other sensing devices, including various types of wearable devices and/or devices that are not wearable but that are brought close to, or in contact with, the skin of a person only when health monitoring is desired. For example, a millimeter range radio wave sensing system can be incorporated into a smartphone. In an embodiment, a millimeter range radio wave sensing system can be included in a health and fitness tracking device that is worn on the wrist and tracks, among other things, a person's movements. In another embodiment, a millimeter range radio wave sensing system can be incorporated into a device such as dongle or cover (e.g., a protective cover that is placed over a smartphone for protection) that is paired (e.g., via a local data connection such as USB or BLUETOOTH) with a device such as a smartphone or smartwatch to implement health monitoring. For example, a dongle may include many of the components described below with reference to FIG. 6, while the paired device (e.g., the smartphone or smartwatch) includes a digital signal processing capability (e.g., through a Digital Signal Processor (DSP)) and instruction processing capability (e.g., through a Central Processing Unit (CPU)). In another example, a millimeter range sensing system may be incorporated into a device that is attached to the ear. In an embodiment, the sensing system could be attached to the lobe of the ear or have an attachment element that wraps around the ear or wraps around a portion of the ear.

Figure 2A:
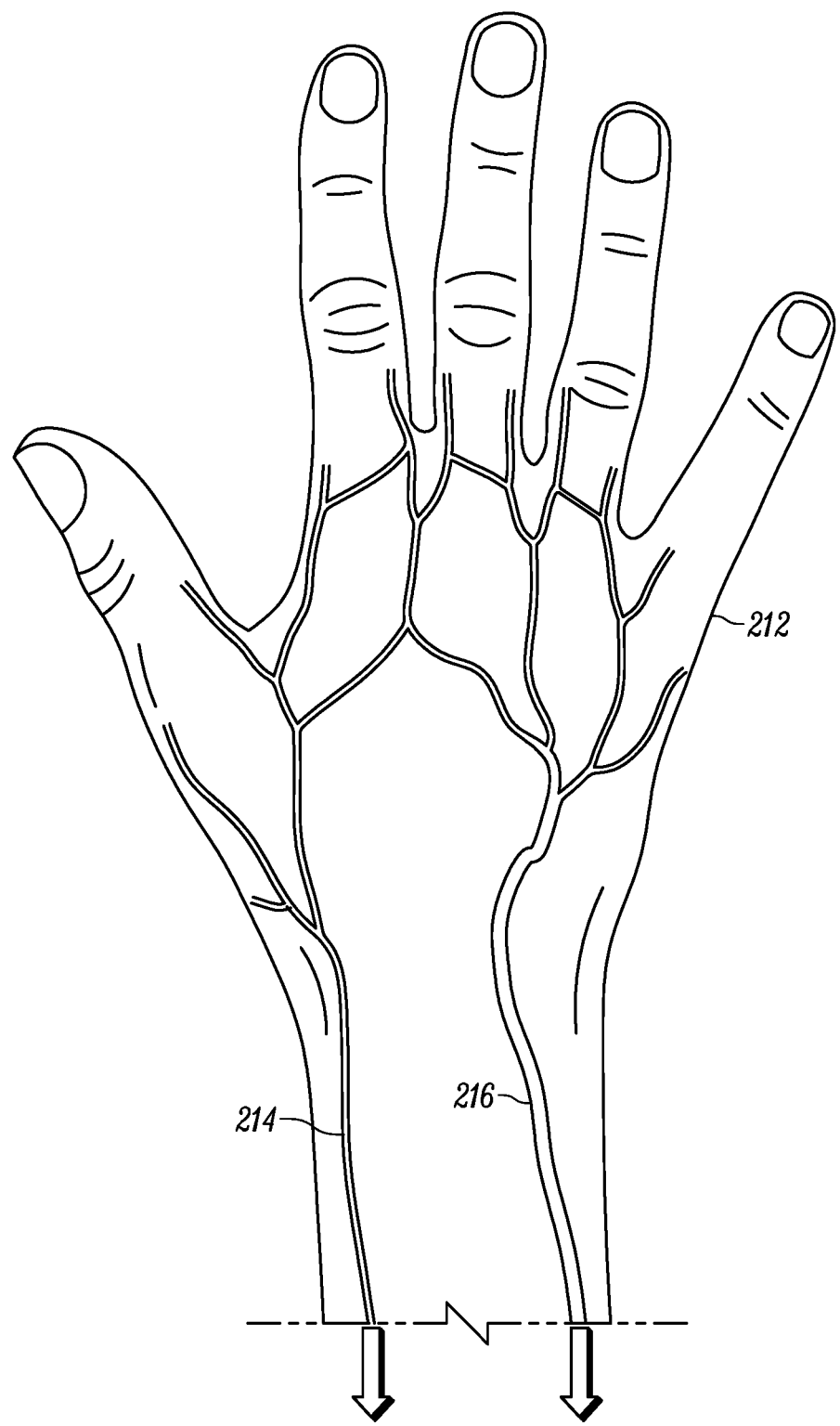
FIG. 2A depicts a posterior view of a right hand with the typical approximate location of the cephalic vein and the basilic vein overlaid/superimposed.
Figure 2B:
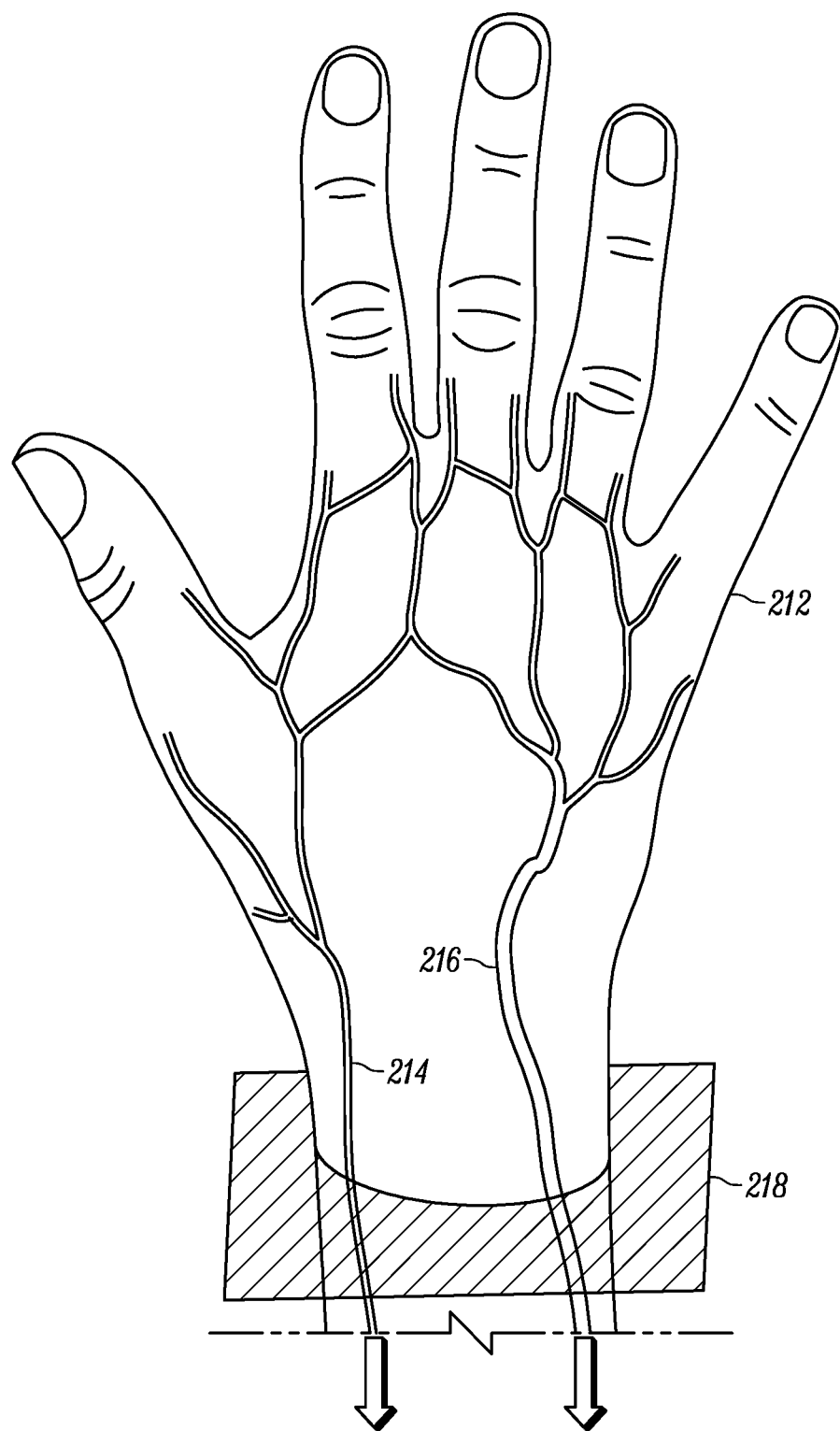
FIG. 2B depicts the location of a cross-section of the wrist from FIG. 2A.
Figure 2C:
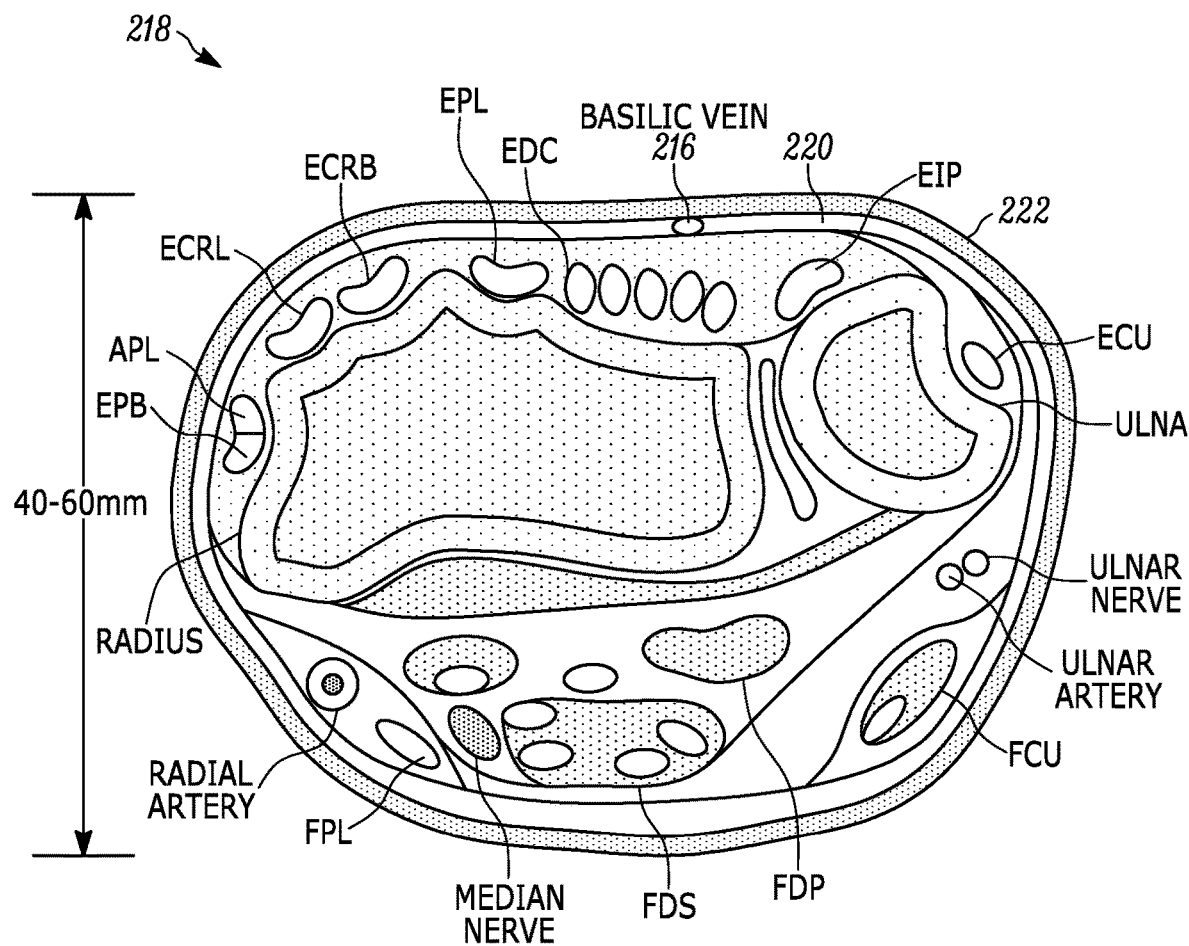
FIG. 2C depicts the cross-section of the wrist from the approximate location shown in FIG. 2B (as viewed in the direction from the elbow to the hand).

Wearable devices such as smartwatches and health and fitness trackers are often worn on the wrist similar to a traditional wristwatch. In order to monitor blood glucose levels using millimeter range radio waves, it has been discovered that the anatomy of the wrist is an important consideration. FIG. 2A depicts a posterior view of a right hand 212 with the typical approximate location of the cephalic vein 214 and the basilic vein 216 overlaid/superimposed. FIG. 2B depicts the location of a cross-section of the wrist 218 from FIG. 2A and FIG. 2C depicts the cross-section of the wrist 218 from the approximate location shown in FIG. 2B (as viewed in the direction from the elbow to the hand). In FIG. 2C, the cross-section is oriented on the page such that the posterior portion of the wrist is on the top and the anterior portion of the wrist is on the bottom. The depth dimension of a wrist is identified on the left side and typically ranges from 40-60 mm (based on a wrist circumference in the range of 140-190 mm). Anatomic features of the wrist shown in FIG. 2C include the abductor pollicis longus (APL), the extensor carpi radialis brevis (ECRB), the extensor carpi radialis longus (ECRL), the extensor carpi ulnaris (ECU), the extensor indicis proprius (EIP), the extensor pollicis brevis (EPB), the extensor pollicis longus (EPL), the flexor carpi ulnaris (FCU), the flexor digitorum superficialis (FDS), the flexor pollicis longus (FPL), the basilic vein 216, the radius, the ulna, the radial artery, the median nerve, the ulnar artery, and the ulnar nerve. FIG. 2C also depicts the approximate location of the basilic vein in subcutaneous tissue 220 below the skin 222. In some embodiments and as is disclosed below, the location of a blood vessel such as the basilic vein is of particular interest to monitoring blood glucose levels using millimeter range radio waves.

Figure 3:
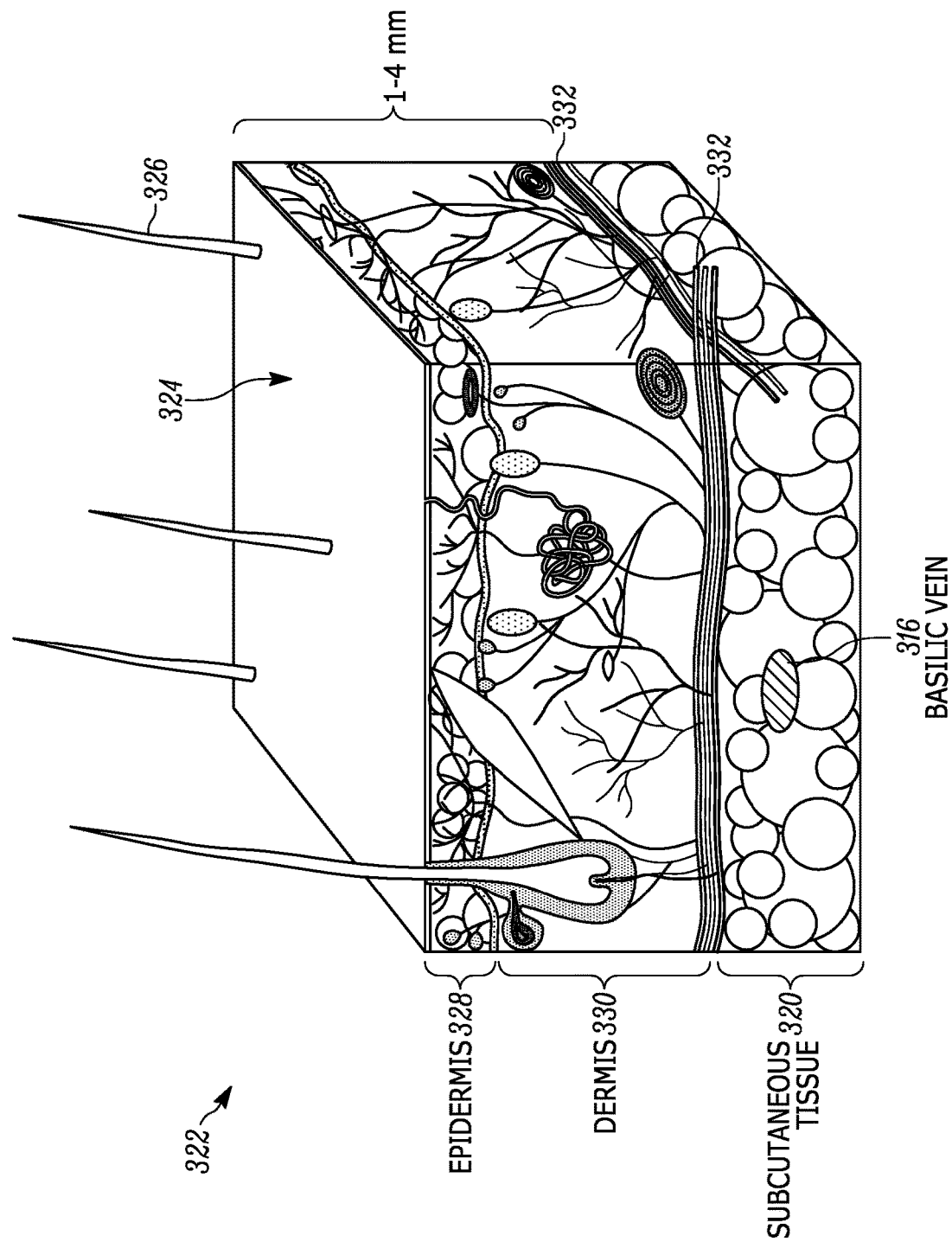
FIG. 3 is a perspective view of human skin that includes a skin surface, hairs, and the epidermis and dermis layers of the skin.

FIG. 3 is a perspective view of human skin 322 that includes a skin surface 324, hairs 326, and the epidermis 328 and dermis 330 layers of the skin. The skin is located on top of subcutaneous tissue 320. In an example, the thickness of human skin in the wrist area is around 1-4 mm and the thickness of the subcutaneous tissue may vary from 1-34 mm, although these thicknesses may vary based on many factors. As shown in FIG. 3, very small blood vessels 332 (e.g., capillaries having a diameter in the range of approximately 5-10 microns) are located around the interface between the dermis and the subcutaneous tissue while veins, such as the cephalic and basilic veins, are located in the subcutaneous tissue just below the skin. For example, the cephalic and basilic veins may have a diameter in the range of 1-4 mm and may be approximately 2-10 mm below the surface of the skin, although these diameters and depths may vary based on many factors. FIG. 3 depicts an example location of the basilic vein 316 in the area of the wrist.

Figure 4A:
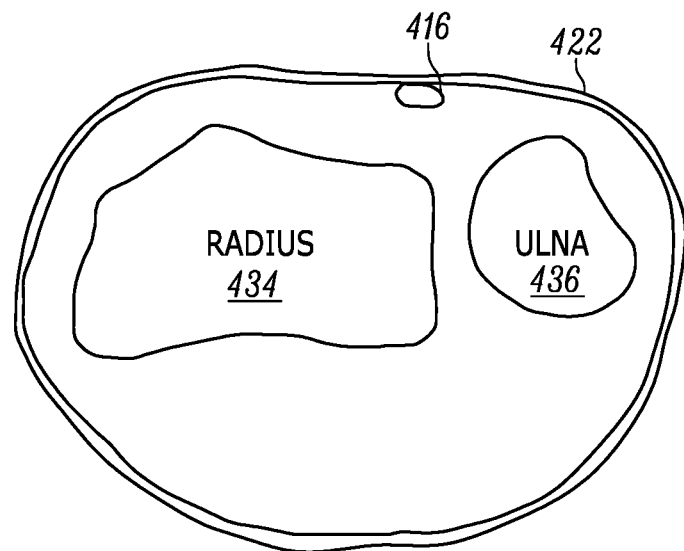
FIG. 4A depicts a simplified version of the cross-section of FIG. 2C, which shows the skin, the radius and ulna bones, and the basilic vein.
Figure 4B:
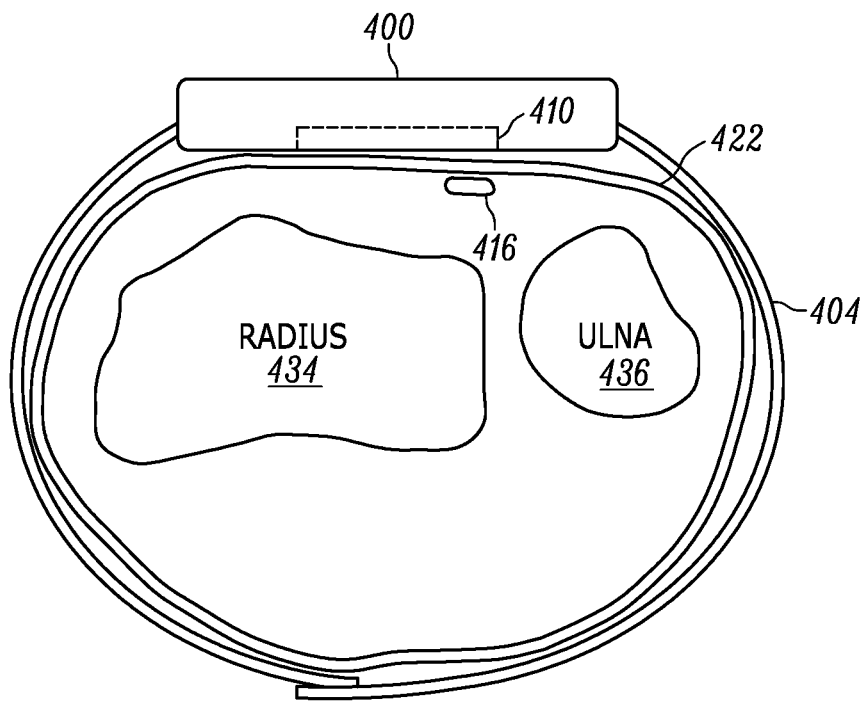
FIG. 4B depicts the wrist cross-section of FIG. 4A in a case where a smartwatch is attached to the wrist.

FIG. 4A depicts a simplified version of the cross-section of FIG. 2C, which shows the skin 422, the radius and ulna bones 434 and 436, and the basilic vein 416. FIG. 4B depicts the wrist cross-section of FIG. 4A in a case where a smartwatch 400, such as the smartwatch shown in FIGS. 1A and 1B, is attached to the wrist. FIG. 4B illustrates an example of the location of the smartwatch relative to the wrist and in particular relative to the basilic vein of the wrist. In the example of FIG. 4B, dashed line block 410 represents the approximate location of a sensor system and corresponds to the dashed line block 110 shown in FIG. 1B. The location of the smartwatch relative to the anatomy of the wrist, including the bones and a vein such as the basilic vein, is an important consideration in implementing blood glucose monitoring using millimeter range radio waves.

Figure 4C:
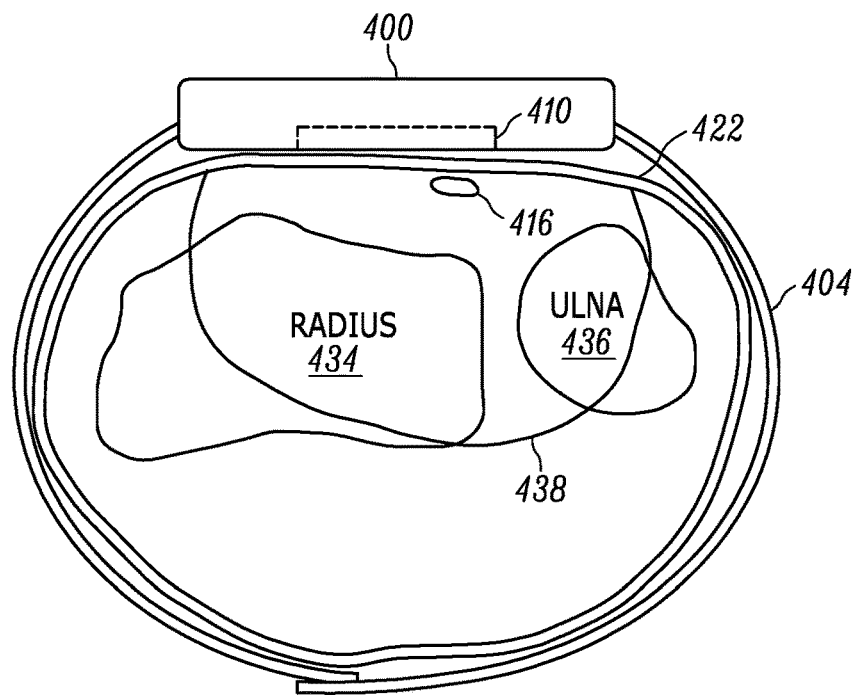
FIG. 4C illustrates, in two dimensions, an example of the penetration depth (which corresponds to a 3D illumination space) of radio waves transmitted from the sensor system of the smartwatch at a frequency of 60 GHz and a transmission power of 15 dBm.
Figure 4D:
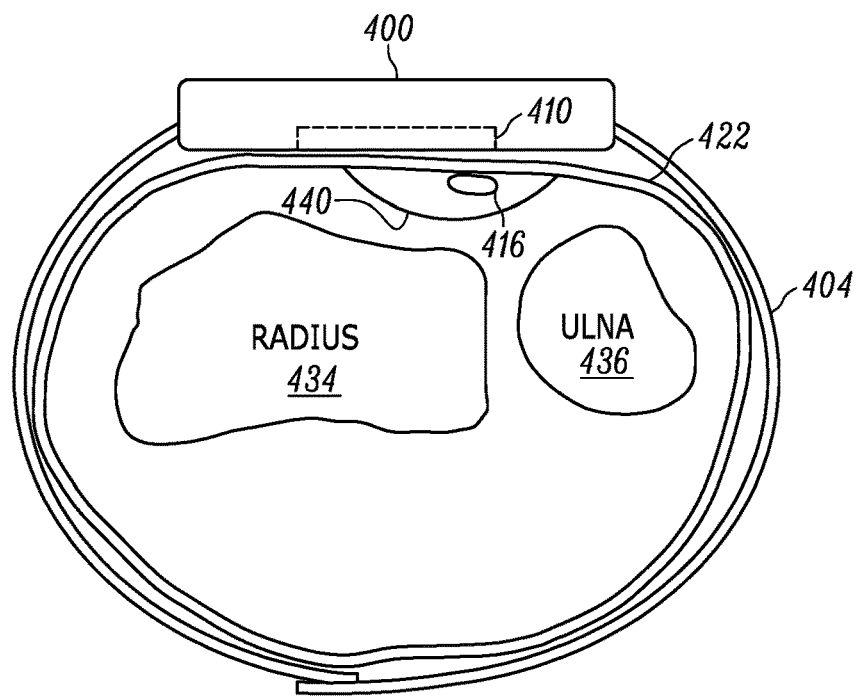
FIG. 4D illustrates, in two dimensions, an example of the penetration depth (which corresponds to a 3D illumination space) of radio waves transmitted from the sensor system of the smartwatch at a frequency of 122-126 GHz and transmit power of 15 dBm.

The magnitude of the reflected and received radio waves is a function of the power of the transmitted radio waves. With regard to the anatomy of the human body, it has been realized that radio waves transmitted at around 60 GHz at a particular transmission power level (e.g., 15 dBm) penetrate deeper (and thus illuminate a larger 3D space) into the human body than radio waves transmitted at 122-126 GHz at the same transmission power level (e.g., 15 dBm). FIG. 4C illustrates, in two dimensions, an example of the penetration depth (which corresponds to a 3D illumination space) of radio waves 438 transmitted from the sensor system of the smartwatch at a frequency of 60 GHz and a transmission power of 15 dBm. FIG. 4D illustrates, in two dimensions, an example of the penetration depth (which corresponds to a 3D illumination space) of radio waves 440 transmitted from the sensor system of the smartwatch at a frequency of 122-126 GHz and transmit power of 15 dBm, which is the same transmission power as used in the example of FIG. 4C. As illustrated by FIGS. 4C and 4D, for equivalent transmission powers (e.g., 15 dBm), radio waves 438 transmitted at 60 GHz penetrate deeper into the wrist (and thus have a corresponding larger illumination space) than radio waves 440 that are transmitted at 122-126 GHz. The deeper penetration depth of the 60 GHz radio waves results in more radio waves being reflected from anatomical features within the wrist. For example, a large quantity of radio waves will be reflected from the radius and ulna bones 434 and 436 in the wrist as well as from dense tissue such as tendons and ligaments that are located between the skin and the bones at the posterior of the wrist, see FIG. 2C, which shows tendons and ligaments that are located between the skin and the bones at the posterior of the wrist Likewise the shallower penetration of the 122-126 GHz radio waves results in fewer radio waves being reflected from undesired anatomical features within the wrist (e.g., anatomical features other than the targeted blood vessel or vein). For example, a much smaller or negligible magnitude of radio waves will be reflected from the radius and ulna bones in the wrist as well as from dense tissue such as tendons and ligaments that are located between the skin and the bones at the posterior of the wrist.

It has been realized that the penetration depth (and corresponding 3D illumination space), is an important factor in the complexity of the signal processing that is performed to obtain an identifiable signal that corresponds to the blood glucose level in the wrist (e.g., in the basilic vein of the wrist). In order to accurately measure the blood glucose level in a vein such as the basilic vein, it is desirable to isolate reflections from the area of the vein from all of the other reflections that are detected (e.g., from reflections from the radius and ulna bones in the wrist as well as from dense tissue such as tendons and ligaments that are located between the skin and the bones at the posterior of the wrist). In an embodiment, radio waves are transmitted at an initial power such that the power of the radio waves has diminished by approximately one-half (e.g., ±10%) at a depth of 6 mm below the skin surface. Reflections can be isolated using various techniques including signal processing techniques that are used for beamforming, Doppler effect, and/or leakage mitigation. The larger quantity of reflections in the 60 GHz case will likely need more intensive signal processing to remove signals that correspond to unwanted reflections in order to obtain a signal of sufficient quality to monitor a blood parameter such as the blood glucose level in a person.

Figure 5:
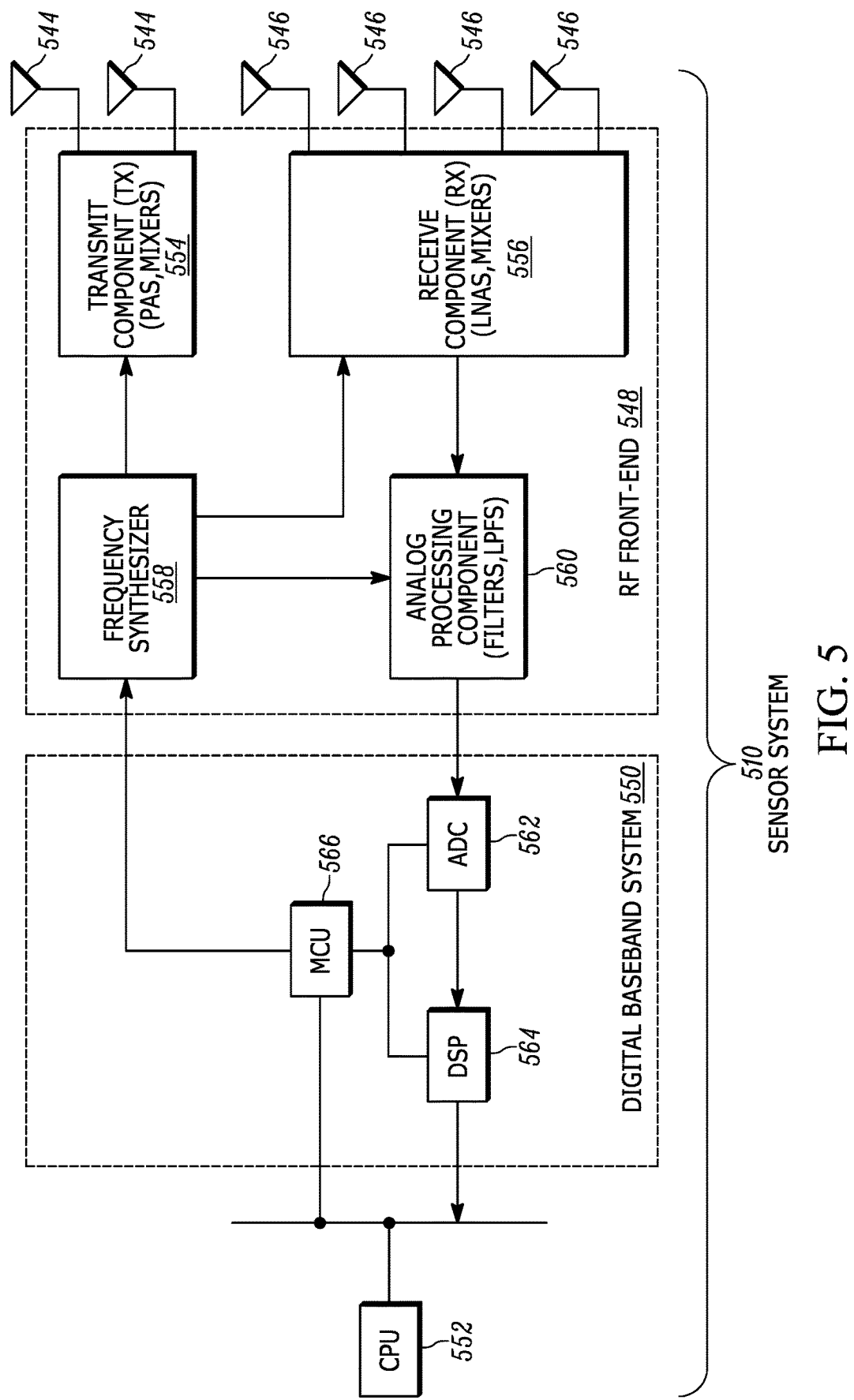
FIG. 5 depicts a functional block diagram of an embodiment of a sensor system that utilizes millimeter range radio waves to monitor a health parameter such as the blood glucose level in a person.

FIG. 5 depicts a functional block diagram of an embodiment of a sensor system 510 that utilizes millimeter range radio waves to monitor a health parameter such as the blood glucose level in a person. The sensor system includes transmit (TX) antennas 544, receive (RX) antennas 546, an RF front-end 548, a digital baseband system 550, and a CPU 552. The components of the sensor system may be integrated together in various ways. For example, some combination of components may be fabricated on the same semiconductor substrate and/or included in the same packaged IC device or a combination of packaged IC devices. As described above, in an embodiment, the sensor system is designed to transmit and receive radio waves in the range of 122-126 GHz.

In the embodiment of FIG. 5, the sensor system 510 includes two TX antennas 544 and four RX antennas 546. Although two TX and four RX antennas are used, there could be another number of antennas, e.g., one or more TX antennas and two or more RX antennas. In an embodiment, the antennas are configured to transmit and receive millimeter range radio waves. For example, the antennas are configured to transmit and receive radio waves in the 122-126 GHz frequency range, e.g., wavelengths in the range of 2.46-2.38 mm.

In the embodiment of FIG. 5, the RF front-end 548 includes a transmit (TX) component 554, a receive (RX) component 556, a frequency synthesizer 558, and an analogue processing component 560. The transmit component may include elements such as power amplifiers and mixers. The receive component may include elements such as low noise amplifiers (LNAs), variable gain amplifiers (VGAs), and mixers. The frequency synthesizer includes elements to generate electrical signals at frequencies that are used by the transmit and receive components. In an embodiment the frequency synthesizer may include elements such as a crystal oscillator, a phase-locked loop (PLL), a frequency doubler, and/or a combination thereof. The analogue processing component may include elements such as mixers and filters, e.g., low pass filters (LPFs). In an embodiment, components of the RF front-end are implemented in hardware as electronic circuits that are fabricated on the same semiconductor substrate.

The digital baseband system 550 includes an analog-to-digital converter (ADC) 562, a digital signal processor (DSP) 564, and a microcontroller unit (MCU) 566. Although the digital baseband system is shown as including certain elements, the digital baseband system may include some other configuration, including some other combination of elements. The digital baseband system is connected to the CPU 552 via a bus.

Figure 6:
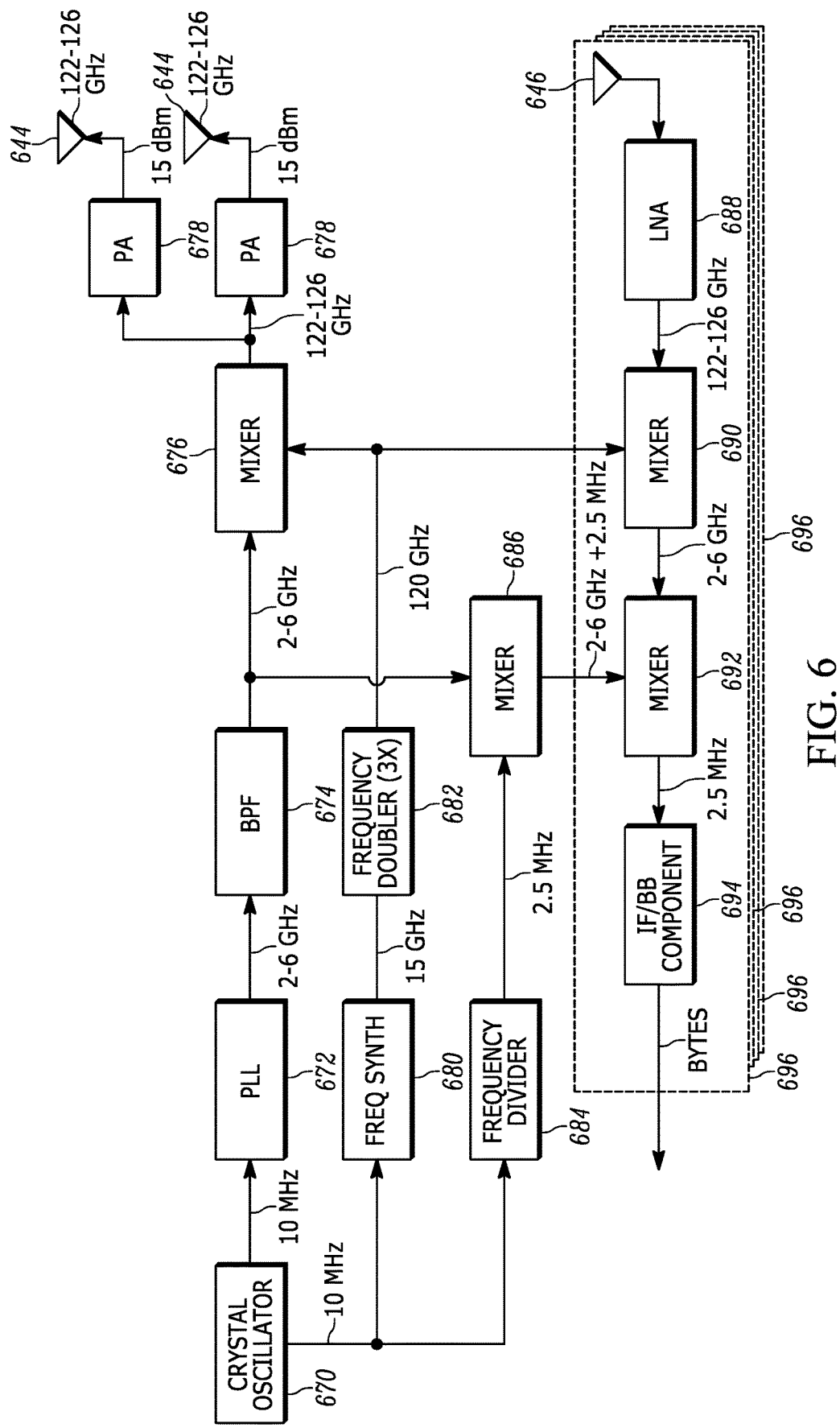
FIG. 6 depicts an expanded view of an embodiment of portions of the sensor system of FIG. 5, including elements of the RF front-end.

FIG. 6 depicts an expanded view of an embodiment of portions of the sensor system 510 of FIG. 5, including elements of the RF front-end. In the embodiment of FIG. 6, the elements include a crystal oscillator 670, a phase locked loop (PLL) 672, a bandpass filter (BPF) 674, a mixer 676, power amplifiers (PAs) 678, TX antennas 644, a frequency synthesizer 680, a frequency doubler 682, a frequency divider 684, a mixer 686, an RX antenna 646, a low noise amplifier (LNA) 688, a mixer 690, a mixer 692, and an Intermediate Frequency/Baseband (IF/BB) component 694. As illustrated in FIG. 6, the group of receive components identified within and dashed box 696 is repeated four times, e.g., once for each of four distinct RX antennas.

Operation of the system shown in FIG. 6 is described with reference to a transmit operation and with reference to a receive operation. The description of a transmit operation generally corresponds to a left-to-right progression in FIG. 6 and description of a receive operation generally corresponds to a right-to-left progression in FIG. 6. With regard to the transmit operation, the crystal oscillator 670 generates an analog signal at a frequency of 10 MHz. The 10 MHz signal is provided to the PLL 672, to the frequency synthesizer 680, and to the frequency divider 684. The PLL uses the 10 MHz signal to generate an analog signal that is in the 2-6 GHz frequency range. The 2-6 GHz signal is provided to the BPF 674, which filters the input signal and passes a signal in the 2-6 GHz range to the mixer 676. The 2-6 GHz signal is also provided to the mixer 686.

Dropping down in FIG. 6, the 10 MHz signal is used by the frequency synthesizer 680 to produce a 15 GHz signal. The 15 GHz signal is used by the frequency doubler 682 to generate a signal at 120 GHz. In an embodiment, the frequency doubler includes a series of three frequency doublers that each double the frequency, e.g., from 15 GHz to 30 GHz, and then from 30 GHz to 60 GHz, and then from 60 GHz to 120 GHz. The 120 GHz signal and the 2-6 GHz signal are provided to the mixer 676, which mixes the two signals to generate a signal at 122-126 GHz depending on the frequency of the 2-6 GHz signal. The 122-126 GHz signal output from the mixer 676 is provided to the power amplifiers 678, and RF signals in the 122-126 GHz range are output from the TX antennas 644. In an embodiment, the 122-126 GHz signals are output at 15 dBm (decibels (dB) with reference to 1 milliwatt (mW)). In an embodiment and as described below, the PLL is controlled to generate discrete frequency pulses between 2-6 GHz that are used for stepped frequency transmission.

The 10 MHz signal from the crystal oscillator 670 is also provided to the frequency divider 684, which divides the frequency down, e.g., from 10 MHz to 2.5 MHz via, for example, two divide by two operations, and provides an output signal at 2.5 MHz to the mixer 686. The mixer 686 also receives the 2-6 GHz signal from the BPF 674 and provides a signal at 2-6 GHz+2.5 MHz to the mixer 692 for receive signal processing.

With reference to a receive operation, electromagnetic (EM) energy is received at the RX antenna 646 and converted to electrical signals, e.g., voltage and current. For example, electromagnetic energy in the 122-126 GHz frequency band is converted to an electrical signal that corresponds in frequency (e.g., GHz), magnitude (e.g., power in dBm), and phase to the electromagnetic energy that is received at the RX antenna. The electrical signal is provided to the LNA 688. In an embodiment, the LNA amplifies signals in the 122-126 GHz frequency range and outputs an amplified 122-126 GHz signal. The amplified 122-126 GHz signal is provided to the mixer 690, which mixes the 120 GHz signal from the frequency doubler 682 with the received 122-126 GHz signal to generate a 2-6 GHz signal that corresponds to the electromagnetic energy that was received at the RX antenna. The 2-6 GHz signal is then mixed with the 2-6 GHz+2.5 MHz signal at mixer 692 to generate a 2.5 MHz signal that corresponds to the electromagnetic energy that was received at the RX antenna. For example, when a 122 GHz signal is being transmitted from the TX antennas and received at the RX antenna, the mixer 692 receives a 2 GHz signal that corresponds to the electromagnetic energy that was received at the antenna and a 2 GHz+2.5 MHz signal from the mixer 686. The mixer 692 mixes the 2 GHz signal that corresponds to the electromagnetic energy that was received at the RX antenna with the 2 GHz+2.5 MHz signal from the mixer 686 to generate a 2.5 MHz signal that corresponds to the electromagnetic energy that was received at the RX antenna. The 2.5 MHz signal that corresponds to the electromagnetic energy that was received at the RX antenna is provided to the IF/BB component 694 for analog-to-digital conversion. The above-described receive process can be implemented in parallel on each of the four receive paths 696. As is described below, the system described with reference to FIG. 6 can be used to generate various discrete frequencies that can be used to implement, for example, stepped frequency radar detection. As described above, multiple mixing operations are performed to implement a sensor system at such a high frequency, e.g., in the 122-126 GHz range. The multiple mixers and corresponding mixing operations implement a "compound mixing" architecture that enables use of such high frequencies.

Figure 7:
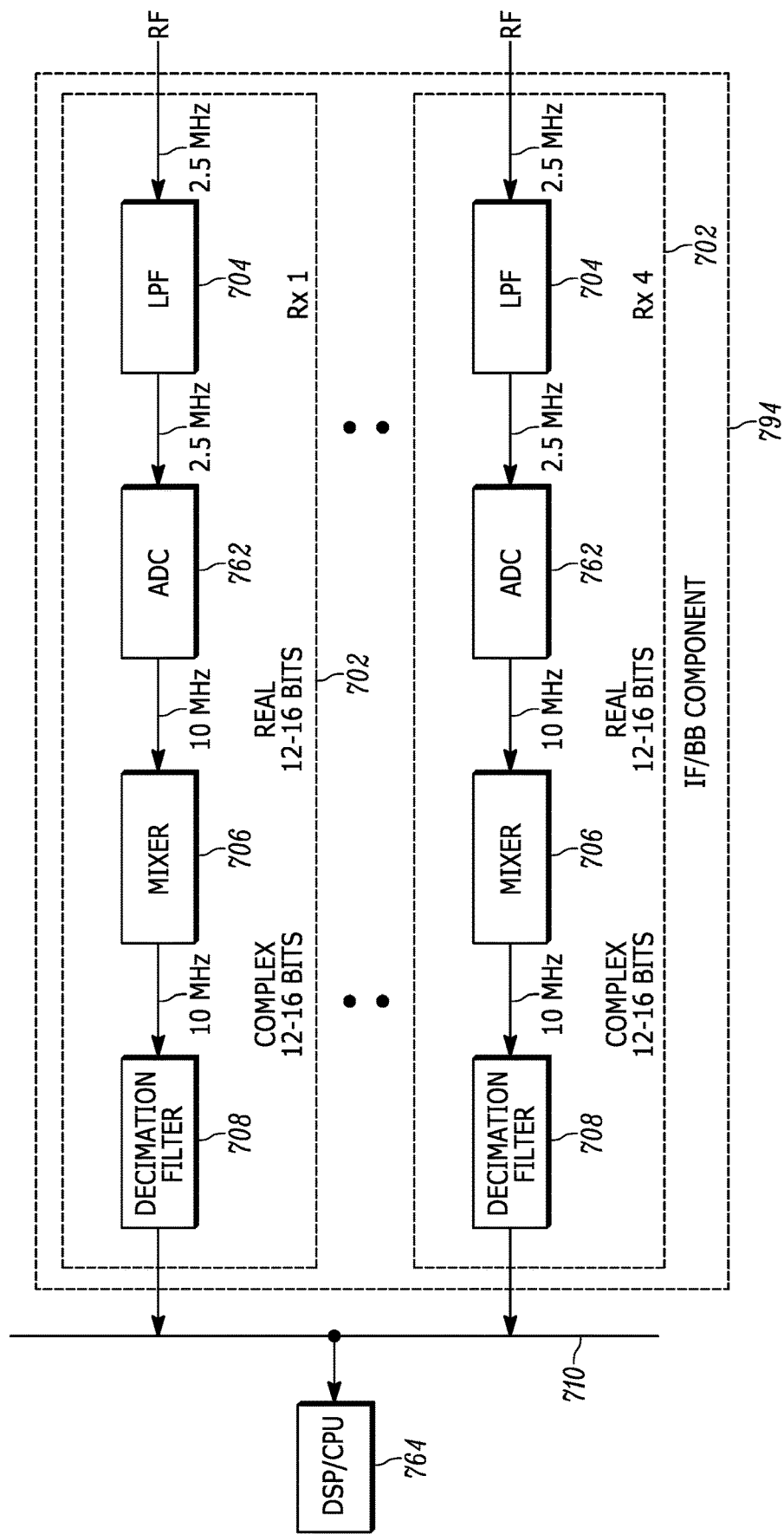
FIG. 7 depicts an embodiment of the IF/BB component shown in FIG. 6.

FIG. 7 depicts an embodiment of the IF/BB component 794 shown in FIG. 6. The IF/BB component of FIG. 7 includes similar signal paths 702 for each of the four receive paths/RX antennas and each signal path includes a low pass filter (LPF) 704, an analog-to-digital converter (ADC) 762, a mixer 706, and a decimation filter 708. The operation of receive path 1, RX1, is described.

As described above with reference to FIG. 6, the 2.5 MHz signal from mixer 692 (FIG. 6) is provided to the IF/BB component 694/794, in particular, to the LPF 704 of the IF/BB component 794. In an embodiment, the LPF filters the 2.5 MHz signal to remove the negative frequency spectrum and noise outside of the desired bandwidth. After passing through the LPF, the 2.5 MHz signal is provided to the ADC 762, which converts the 2.5 MHz signal (e.g., IF signal) to digital data at a sampling rate of 10 MHz (e.g., as 12-16 bits of "real" data). The mixer 706 multiplies the digital data with a complex vector to generate a digital signal (e.g., 12-16 bits of "complex" data), which is also sampled at 10 MHz. Although the signal is sampled at 10 MHz, other sampling rates are possible, e.g., 20 MHz. The digital data sampled at 10 MHz is provided to the decimation filter, which is used to reduce the amount of data by selectively discarding a portion of the sampled data. For example, the decimation filter reduces the amount of data by reducing the sampling rate and getting rid of a certain percentage of the samples, such that fewer samples are retained. The reduction in sample retention can be represented by a decimation factor, M, and may be, for example, about 10 or 100 depending on the application, where M equals the input sample rate divided by the output sample rate.

The output of the decimation filter 708 is digital data that is representative of the electromagnetic energy that was received at the corresponding RX antenna. In an embodiment, samples are output from the IF/BB component 794 at rate of 1 MHz (using a decimation factor of 10) or at a rate of 100 kHz (using a decimation factor of 100). The digital data is provided to a DSP and/or CPU 764 via a bus 710 for further processing. For example, the digital data is processed to isolate a signal from a particular location, e.g., to isolate signals that correspond to electromagnetic energy that was reflected by the blood in a vein of the person. In an embodiment, signal processing techniques are applied to implement beamforming, Doppler effect processing, and/or leakage mitigation to isolate a desired signal from other undesired signals.

In conventional RF systems, the analog-to-digital conversion process involves a high direct current (DC), such that the I ("real") and Q ("complex") components of the RF signal at DC are lost at the ADC. Using the system as described above with reference to FIGS. 5-7, the intermediate IF is not baseband, so I and Q can be obtained after analog-to-digital conversion and digital mixing as shown in FIG. 7.

In an embodiment, digital signal processing of the received signals may involve implementing Kalman filters to smooth out noisy data. In another embodiment, digital signal processing of the received signals may involve combining receive chains digitally. Other digital signal processing may be used to implement beamforming, Doppler effect processing, and ranging. Digital signal processing may be implemented in a DSP and/or in a CPU.

In an embodiment, certain components of the sensor system are integrated onto a single semiconductor substrate and/or onto a single packaged IC device (e.g., a packaged IC device that includes multiple different semiconductor substrates (e.g., different die) and antennas). For example, elements such as the components of the RF front-end 548, and/or components of the digital baseband system 550 (FIGS. 5-7) are integrated onto the same semiconductor substrate (e.g., the same die). In an embodiment, components of the sensor system are integrated onto a single semiconductor substrate that is approximately 5 mm×5 mm. In an embodiment, the TX antennas and RX antennas are attached to an outer surface of the semiconductor substrate and/or to an outer surface of an IC package and electrically connected to the circuits integrated into the semiconductor substrate. In an embodiment, the TX and RX antennas are attached to the outer surface of the IC package such that the TX and RX antenna attachments points are very close to the corresponding transmit and receive circuits such as the PAs and LNAs. In an embodiment, the semiconductor substrate and the packaged IC device includes outputs for outputting electrical signals to another components such as a DSP, a CPU, and or a bus. In some embodiments, the packaged IC device may include the DSP and/or CPU or the packaged IC device may include some DSP and/or CPU functionality.

Figure 8A:
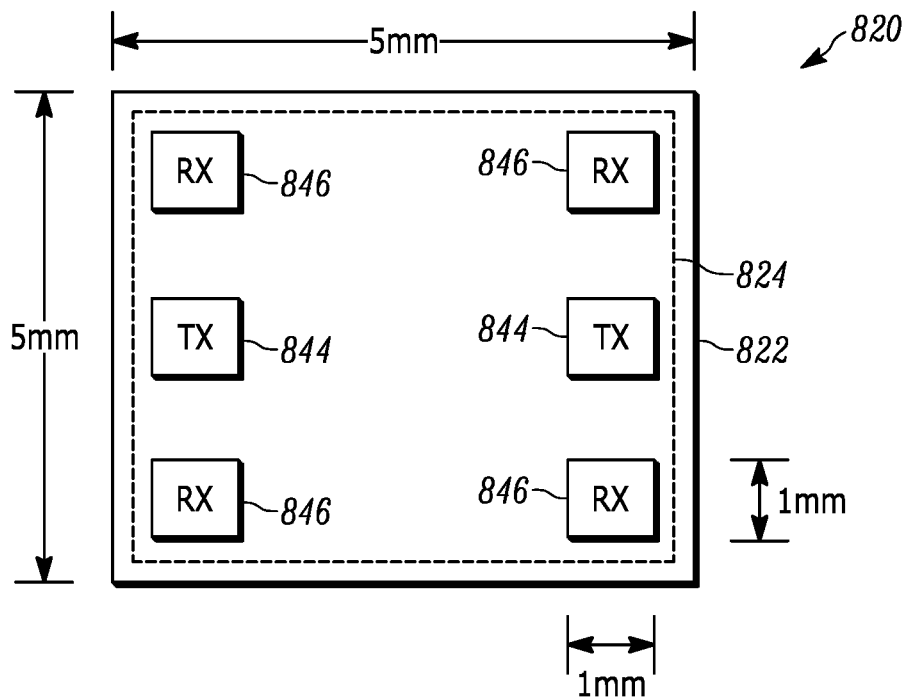
FIG. 8A depicts an example embodiment of a plan view of an IC device that includes two TX antennas and four antennas 846 as well as some of the components from the RF front-end and the digital baseband (not shown) as described above with regard to FIGS. 5-7.
Figure 8B:
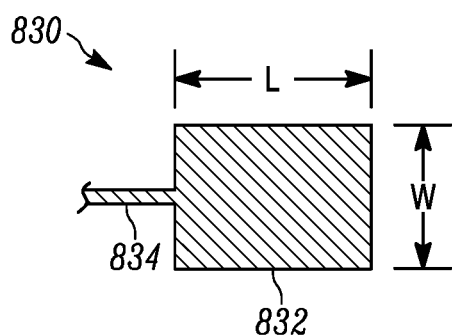
FIG. 8B depicts an embodiment of a microstrip patch antenna that can be used for the TX and/or RX antennas of the IC device of FIG. 8A.

FIG. 8A depicts an example embodiment of a plan view of an IC device 820 that includes two TX antennas 844 and four RX antennas 846 as well as some of the components from the RF front-end and the digital baseband (not shown) as described above with regard to FIGS. 5-7. In FIG. 8A, the outer footprint of the IC device represents a packaged IC device 822 and the inner footprint (as represented by the dashed box 824) represents a semiconductor substrate that includes circuits that are fabricated into the semiconductor substrate to conduct and process electrical signals that are transmitted by the TX antennas and/or received by the RX antennas. In the embodiment of FIG. 8A, the packaged IC device has dimensions of 5 mm×5 mm (e.g., referred to as the device "footprint") and the semiconductor substrate has a footprint that is slightly smaller than the footprint of the packaged IC device, e.g., the semiconductor substrate has dimensions of approximately 0.1-1 mm less than the packaged IC device on each side. Although not shown, in an example embodiment, the packaged IC device has a thickness of approximately 0.3-2 mm and the semiconductor substrate has a thickness in the range of about 0.1-0.7 mm. In an embodiment, the TX and RX antennas are designed for millimeter range radio waves, for example, radio waves of 122-126 GHz have wavelengths in the range of 2.46 to 2.38 mm. In FIG. 8A, the TX and RX antennas are depicted as square boxes of approximately 1 mm×1 mm and the antennas are all attached on the same planar surface of the IC device package. For example, the antennas are attached on the top surface of the IC package (e.g., on top of a ceramic package material) directly above the semiconductor substrate with conductive vias that electrically connect a conductive pad of the semiconductor substrate to a transmission line of the antenna. Although the TX and RX antennas may not be square, the boxes correspond to an approximate footprint of the TX and RX antennas. In an embodiment, the antennas are microstrip patch antennas and the dimensions of the antennas are a function of the wavelength of the radio waves. Other types of antennas such as dipole antennas are also possible. FIG. 8B depicts an embodiment of a microstrip patch antenna 830 that can be used for the TX and/or RX antennas 844 and 846 of the IC device of FIG. 8A. As shown in FIG. 8B, the microstrip patch antenna has a patch portion 832 (with dimensions length (L)×width (W)) and a microstrip transmission line 834. In some embodiments, microstrip patch antennas have length and width dimensions of one-half the wavelength of the target radio waves. Thus, microstrip patch antennas designed for radio waves of 122-126 GHz (e.g., wavelengths in the range of 2.46 to 2.38 mm), the patch antennas may have length and width dimensions of around 1.23-1.19 mm, but no more than 1.3 mm. It is noted that because antenna size is a function of wavelength, the footprint of the antennas shown in FIGS. 8A and 8B can be made to be around one-half the size of antennas designed for radio waves around 60 GHz (e.g., wavelength of approximately 5 mm). Additionally, the small antenna size of the antennas shown in FIGS. 8A and 8B makes it advantageous to attach all six of the antennas to the top surface of the package of the IC device within the footprint of the semiconductor substrate, which makes the packaged IC device more compact than known devices such as the "Soli" device. That is, attaching all of the TX and RX antennas within the footprint of the semiconductor substrate (or mostly within the footprint of the semiconductor substrate, e.g., greater than 90% within the footprint).

In an embodiment, the RX antennas form a phased antenna array and for the application of health monitoring it is desirable to have as much spatial separation as possible between the RX antennas to improve overall signal quality by obtaining unique signals from each RX antenna. For example, spatial separation of the RX antennas enables improved depth discrimination to isolate signals that correspond to reflections from blood in a vein from reflections from other anatomical features. Thus, as shown in FIG. 8A, the RX antennas 846 are located at the corners of the rectangular shaped IC device. For example, the RX antennas are located flush with the corners of the semiconductor substrate 824 and/or flush with the corners of the IC device package or within less than about 0.5 mm from the corners of the semiconductor substrate 824 and/or from the corners of the IC device package. Although the IC device shown in FIG. 8A has dimensions of 5 mm×5 mm, IC devices having smaller (e.g., approximately 3 mm×3 mm) or larger dimensions are possible. In an embodiment, the IC device has dimensions of no more than 7 mm×7 mm.

In the embodiment of FIG. 8A, the TX antennas 844 are located on opposite sides of the IC chip approximately in the middle between the two RX antennas 846 that are on the same side. As shown in FIG. 8A, the TX antenna on the left side of the IC device is vertically aligned with the two RX antennas on the left side of the IC device and the TX antenna on the right side of the IC device is vertically aligned with the two RX antennas on the right side of the IC device. Although one arrangement of the TX and RX antennas is shown in FIG. 8A, other arrangements are possible.

Figure 8C:
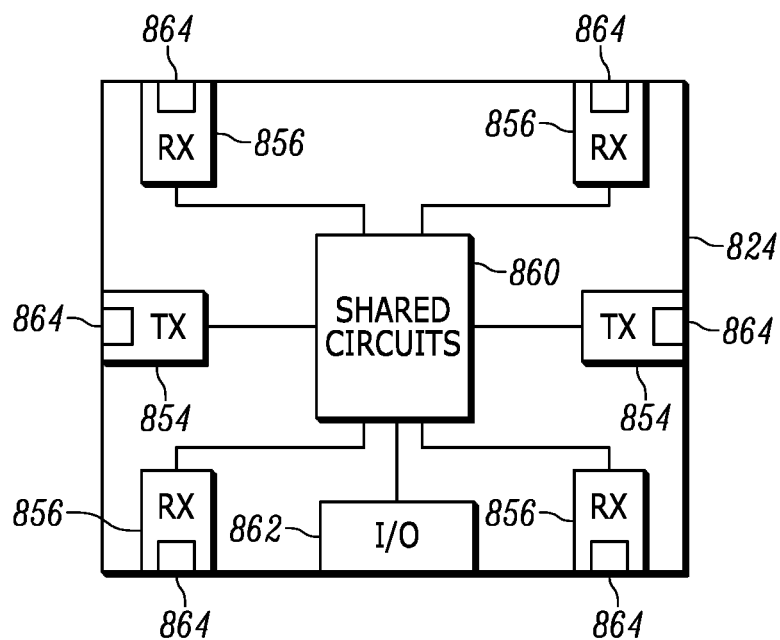
FIG. 8C depicts an example of the physical layout of circuit components on a semiconductor substrate, such as the semiconductor substrate (die) depicted in FIG. 8A.
Figure 8D:
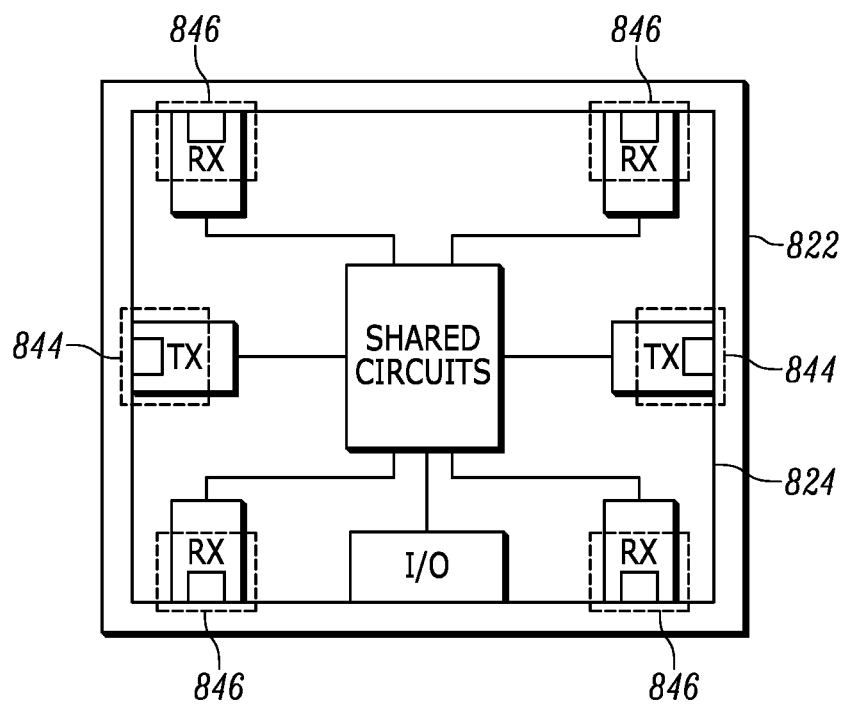
FIG. 8D depicts a packaged IC device similar to the packaged IC device shown in FIG. 8A superimposed over the semiconductor substrate shown in FIG. 8C.

At extremely high frequencies (e.g., 30-300 GHz) conductor losses can be very significant. Additionally, conductor losses at extremely high frequencies are known to be frequency-dependent, with higher frequencies exhibiting higher conductor losses. In many health monitoring applications, power, such as battery power, is a limited resource that must be conserved. Additionally, for reasons as described above such as limiting undesired reflections, low power transmissions may be desirable for health monitoring reasons. Because of the low power environment, conductor losses can severely impact performance of the sensor system. For example, significant conductor losses can occur between the antennas and the conductive pads of the semiconductor substrate, or "die," and between the conductive pads and the transmit/receive components in the die, e.g., the channel-specific circuits such as amplifiers, filters, mixers, etc. In order to reduce the impact of conductor losses in the sensor system, it is important to locate the antennas as close to the channel-specific transmit/receive components of the die as possible. In an embodiment, the transmit and receive components are strategically fabricated on the semiconductor substrate in locations that correspond to the desired locations of the antennas. Thus, when the TX and RX antennas are physically and electrically attached to the IC device, the TX and RX antennas are as close as possible to the transmit and receive components on the die, e.g., collocated such that a portion of the channel specific transmit/receive component overlaps from a plan view perspective a portion of the respective TX/RX antenna. FIG. 8C depicts an example of the physical layout of circuit components on a semiconductor substrate, such as the semiconductor substrate (die) depicted in FIG. 8A. In the embodiment of FIG. 8C, the die 824 includes two TX components 854, four RX components 856, shared circuits 860, and an input/output interface (I/O) 862. In the example of FIG. 8C, each TX component includes channel-specific circuits (not shown) such as amplifiers, each RX component includes channel-specific circuits (not shown) such as mixers, filters, and LNAs, and the shared circuits include, for example, a voltage control oscillator (VCO), a local oscillator (LO), frequency synthesizers, PLLs, BPFs, divider(s), mixers, ADCs, buffers, digital logic, a DSP, CPU, or some combination thereof that may be utilized in conjunction with the channel-specific TX and RX components. As shown in FIG. 8C, the transmit and receive components 854 and 856 each include an interface 864 (such as a conductive pad) that provides an electrical interface between the circuits on the die and a corresponding antenna. FIG. 8D depicts a packaged IC device 822 similar to the packaged IC device shown in FIG. 8A superimposed over the semiconductor substrate 824 shown in FIG. 8C. FIG. 8D illustrates the locations of the TX and RX antennas 844 and 846 relative to the transmit and receive components 854 and 856 of the die (from a plan view perspective). As illustrated in FIG. 8D, the TX and RX antennas 844 and 846 are located directly over the interfaces 864 of the corresponding transmit and receive components 854 and 856. In an embodiment in which the antennas are attached to a top surface of the package (which may be less than 0.5 mm thick), the antennas can be connected to the interface of the respective transmit/receive components by a distance that is a fraction of a millimeter. In an embodiment, a via that is perpendicular to the plane of the die connects the interface of the transmit/receive component to a transmission line of the antenna. More than one via may be used when the antenna has more than one transmission line. Such a collocated configuration enables the desired distribution of the TX and RX antennas to be maintained while effectively managing conductor losses in the system. Such a close proximity between antennas and channel-specific circuits of the die is extremely important at frequencies in the 122-126 GHz range and provides an improvement over sensor systems that include conductive traces of multiple millimeters between the antennas and the die.

Although the example of FIGS. 8A-8D shows the antennas within the footprint of the packaged IC device 822, in some other embodiments, the antennas may extend outside the footprint of the die and/or the packaged IC device while still being collocated with the corresponding transmit/receive components on the die. For example, the antennas may be dipole antennas that have portions of the antennas that extend outside the footprint of the die and/or the packaged IC device.

It has been realized that for the application of monitoring a health parameter such as the blood glucose level in the blood of a person, it is important that the TX antennas are able to illuminate at least one vein near the skin of the person. In order for a TX antenna to illuminate at least one vein near the skin of the person, it is desirable for at least one of the antennas to be spatially close to a vein. Because of variations in the locations of veins relative to the location of the monitoring system (e.g., a smartwatch), it has been found that a transverse configuration of the TX antennas relative to the expected location of a vein or veins provides desirable conditions for monitoring a health parameter such as the blood glucose level in the blood of a person. When the wearable device is worn on a portion of a limb such as the wrist, the TX antennas are distributed in a transverse configuration relative to the limb and relative to the expected location of a vein or veins that will be illuminated by the TX antennas.

Figure 9:
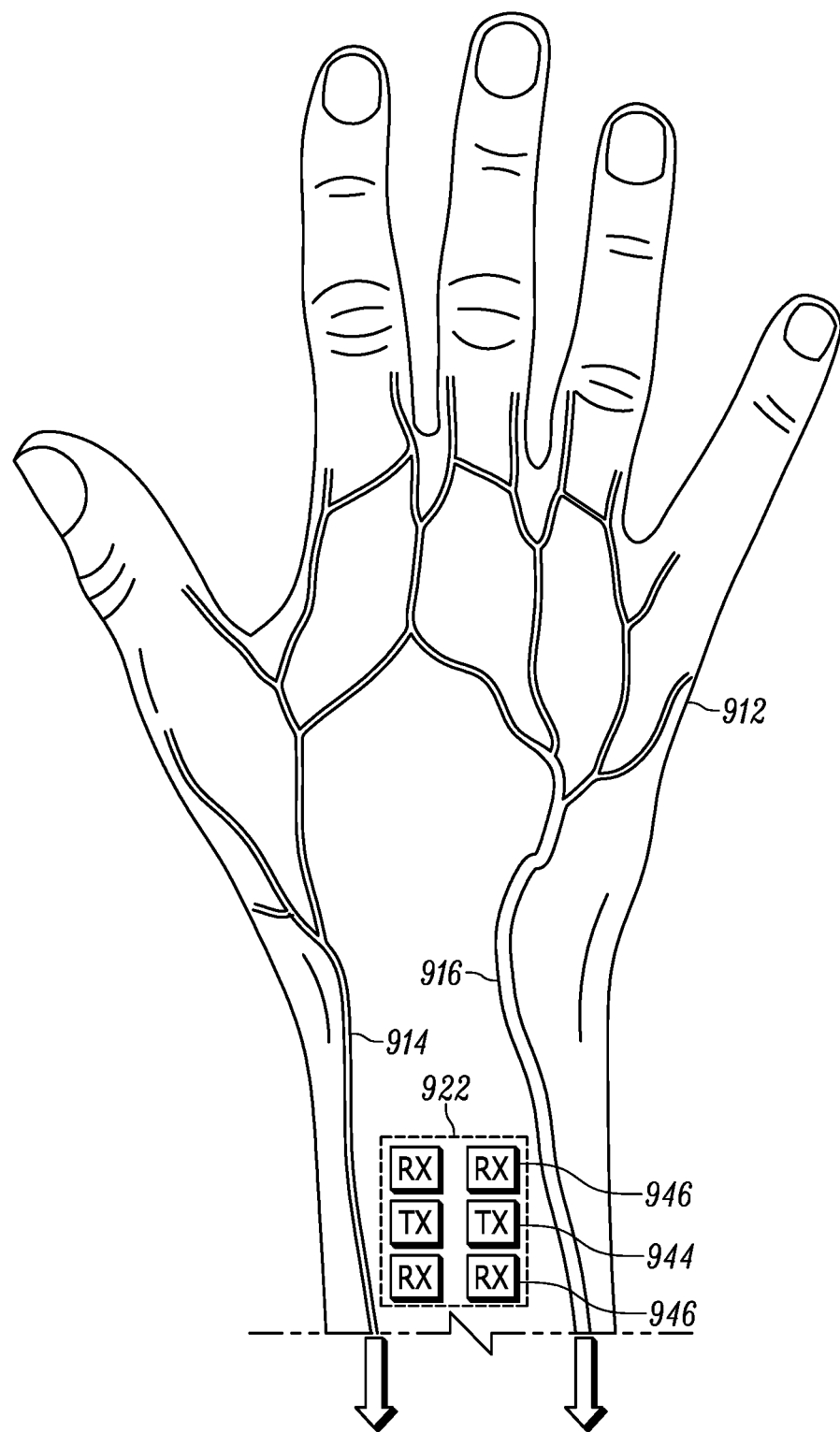
FIG. 9 depicts an IC device similar to that of FIG. 8A overlaid on the hand/wrist that is described above with reference to FIG. 2A-2C.

FIG. 9 depicts an IC device 922 similar to that of FIG. 8A overlaid on the hand/wrist 912 that is described above with reference to FIG. 2A-2C. The IC device is oriented with regard to the basilic and cephalic veins 914 and 916 such that the two TX antennas 944 are configured transverse to the basilic and cephalic veins. That is, the two TX antennas are distributed transversely relative to the orientation (e.g., the linear direction) of the vessel or vessels that will be monitored, such as the basilic and cephalic veins. For example, in a transverse configuration, a straight line that passes through the two TX antennas would be transverse to the vessel or vessels that will be monitored, such as the basilic and cephalic veins. In an embodiment in which the wearable device is worn on the wrist, the transverse configuration of the TX antennas is such that a line passing through both of the TX antennas is approximately orthogonal to the wrist and approximately orthogonal to the orientation of the vessel or vessels that will be monitored, such as the basilic and cephalic veins. For example, a line passing through both of the TX antennas and the orientation of the vessel or vessels that will be monitored, such as the basilic and cephalic veins, may be without about 20 degrees from orthogonal.

Figure 10:
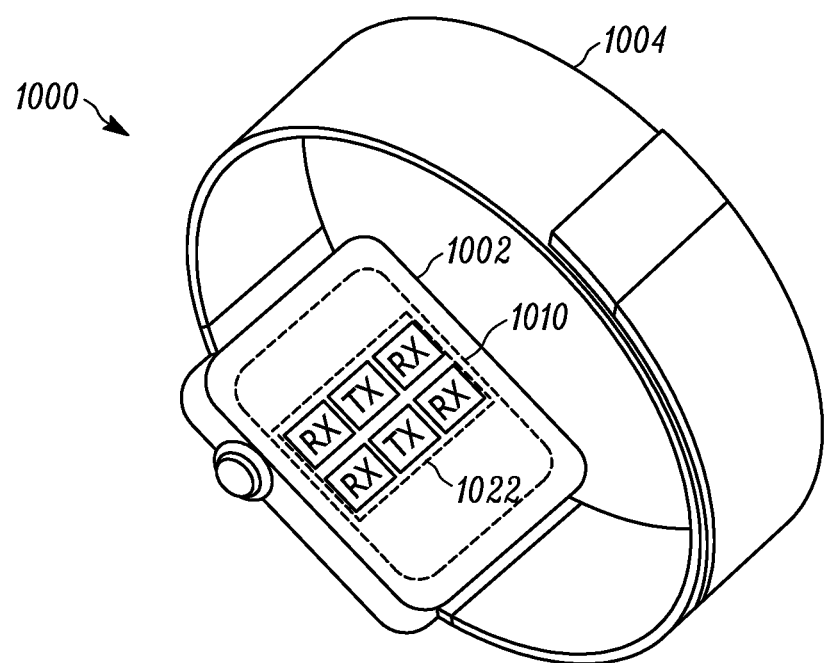
FIG. 10 depicts an IC device similar to that of FIG. 8A overlaid on the back of the smartwatch.

FIG. 10 depicts an IC device 1022 similar to that of FIG. 8A overlaid on the back of the smartwatch 1000 described above with reference to FIGS. 1A and 1B. As shown in FIGS. 9 and 10, the two TX antennas are configured such that when the smartwatch is worn on the wrist, the two TX antennas are transverse to veins such as the basilic and cephalic veins that run parallel to the length of the arm and wrist.

Figure 11:
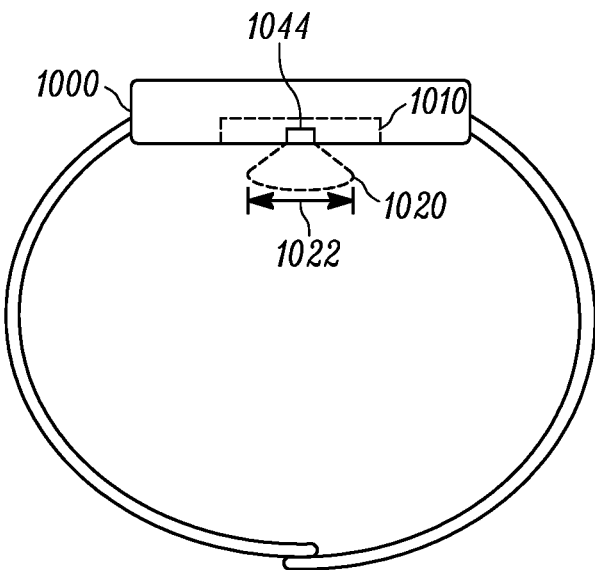
FIG. 11 depicts a side view of a sensor system in a case in which the two TX antennas are configured parallel to veins such as the basilic and cephalic veins of a person wearing the smartwatch.
Figure 12:
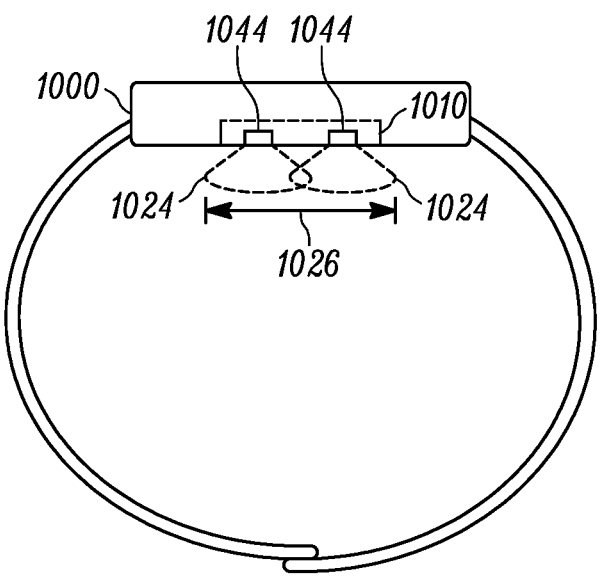
FIG. 12 depicts the same side view as shown in FIG. 11 in a case in which the two TX antennas are configured transverse to veins such as the basilic and cephalic veins of a person wearing the smartwatch.

FIGS. 11 and 12 are provided to illustrate the expanded illumination volume that can be achieved by a sensor system 1010 that includes a transverse TX antenna configuration. FIG. 11 depicts a side view of a sensor system in a case in which the two TX antennas 1044 are configured parallel to veins such as the basilic and cephalic veins of a person wearing the smartwatch 1000. In the view shown in FIG. 11, the two TX antennas are in-line with each other such that only one of the two TX antennas is visible from the side view. When the TX antennas transmit millimeter range radio waves, the electromagnetic energy may have a two-dimensional (2D) illumination pattern as illustrated by dashed line 1020. Given the two-dimensional pattern as illustrated in FIG. 11, the two TX antennas illuminate an area that has a maximum width in the transverse direction (transverse to veins that run parallel to the length of the arm and wrist and referred to herein as the transverse width) identified by arrow 1022. Although the illumination pattern is described and illustrated in two dimensions (2D), it should be understood that illumination actually covers a 3D space or volume.

FIG. 12 depicts the same side view as shown in FIG. 11 in a case in which the two TX antennas 1044 are configured transverse to veins such as the basilic and cephalic veins of a person wearing the smartwatch 1000. In the view shown in FIG. 12, the two TX antennas are spatially separated from each other such that both of the TX antennas are visible from the side view. When the TX antennas transmit millimeter range radio waves, the electromagnetic energy may have a 2D illumination pattern as illustrated by dashed lines 1024. Given the 2D elimination patterns of the two TX antennas, the two TX antennas combine to illuminate an area that has a width in the transverse direction (transverse width) identified by arrow 1026, which is wider than the transverse width for the TX antenna configuration shown in FIG. 11 (e.g., almost twice as wide). A wider illumination area improves the coverage area for the sensor system 1010 and increases the likelihood that the sensor system will illuminate a vein in the person wearing the smartwatch. An increased likelihood that a vein is illuminated can provide more reliable feedback from the feature of interest (e.g., blood in the vein) and thus more reliable monitoring results. Additionally, a wider illumination area can increase the power of the radio waves that illuminate a vein, resulting in an increase in the power of the electromagnetic energy that is reflected from the vein, which can improve the quality of the received signals.

It has been established that the amount of glucose in the blood (blood glucose level) affects the reflectivity of millimeter range radio waves. However, when millimeter range radio waves are applied to the human body (e.g., at or near the skin surface), electromagnetic energy is reflected from many objects including the skin itself, fibrous tissue such as muscle and tendons, and bones. In order to effectively monitor a health parameter such as the blood glucose level of a person, electrical signals that correspond to electromagnetic energy that is reflected from blood (e.g., from the blood in a vein) should be isolated from electrical signals that correspond to electromagnetic energy that is reflected from other objects such as the skin itself, fibrous tissue, and bone, as well as from electrical signals that correspond to electromagnetic energy that is emitted directly from the TX antennas (referred to herein as electromagnetic energy leakage or simply as "leakage") and received by an antenna without passing through the skin of the person.

Various techniques that can be implemented alone or in combination to isolate electrical signals that correspond to reflections from blood from other electrical signals that correspond to other reflections (such as reflections from bone and/or fibrous tissue such as muscle and tendons) and/or signals that correspond to leakage are described below. Such techniques relate to and/or involve, for example, transmission characteristics, beamforming, Doppler effect processing, leakage mitigation, and antenna design.

As is known in the field, radar detection involves transmitting electromagnetic energy and receiving reflected portions of the transmitted electromagnetic energy. Techniques for transmitting electromagnetic energy in radar systems include impulse, chirp, and stepped frequency techniques.

Figure 13A:
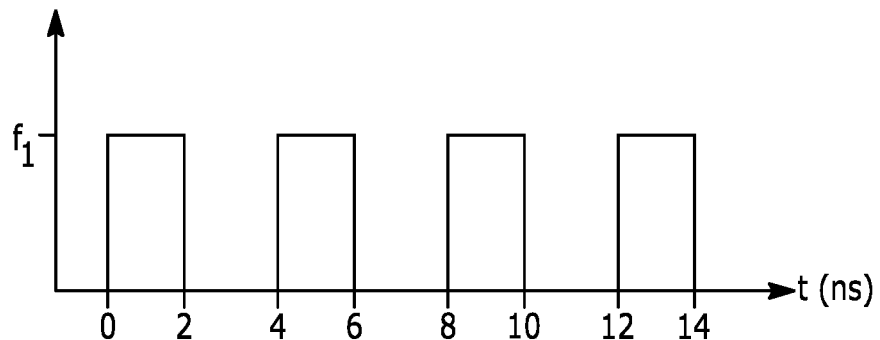
FIGS. 13A-13C depict frequency versus time graphs of impulse, chirp, and stepped frequency techniques for transmitting electromagnetic energy in a radar system.
Figure 13B:
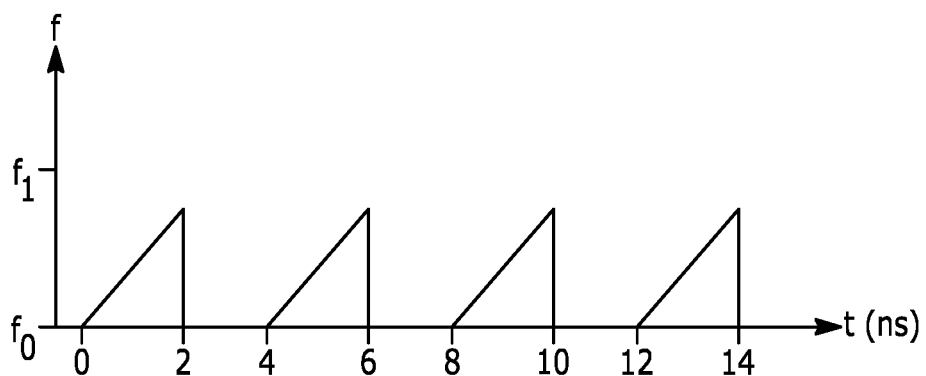
Figure 13C:
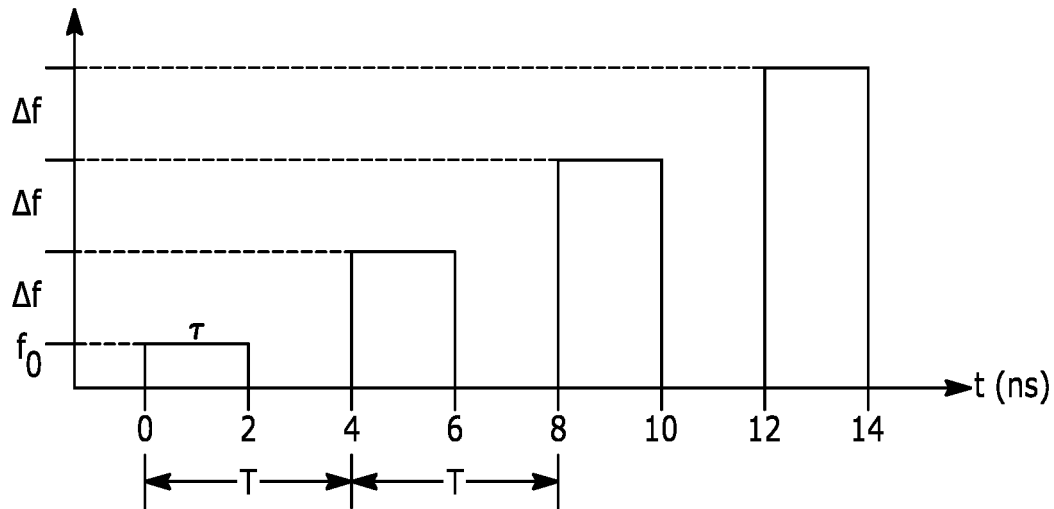

FIGS. 13A-13C depict frequency versus time graphs of impulse, chirp, and stepped frequency techniques for transmitting electromagnetic energy in a radar system. FIG. 13A depicts a radar transmission technique that involves transmitting pulses of electromagnetic energy at the same frequency for each pulse, referred to as "impulse" transmission. In the example of FIG. 13A, each pulse is at frequency, $f_1$, and lasts for a constant interval of approximately 2 ns. The pulses are each separated by approximately 2 ns.

FIG. 13B depicts a radar transmission technique that involves transmitting pulses of electromagnetic energy at an increasing frequency for each interval, referred to herein as "chirp" transmission. In the example of FIG. 13B, each chirp increases in frequency from frequency $f_0$ to $f_1$ over an interval of 2 ns and each chirp is separated by 2 ns. In other embodiments, the chirps may be separated by very short intervals (e.g., a fraction of a nanosecond) or no interval.

FIG. 13C depicts a radar transmission technique that involves transmitting pulses of electromagnetic energy at the same frequency during a particular pulse but at an increased frequency from pulse-to-pulse, referred to herein as a "stepped frequency" transmission or a stepped frequency pattern. In the example of FIG. 13C, each pulse has a constant frequency over the interval of the pulse (e.g., over 2 ns), but the frequency increases by an increment of $\Delta f$ from pulse-to-pulse. For example, the frequency of the first pulse is $f_0$, the frequency of the second pulse is $f_0+\Delta f$, the frequency of the third pulse is $f_0+2\Delta f$, and the frequency of the fourth pulse is $f_0+3\Delta f$, and so on.

Figure 14:
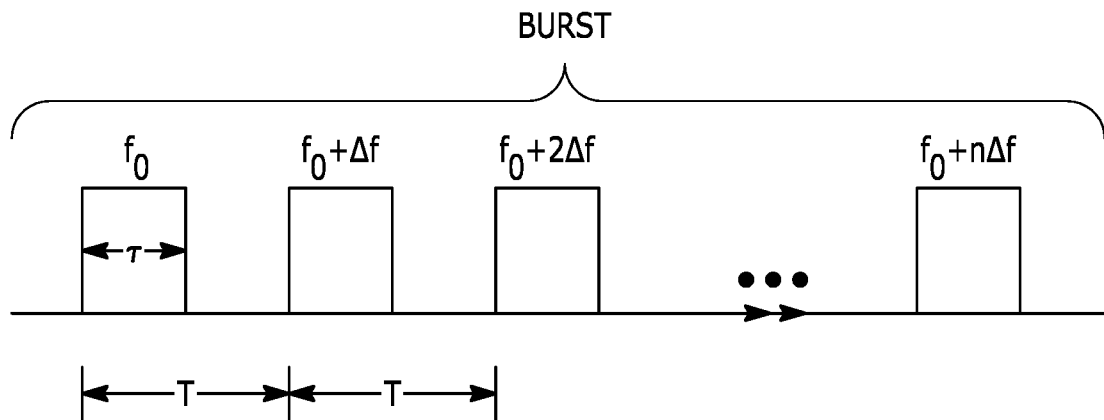
FIG. 14 depicts a burst of electromagnetic energy using stepped frequency transmission.

In an embodiment, the sensor system described herein is operated using stepped frequency transmission. Operation of the sensor system using stepped frequency transmission is described in more detail below. FIG. 14 depicts a burst of electromagnetic energy using stepped frequency transmission. The frequency of the pulses in the burst can be expressed as:

$$f_n = f_0 + n\Delta f$$

where $f_0$=starting carrier frequency, $\Delta f$=step size, $\tau$=pulse length (active, per frequency), T=repetition interval, n=1, ... N, each burst consists of N pulses (frequencies) and a coherent processing interval (CPI)=N·T=1 full burst.

Using stepped frequency transmission enables relatively high range resolution. High range resolution can be advantageous when trying to monitor a health parameter such as the blood glucose level in a vein that may, for example, have a diameter in the range of 1-4 mm. For example, in order to effectively isolate a signal that corresponds to reflections of electromagnetic energy from the blood in a 1-4 mm diameter vein, it is desirable to have a high range resolution, which is provided by the 122-126 GHz frequency range.

Using stepped frequency transmission, range resolution can be expressed as:

$$\Delta R = c/2B$$

wherein c=speed of light, B=effective bandwidth. The range resolution can then be expressed as:

$$\Delta R = c/2N\cdot\Delta f$$

wherein B=N·$\Delta f$. Thus, range resolution does not depend on instantaneous bandwidth and the range resolution can be increased arbitrarily by increasing N·$\Delta f$.

Figure 15A:
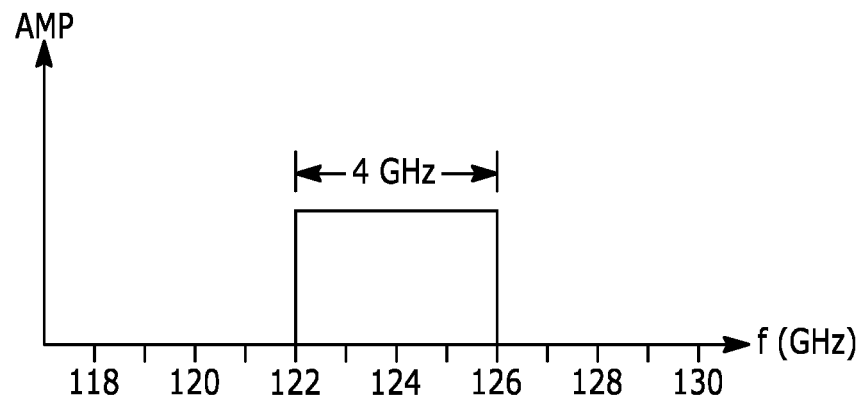
FIG. 15A depicts a graph of the transmission bandwidth, B, of transmitted electromagnetic energy in the frequency range of 122-126 GHz.
Figure 15B:
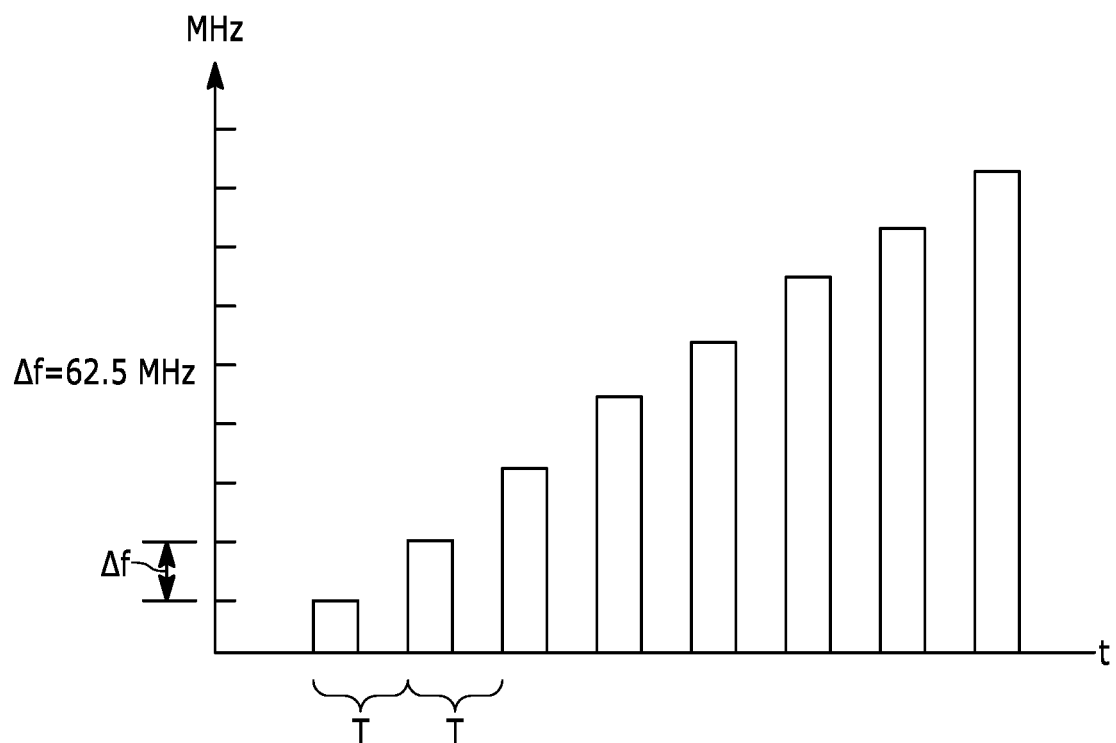
FIG. 15B depicts a graph of stepped frequency pulses that have a repetition interval, T, and a step size, $\Delta f$, of 62.5 MHz.

In an embodiment, the electromagnetic energy is transmitted from the TX antennas in the frequency range of approximately 122-126 GHz, which corresponds to a total bandwidth of approximately 4 GHz, e.g., B=4 GHz. FIG. 15A depicts a graph of the transmission bandwidth, B, of transmitted electromagnetic energy in the frequency range of 122-126 GHz. Within a 4 GHz bandwidth, from 122-126 GHz, discrete frequency pulses can be transmitted. For example, in an embodiment, the number of discrete frequencies that can be transmitted ranges from, for example, 64-256 discrete frequencies. In a case with 64 discrete frequency pulses and a repetition interval, T, over 4 GHz of bandwidth, the step size, $\Delta f$, is 62.5 MHz (e.g., 4 GHz of bandwidth divided by 64=62.5 MHz) and in a case with 256 discrete frequency pulses and a repetition interval, T, over 4 GHz of bandwidth, the step size, $\Delta f$, is 15.625 MHz (e.g., 4 GHz of bandwidth divided by 256=15.625 MHz). FIG. 15B depicts a graph of stepped frequency pulses that have a repetition interval, T, and a step size, $\Delta f$, of 62.5 MHz (e.g., 4 GHz of bandwidth divided by 64=62.5 MHz). As described above, an example sensor system has four RX antennas. Assuming a discrete frequency can be received on each RX antenna, degrees of freedom (DOF) of the sensor system in the receive operations can be expressed as: 4 RX antennas×64 discrete frequencies=256 DOF; and 4 RX antennas×256 discrete frequencies=1K DOF. The number of degrees of freedom (also referred to as "transmission frequency diversity") can provide signal diversity, which can be beneficial in an environment such as the anatomy of a person. For example, the different discrete frequencies may have different responses to the different anatomical features of the person. Thus, greater transmission frequency diversity can translate to greater signal diversity, and ultimately to more accurate health monitoring.

Figure 16A:
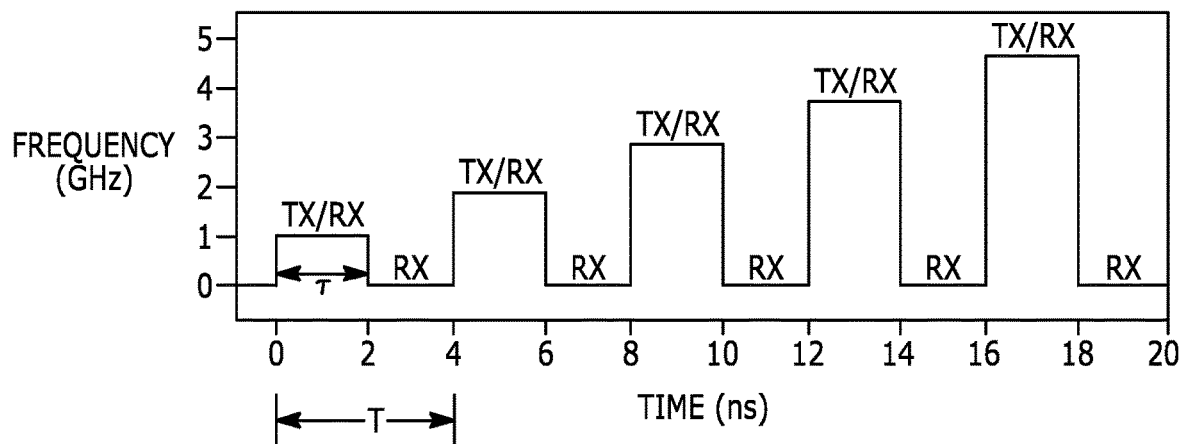
FIG. 16A depicts a frequency versus time graph of transmission pulses, with transmit (TX) interval and receive (RX) intervals identified relative to the pulses.
Figure 16B:
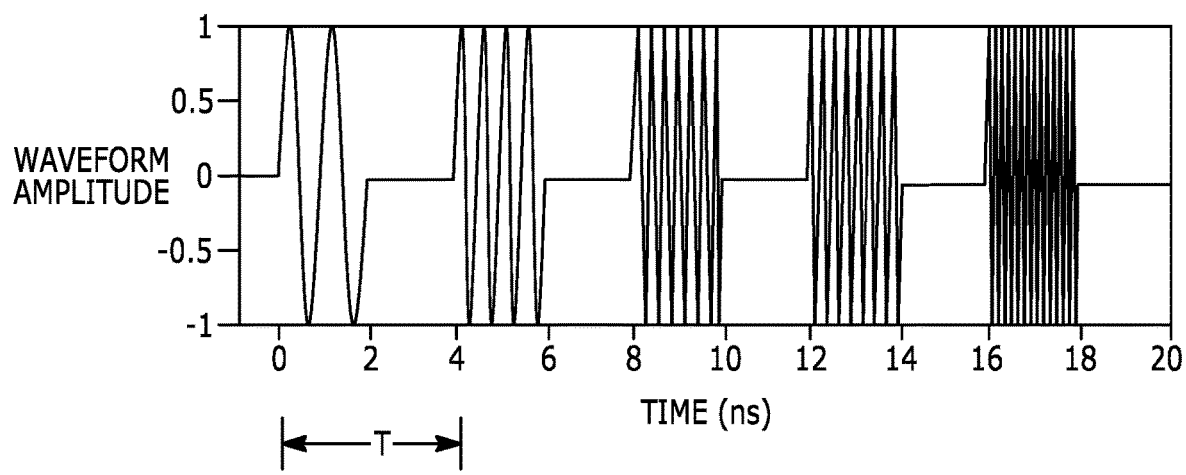
FIG. 16B depicts an amplitude versus time graph of the transmission waveforms that corresponds to FIG. 16A.

One feature of a stepped frequency transmission approach is that the sensor system receives reflected electromagnetic energy at basically the same frequency over the repetition interval, T. That is, as opposed to chirp transmission, the frequency of the pulse does not change over the interval of the pulse and therefore the received reflected electromagnetic energy is at the same frequency as the transmitted electromagnetic energy for the respective interval. FIG. 16A depicts a frequency versus time graph of transmission pulses, with transmit (TX) interval and receive (RX) intervals identified relative to the pulses. As illustrated in FIG. 16A, RX operations for the first pulse occur during the pulse length, τ, of repetition interval, T, and during the interval between the next pulse. FIG. 16B depicts an amplitude versus time graph of the transmission waveforms that corresponds to FIG. 16A. As illustrated in FIG. 16B, the amplitude of the pulses is constant while the frequency increases by Δf at each repetition interval, T.

In an embodiment, the power of the transmitted electromagnetic energy can be set to achieve a desired penetration depth and/or a desired illumination volume. In an embodiment, the transmission power from the TX antennas is about 15 dBm.

In an embodiment, electromagnetic energy can be transmitted from the TX antennas one TX antenna at a time (referred to herein as "transmit diversity"). For example, a signal is transmitted from a first one of the two TX antennas while the second one of the two TX antennas is idle and then a signal is transmitted from the second TX antenna while the first TX antenna is idle. Transmit diversity may reveal that illumination from one of the two TX antennas provides a higher quality signal than illumination from the other of the two TX antennas. This may be especially true when trying to illuminate a vein whose location may vary from person to person and/or from moment to moment (e.g., depending on the position of the wearable device relative to the vein). Thus, transmit diversity can provide sets of received signals that are independent of each other and may have different characteristics, e.g., signal power, SNR, etc.

Some theory related to operating the sensor system using a stepped frequency approach is described with reference to FIG. 17, which illustrates operations related to transmitting, receiving, and processing phases of the sensor system operation. With reference to the upper portion of FIG. 17, a time versus amplitude graph of a transmitted signal burst, similar to the graph of FIG. 16B, is shown. The graph represents the waveforms of five pulses of a burst at frequencies of $f_0$, $f_0+\Delta f$, $f_0+2\Delta f$, $f_0+3\Delta f$, and $f_0+4\Delta f$.

Figure 17:
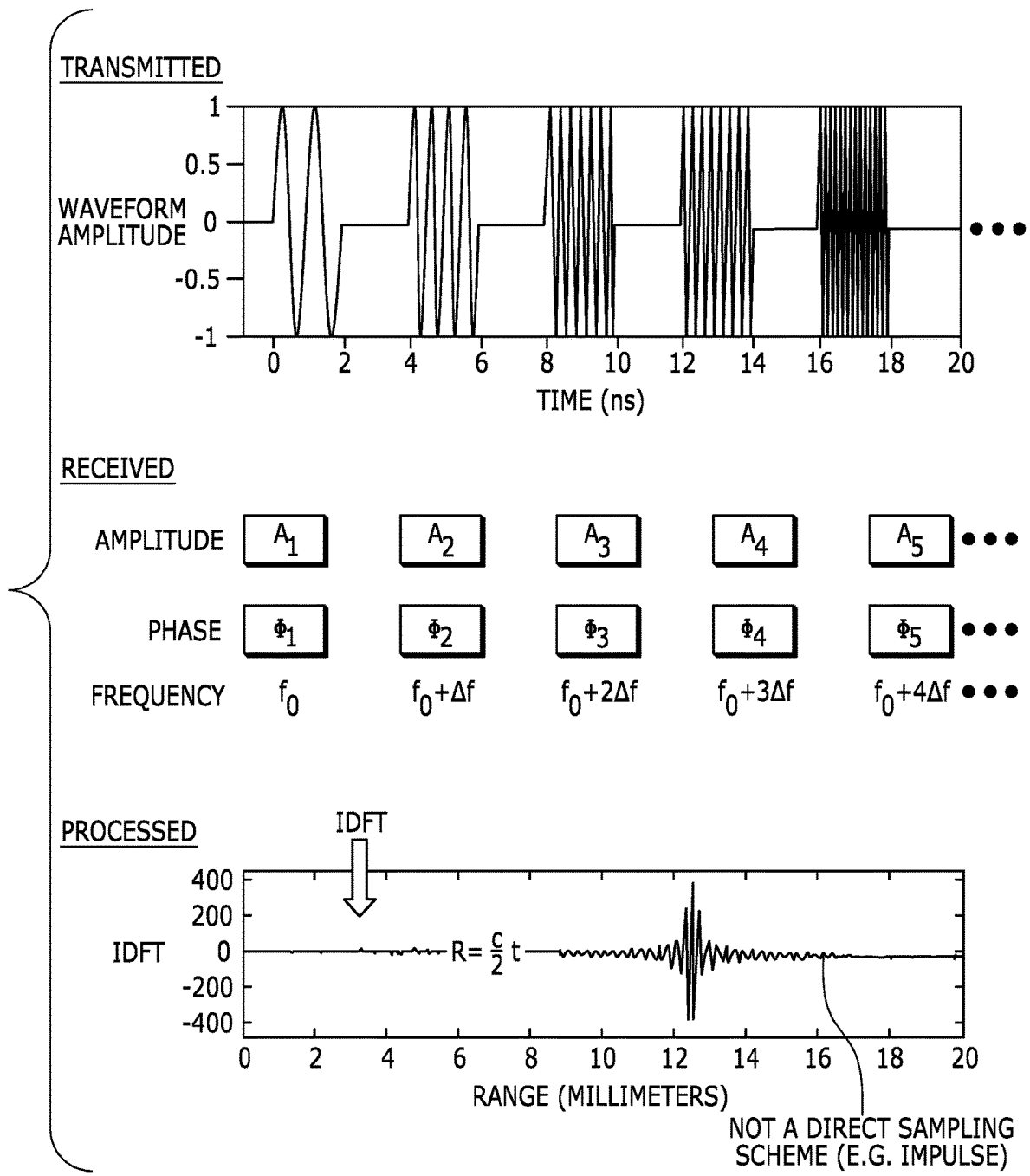
FIG. 17 illustrates operations related to transmitting, receiving, and processing phases of the sensor system operation.

The middle portion of FIG. 17 represents values of received signals that correspond to the amplitude, phase, and frequency of each pulse in the burst of four pulses. In an embodiment, received signals are placed in range bins such that there is one complex sample per range bin per frequency. Inverse Discrete Fourier Transforms (IDFTs) are then performed on a per-range bin basis to determine range information. The bottom portion of FIG. 17 illustrates an IDFT process that produces a signal that corresponds to the range of a particular object. For example, the range may correspond to a vein such as the basilic vein. In an embodiment, some portion of the signal processing is performed digitally by a DSP or CPU. Although one example of a signal processing scheme is described with reference to FIG. 17, other signal processing schemes may be implemented to isolate signals that correspond to reflections from blood in a vein (such as the basilic vein) from signals that correspond to reflections from other undesired anatomical features (such as tissue and bones) and from signals that correspond to leakage from the TX antennas.

Figure 18:
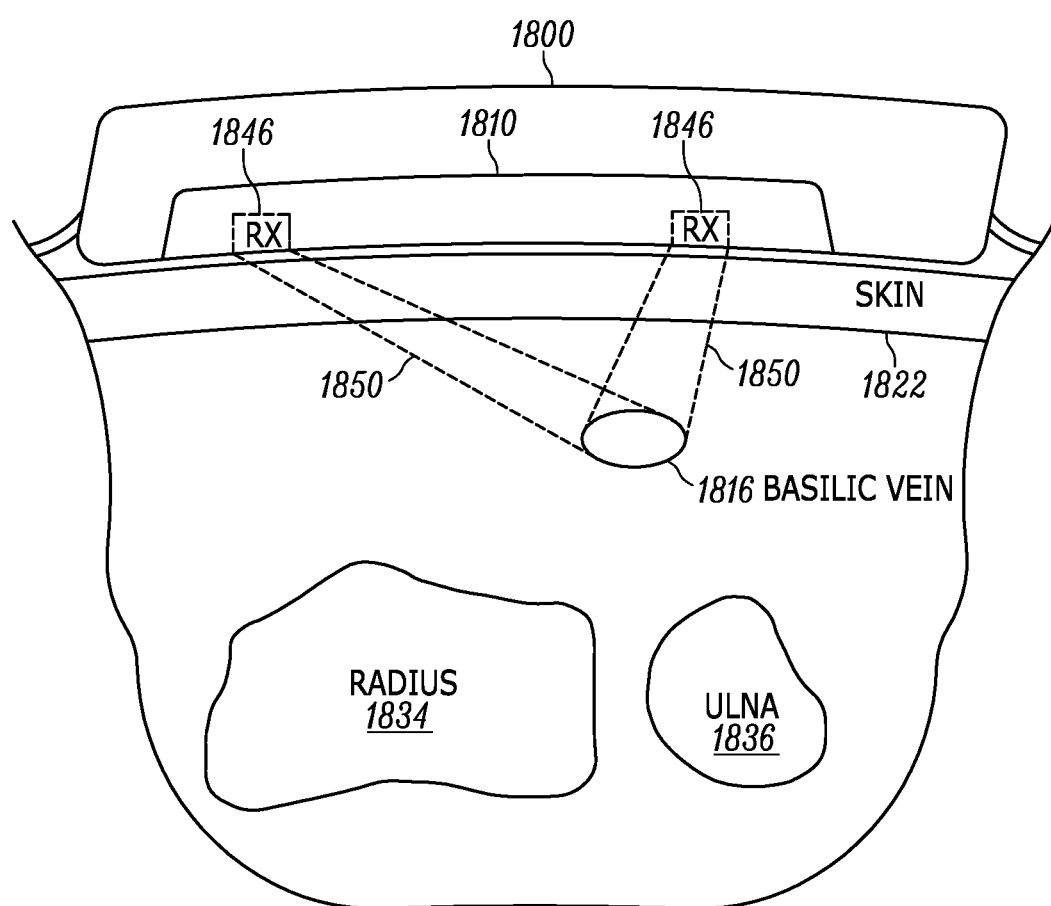
FIG. 18 depicts an expanded view of the anatomy of a wrist, similar to that described above with reference to FIGS. 2A-4D, relative to RX antennas of a sensor system that is integrated into a wearable device such as a smartwatch.

Beamforming is a signal processing technique used in sensor arrays for directional signal transmission and/or reception. Beamforming can be implemented by combining elements in a phased antenna array in such a way that signals at particular angles experience constructive interference while other signals experience destructive interference. Beamforming can be used in both transmit operations and receive operations in order to achieve spatial selectivity, e.g., to isolate some received signals from other received signals. In an embodiment, beamforming techniques are utilized to isolate signals that correspond to reflections from blood in a vein (such as the basilic vein) from signals that correspond to reflections from other undesired anatomical features (such as tissue and bones) and from signals that correspond to leakage from the TX antennas. An example of the concept of beamforming as applied to blood glucose monitoring using a wearable device such as a smartwatch is illustrated in FIG. 18. In particular, FIG. 18 depicts an expanded view of the anatomy of a wrist, similar to that described above with reference to FIGS. 2A-4D, relative to RX antennas 1846 of a sensor system 1810 that is integrated into a wearable device such as a smartwatch 1800. The anatomical features of the wrist that are illustrated in FIG. 18 include the skin 1822, a vein such as the basilic vein 1816, the radius bone 1834, and the ulna bone 1836. FIG. 18 also illustrates 2D representations of reception beams 1850 (although it should be understood that the beams occupy a 3D space/volume) that correspond to electromagnetic energy that is reflected from the blood in the basilic vein to the respective RX antenna.

In an embodiment, a beamforming technique involves near-field beamforming, where each RX antenna of the phased antenna array is steered independently to a different angle as opposed to far-field beamforming where all of the antennas in a phased antenna array are steered collectively to the same angle. For example, near-field beamforming is used when the target is less than about 4-10 wavelengths from the phased antenna array. In the case of a sensor system operating at 122-126 GHz, 4-10 wavelengths is approximately within about 10-25 mm from the phased antenna array. In the case of monitoring a health parameter related to blood, the blood vessels that are monitored (e.g., the basilic and/or cephalic veins) are likely to be less than 10-25 mm from the phase antenna array. Thus, in an embodiment, near-field beamforming techniques are used to isolate desired signals (e.g., signals that correspond to reflections from blood in a vein such as the basilic vein) from undesired signals (e.g., signals that correspond to reflections from other undesired anatomical features, such as tissue and bones, and from signals that correspond to leakage from the TX antennas). Beamforming can be accomplished in digital, in analog, or in a combination of digital and analog signal processing. In an embodiment, the ranging technique described above, which utilizes stepped frequencies, is used in combination with beamforming to isolate signals that correspond to the reflection of electromagnetic energy from the basilic vein.

The Doppler effect relates to the change in frequency or wavelength of a wave (e.g., an electromagnetic wave) in relation to an observer, which is moving relative to the source of the wave. The Doppler effect can be used to identify fluid flow by sensing the shift in wavelength of reflections from particles moving with the fluid flow. In accordance with an embodiment of the invention, signal processing based on the Doppler effect is applied to signals received by the sensor system to isolate signals that correspond to reflections from flowing blood from signals that correspond to reflections from objects that are stationary, at least with respect to the flowing blood. As described above, millimeter wave radio waves are transmitted below the skin to illuminate anatomical features below the skin. In the area of the body around the wrist, blood flowing through veins such as the basilic and cephalic veins is moving relative to the other anatomical features in the area. Thus, Doppler effect theory and corresponding signal processing is used to filter for those signals that correspond to movement (movement relative to other signals that correspond to stationary objects). In the health monitoring application as described herein, the signals that correspond to the flowing blood can be identified by applying the Doppler effect theory to the signal processing to isolate the signals that correspond to the flowing blood. The isolated signals can then be used to measure a health parameter such as blood glucose level.

Figure 19:
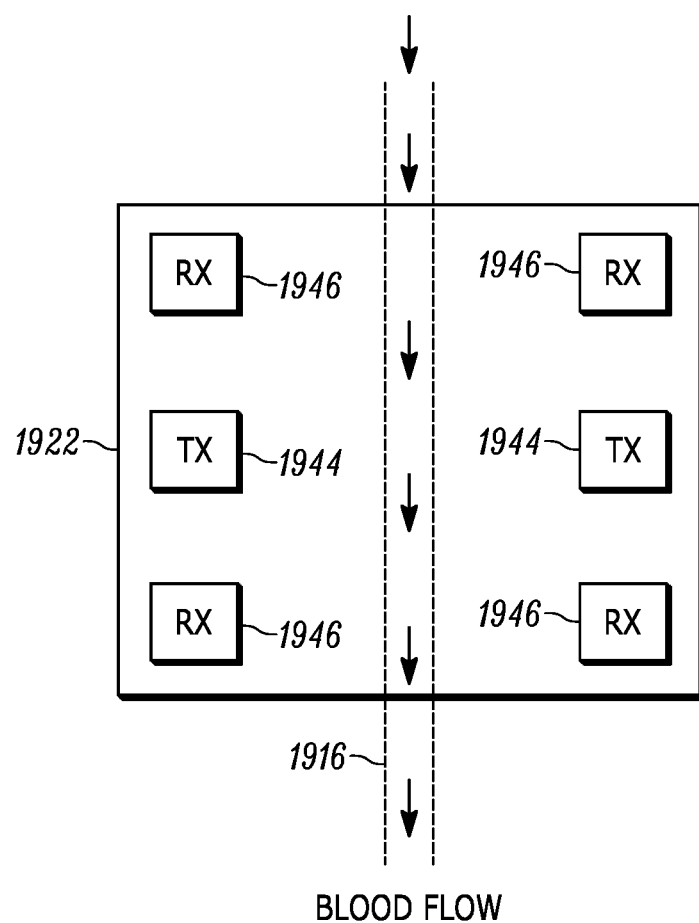
FIG. 19 illustrates an IC device similar to the IC device shown in FIG. 8A relative to a vein and blood flowing through the vein.

FIG. 19 illustrates an IC device 1922 similar to the IC device 822 shown in FIG. 8A relative to a vein 1916 such as the basilic or cephalic vein in the wrist area of a person. FIG. 19 also illustrates the flow of blood through the vein relative to the IC device. Because the blood is moving relative to the TX and RX antennas 1944 and 1946 of the sensor system, Doppler effect theory can be applied to signal processing of the received signals to isolate the signals that correspond to the flowing blood from the signals that correspond to objects that are stationary relative to the flowing blood. For example, received signals that correspond to flowing blood are isolated from received signals that correspond to stationary objects such as bone and fibrous tissue such as muscle and tendons. In an embodiment, Doppler processing involves performing a fast Fourier transform (FFT) on samples to separate the samples into component Doppler shift frequency bins. Frequency bins that represent no frequency shift can be ignored (as they correspond to reflections from stationary objects) and frequency bins that represent a frequency shift (which corresponds to reflections from a moving object) can be used to determine a health parameter. That is, Doppler effect processing can be used to isolate signals that represent no frequency shift (as they correspond to reflections from stationary objects) from frequency bins that represent a frequency shift (which correspond to reflections from a moving object). In an embodiment, Doppler effect signal processing may involve sampling over a relatively long period of time to achieve small enough velocity bins to decipher relative movement. Thus, Doppler effect theory and corresponding signal processing can be used to filter for only those signals that correspond to movement (movement relative to the other received signals). Such an approach allows signals that correspond to reflections from flowing blood, e.g., blood in a vein, to be isolated from other signals, e.g., signals that correspond to stationary object. In an embodiment, Doppler signal processing is performed digitally by a DSP and/or by a CPU.

With reference to FIG. 8A, during operation of the IC device 822, some electromagnetic energy that is emitted from the TX antennas 844 will be received directly by at least one of the RX antennas 846 without first passing through the skin of the person. Signals that correspond to such electromagnetic energy do not correspond to a health parameter that is to be monitored and are referred to herein as electromagnetic energy leakage or simply as "leakage." In an embodiment, various signal processing techniques may be implemented to mitigate the effects of leakage. For example, signals that correspond to leakage should be isolated from signals that correspond to reflections of radio waves from blood in a vein. In an embodiment, leakage is mitigated by applying signal processing to implement beamforming, Doppler effect processing, range discrimination or a combination thereof. Other techniques such as antenna design and antenna location can also be used to mitigate the effects of leakage.

Figure 20:
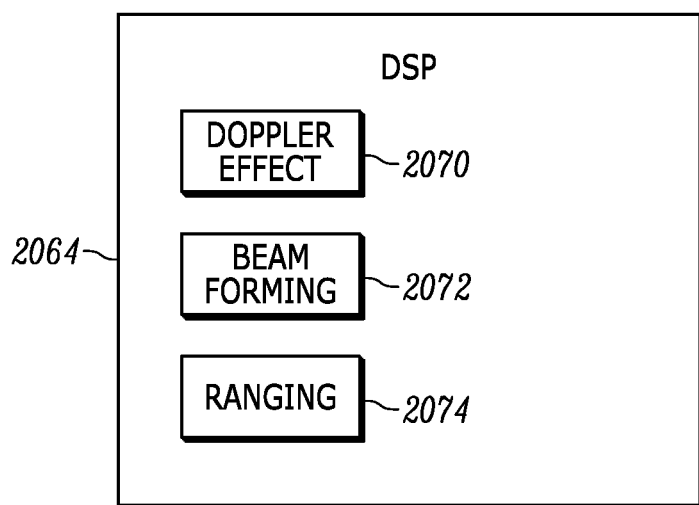
FIG. 20 is an embodiment of a DSP that includes a Doppler effect component, a beamforming component, and a ranging component.

In an embodiment, signal processing to isolate signals that correspond to reflections of radio waves from blood in a vein from signals that correspond to reflections of radio waves from other anatomical objects (such as bone and fibrous tissue such as muscle and tendons) and from signals that correspond to leakage can be implemented in part or in full digitally by a DSP. FIG. 20 is an embodiment of a DSP 2064 that includes a Doppler effect component 2070, a beamforming component 2072, and a ranging component 2074. In an embodiment, the Doppler effect component is configured to implement digital Doppler effect processing, the beamforming component is configured to implement digital beamforming, and the ranging component is configured to implement digital ranging. Although the DSP is shown as including the three components, the DSP may include fewer components and the DSP may include other digital signal processing capability. The DSP may include hardware, software, and/or firmware or a combination thereof that is configured to implement the digital signal processing that is described herein. In an embodiment, the DSP may be embodied as an ARM processor (Advanced RISC (reduced instruction set computing) Machine). In some embodiments, components of a DSP can be implemented in the same IC device as the RF front-end and the TX and RX antennas. In other embodiments, components of the DSP are implemented in a separate IC device or IC devices.

In an embodiment, the transmission of millimeter radio waves and the processing of signals that correspond to received radio waves is a dynamic process that operates to locate signals corresponding to the desired anatomy (e.g., signals that correspond to reflections of radio waves from a vein) and to improve the quality of the desired signals (e.g., to improve the SNR). For example, the process is dynamic in the sense that the process is an iterative and ongoing process as the location of the sensor system relative to a vein or veins changes.

Although the techniques described above are focused on monitoring the blood glucose level in a person, the disclosed techniques are also applicable to monitoring other parameters of a person's health such as, for example, blood pressure and heart rate. For example, the reflectively of blood in a vessel such as the basilic vein will change relative to a change in blood pressure. The change in reflectivity as monitored by the sensor system can be correlated to a change in blood pressure and ultimately to an absolute value of a person's blood pressure. Additionally, monitored changes in blood pressure can be correlated to heart beats and converted over time to a heart rate, e.g., in beats per minute. In other embodiments, the disclosed techniques can be used to monitor other parameters of a person's health that are affected by the chemistry of the blood. For example, the disclosed techniques may be able to detect changes in blood chemistry that correspond to the presence of foreign chemicals such as alcohol, narcotics, cannabis, etc. The above-described techniques may also be able to monitor other parameters related to a person, such as biometric parameters.

In an embodiment, health monitoring using the techniques described above, may involve a calibration process. For example, a calibration process may be used for a particular person and a particular monitoring device to enable desired monitoring quality.

The above-described techniques are used to monitor a health parameter (or parameters) related to blood in a blood vessel or in blood vessels of a person. The blood vessels may include, for example, arteries, veins, and/or capillaries. The health monitoring technique can target blood vessels other than the basilic and/or cephalic veins. For example, other near-surface blood vessels (e.g., blood vessels in the subcutaneous layer) such as arteries may be targeted. Additionally, locations other than the wrist area can be targeted for health monitoring. For example, locations in around the ear may be a desirable location for health monitoring, including, for example, the superficial temporal vein and/or artery and/or the anterior auricular vein or artery. In an embodiment, the sensor system may be integrated into a device such as a hearing aid or other wearable device that is attached to the ear or around or near the ear. In another embodiment, locations in and around the elbow joint of the arm may be a desirable location for health monitoring. For example, in or around the basilica vein or the cephalic vein at or near the elbow.

Although the techniques are described as using a frequency range of 122-126 GHz, some or all of the above-described techniques may be applicable to frequency ranges other than 122-126 GHz. For example, the techniques may be applicable to frequency ranges around 60 GHz. In another embodiment, the techniques described herein may be applicable to the 2-6 GHz frequency range. For example, a system similar to that described with reference to FIG. 6 may be used to implement health monitoring by transmitting and receiving RF energy in the 2-6 GHz range. In still another embodiment, multiple non-contiguous frequency ranges may be used to implement health monitoring. For example, health monitoring may be implemented using both the 2-6 GHz frequency range and the 122-126 GHz frequency range. For example, in an embodiment, stepped frequency scanning in implemented in the lower frequency range and then in the higher frequency range, or vice versa. Using multiple non-contiguous frequency ranges (e.g., both the 2-6 GHz frequency range and the 122-126 GHz frequency range) may provide improved accuracy of health monitoring.

In an embodiment, the sensor system may be embedded into a different location in a monitoring device. For example, in an embodiment, a sensor system (or a portion of the sensor system such as IC device as shown in FIG. 8A) is embedded into an attachment device such as the strap of a smartwatch so that the sensor system can target a different blood vessel in the person. For example, the sensor system may be embedded into the strap of a smartwatch so that a blood vessel at the side area of the wrist and/or at the anterior area of the wrist can be monitored. In such an embodiment, the strap may include conductive signal paths that communicate signals between the sensor IC device and the processor of the smartwatch.

Figure 21:
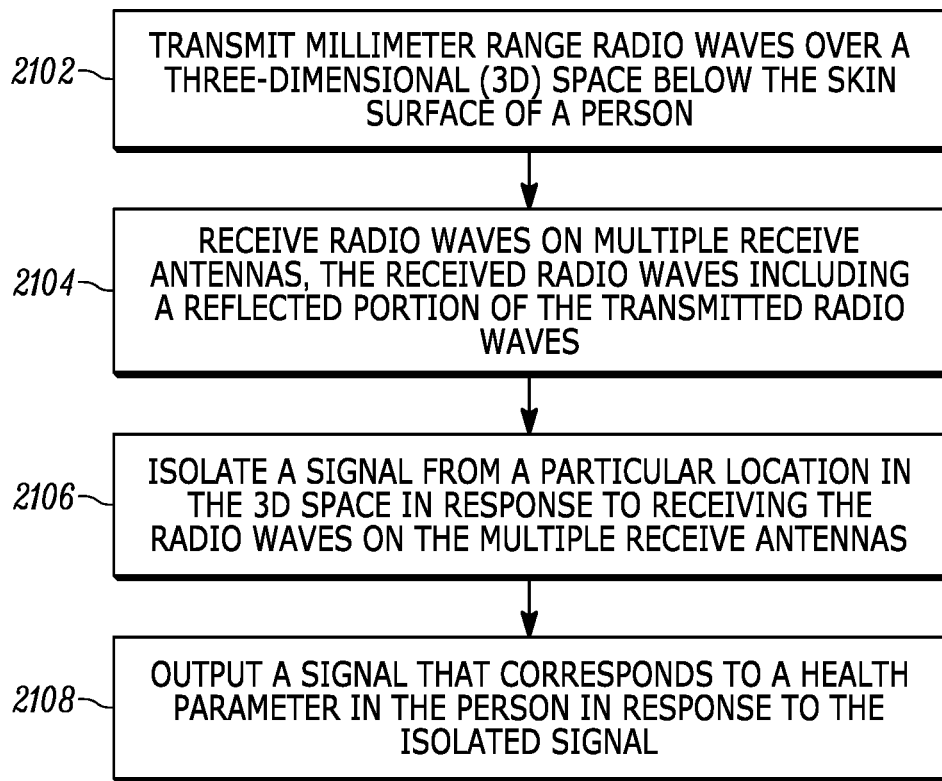
FIG. 21 is a process flow diagram of a method for monitoring a health parameter in a person.

FIG. 21 is a process flow diagram of a method for monitoring a health parameter in a person. At block 2102, millimeter range radio waves are transmitted over a three-dimensional (3D) space below the skin surface of a person. At block 2104, radio waves are received on multiple receive antennas, the received radio waves including a reflected portion of the transmitted radio waves. At block 2106, a signal is isolated from a particular location in the 3D space in response to receiving the radio waves on the multiple receive antennas. At block 2108, a signal that corresponds to a health parameter in the person is output in response to the isolated signal. In an embodiment, the health parameter is blood glucose level. In other embodiments, the health parameter may be blood pressure or heart rate.

In an embodiment, health monitoring information that is gathered using the above-described techniques can be shared. For example, the health monitoring information can be displayed on a display device and/or transmitted to another computing system via, for example, a wireless link.

Figure 22A:
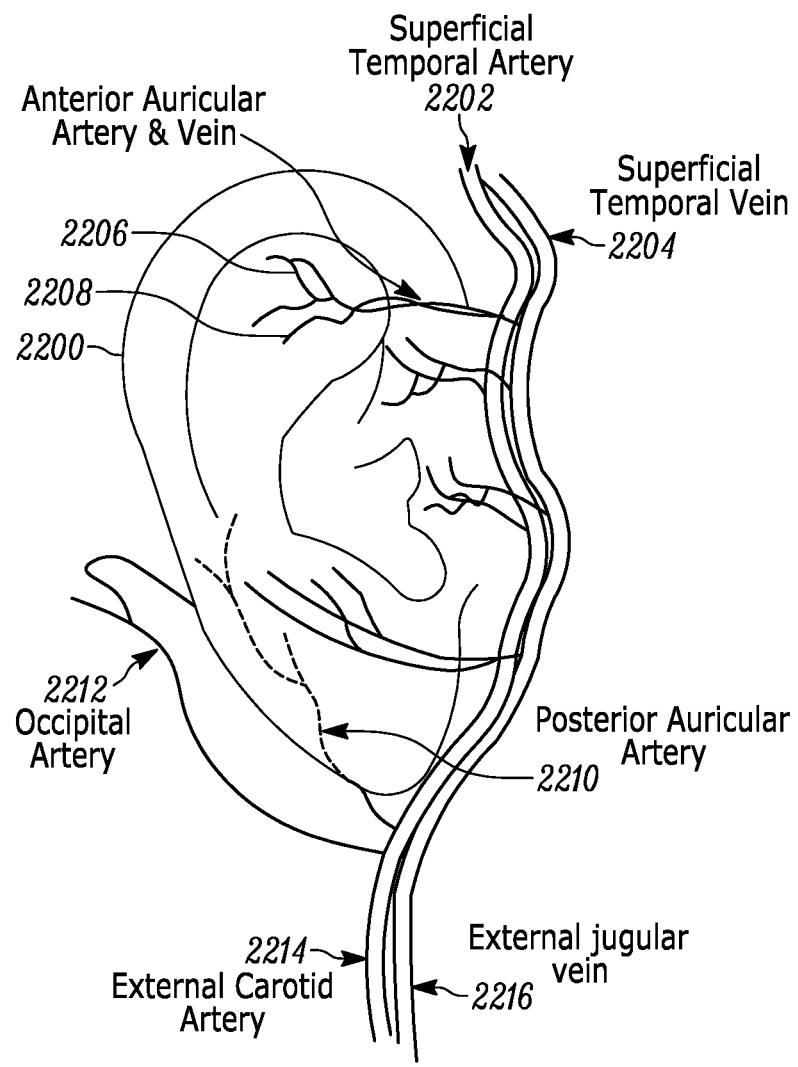
FIG. 22A depicts a side view of the area around a person's ear with the typical approximate locations of veins and arteries, including the superficial temporal artery, the superficial temporal vein, the anterior auricular artery and vein, the posterior auricular artery, the occipital artery, the external carotid artery, and the external jugular vein.
Figure 22B:
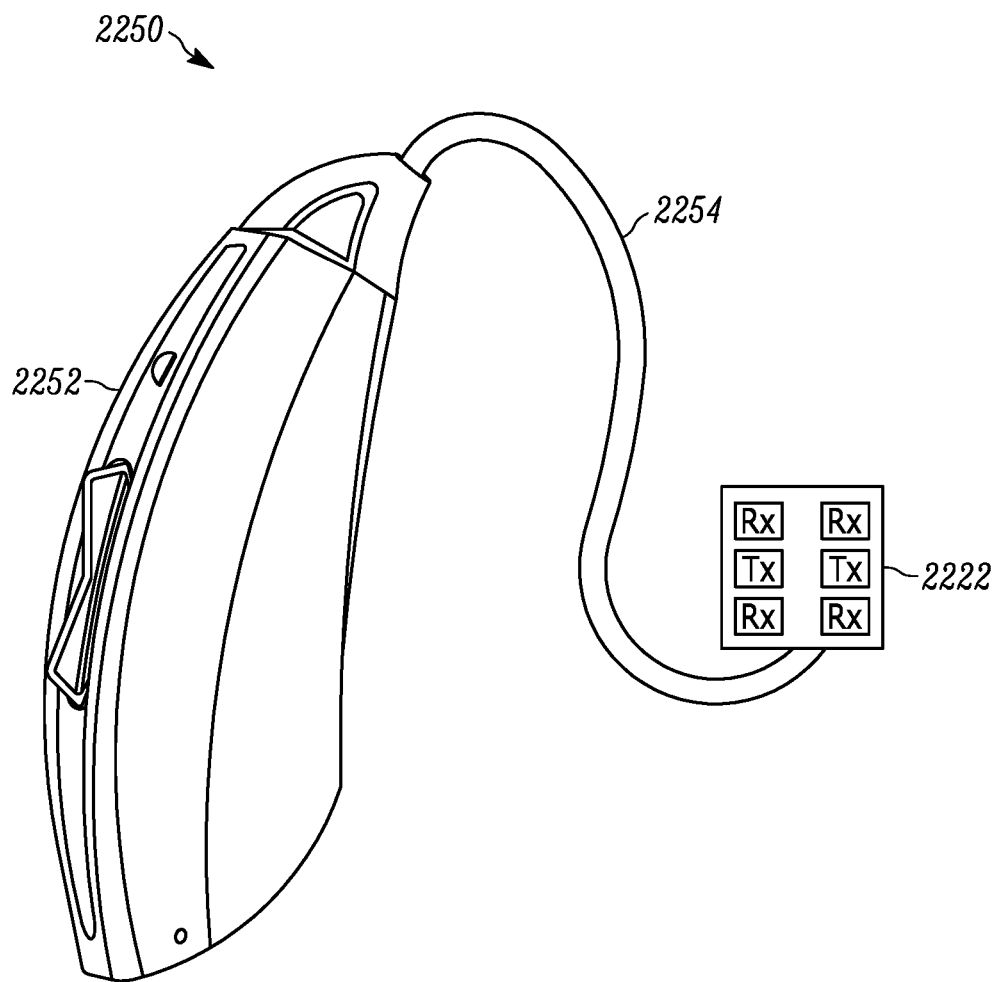
FIG. 22B depicts an embodiment of system in which at least elements of an RF front-end are located separate from a housing.
Figure 22C:
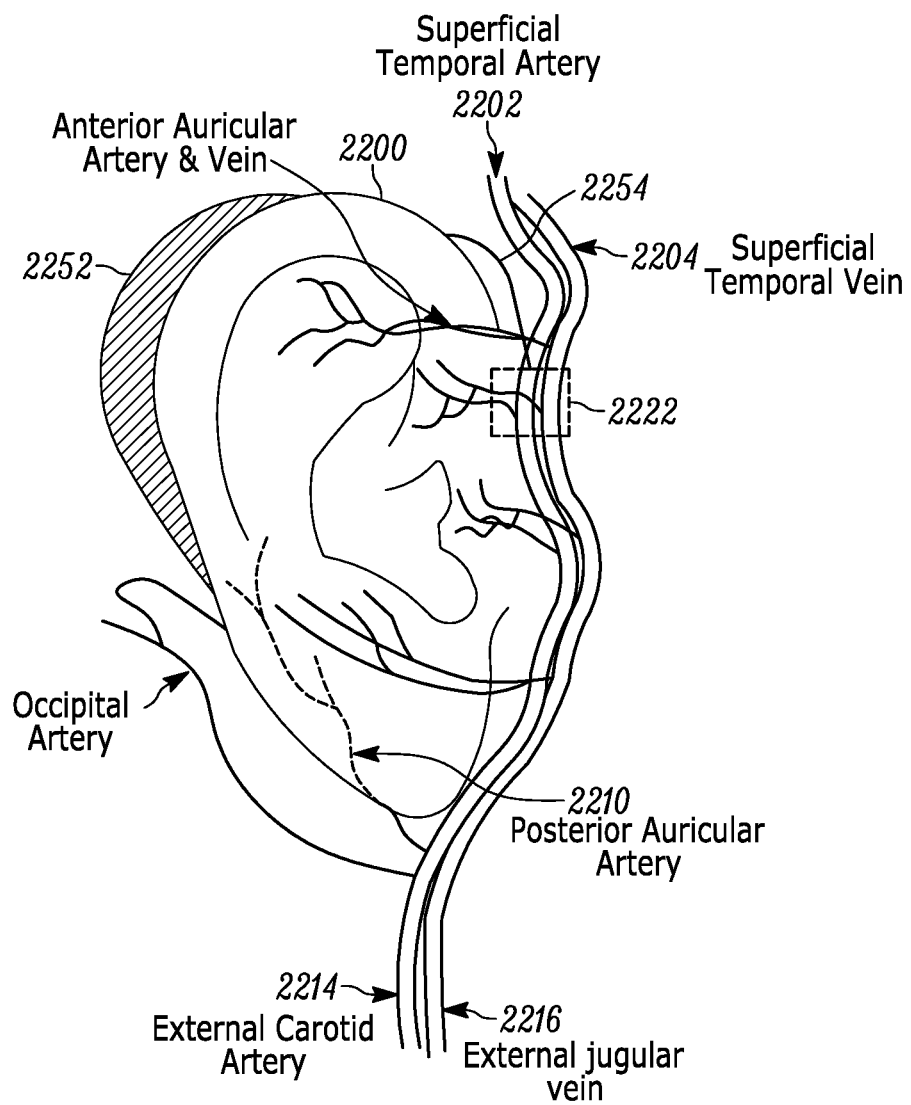
FIG. 22C illustrates how a device, such as the device depicted in FIG. 22B, may be worn near the ear of a person similar to how a conventional hearing aid is worn.

As mentioned above, locations in around the ear may be desirable for health monitoring, including, for example, the superficial temporal artery or vein, the anterior auricular artery or vein, and/or the posterior auricular artery. FIG. 22A depicts a side view of the area around a person's ear 2200 with the typical approximate locations of veins and arteries, including the superficial temporal artery 2202, the superficial temporal vein 2204, the anterior auricular artery 2206 and vein 2208, the posterior auricular artery 2210, the occipital artery 2212, the external carotid artery 2214, and the external jugular vein 2216. In an embodiment, a sensor system, such as the sensor system described herein, may be integrated into a device such as a hearing aid or another wearable device that is attached to the ear or around or near the ear. FIG. 22B depicts an embodiment of system 2250 in which at least elements of an RF front-end 2222 (including the transmit and receive antennas and corresponding transmit and receive components as shown in FIGS. 5-7) are located separate from a housing 2252 that includes, for example, a digital processor, wireless communications capability, and a source of electric power, all of which are enclosed within the housing. For example, components of the digital baseband system as shown in FIG. 5 may be enclosed within the housing and the housing is connected to the RF front-end by a communications medium 2254, such as a conductive wire or wires. In an embodiment, the housing 2252 is worn behind the ear 2200 similar to a conventional hearing aid and the RF front-end 2222 is located near a blood vessel that is around the ear. For example, the RF front-end may include adhesive material that enables the RF front-end to be adhered to the skin near a blood vessel such as, for example, the superficial temporal artery 2202 or vein 2204, the anterior auricular artery 2206 or vein 2208, and/or the posterior auricular artery 2210. FIG. 22C illustrates how a device, such as the device depicted in FIG. 22B, may be worn near the ear 2200 of a person similar to how a conventional hearing aid is worn. FIG. 22C also shows the RF front-end 2222 relative to the superficial temporal artery 2202 and the superficial temporal vein 2204 as shown in FIG. 22C. In an embodiment, the sensor system may be integrated with a conventional hearing aid to provide both hearing assistance and health monitoring. For example, the integrated system may include a housing, a speaker that is inserted into the ear, and an RF front-end that is attached to the skin around the ear and near to a blood vessel. In other embodiments, a sensor system may be integrated into ear buds or into some other type of device that is worn around or near the ear.

Although the magnitude of the reflected RF energy (also referred to as amplitude) that is received by the sensor system has been found to correspond to a health parameter, such as blood glucose level, it has further been found that the combination of the amplitude and the phase of the reflected RF energy can provide improved correspondence to a health parameter, such as a blood glucose level. Thus, in an embodiment, a value that corresponds to a health parameter of a person is generated in response to amplitude and phase data that is generated in response to received radio waves.

For example, the value that corresponds to a health parameter may be a value that indicates a blood glucose level in mg/dL or some other indication of the blood glucose level, a value that indicates a person's heart rate (e.g., in beats per minute), and/or a value that indicates a person's blood pressure (e.g., in millimeters of mercury, mmHg). In an embodiment, a method for monitoring a health parameter (e.g., blood glucose level) in a person involves transmitting radio waves below the skin surface of a person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data across the range of stepped frequencies, and determining a value that is indicative of a health parameter in the person in response to the amplitude and phase data. In an embodiment, the phase data corresponds to detected shifts in sine waves that are received at the sensor system. In another embodiment, a value that is indicative of a health parameter in the person may be determined in response to phase data but not in response to amplitude data.

Additionally, it has been found that certain step sizes in stepped frequency scanning can provide good correspondence in health parameter monitoring. In an embodiment, the frequency range that is scanned using stepped frequency scanning is on the order of 100 MHz in the 122-126 GHz range and the step size is in the range of 100 kHz-1 MHz. For example, in an embodiment, the step size over the scanning range is around 100 kHz (±10%).

Although the amplitude and phase of the reflected RF energy that is received by the sensor system has been found to correspond to a health parameter, such as blood glucose level, it has further been found that the combination of the amplitude and phase of the reflected RF energy and some derived data, which is derived from the amplitude and/or phase data, can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data derived from the amplitude and/or phase data may include statistical data such as the standard deviation of the amplitude over a time window and/or the standard deviation of the phase over a time window. In an embodiment, data can be derived from the raw data on a per-receive antenna basis or aggregated amongst the set of receive antennas. In a particular example, it has been found that the amplitude, phase, and the standard deviation of amplitude over a time window (e.g., a time window of 1 second) corresponds well to blood glucose levels.

In an embodiment, a method for monitoring a health parameter (e.g., blood glucose level) in a person involves transmitting radio waves below the skin surface of the person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data, deriving data from at least one of the amplitude and phase data, and determining a value that is indicative of a health parameter in the person in response to the derived data. In an embodiment, the value is determined in response to not only the derived data but also in response to the amplitude data and the phase data. In an embodiment, the derived data is a statistic that is derived from amplitude and/or phase data that is generated over a time window. For example, the statistic is one of a standard deviation, a moving average, and a moving mean. In other embodiments, the derived data may include multiple statistics derived from the amplitude and/or phase data. In an embodiment, a value that is indicative of a health parameter is determined in response to a rich set of parameters associated with the stepped frequency scanning including the scanning frequency, the detected amplitudes and phases of the received RF energy, data derived from the detected amplitudes and phases, the state of the transmit components, and the state of the receive components.

Using a sensor system, such as the sensor system described above, there are various parameters to be considered in the stepped frequency scanning process. Some parameters are fixed during operation of the sensor system and other parameters may vary during operation of the sensor system. Of the parameters that may vary during operation of the sensor system, some may be controlled and others are simply detected. FIG. 23 is a table of parameters related to stepped frequency scanning in a system such as the above-described system. The table includes an identification of various parameters and an indication of whether the corresponding parameter is fixed during operation (e.g., fixed as a physical condition of the sensor system) or variable during operation and if the parameter is variable, whether the parameter is controlled, or controllable, during operation or simply detected during operation. In the table of FIG. 23, "Time" refers to an aspect of time such as an absolute moment in time relative to some reference (or may refer to a time increment, e.g., $\Delta t$). In an embodiment, the time corresponds to all of the other parameters in the table. That is, the state or value of all of the other parameters in the table is the state or value at that time in the stepped frequency scanning operation. "TX/RX frequency" refers to the transmit/receive frequency of the sensor system at the corresponding time as described above with reference to, for example, FIG. 6. The TX1 and TX2 state refers to the state of the corresponding transmitter (e.g., whether or not the corresponding power amplifiers (PAs) are on or off) at the corresponding time. In an embodiment, RF energy transmitted from the transmission antennas can be controlled by activating/deactivating the corresponding PAs. The RX1 and RX2 state refers to the state of the corresponding receive paths (e.g., whether or not components of the corresponding receive paths are active or inactive, which may involve powering on/off components in the receive path) at the corresponding time. In an embodiment, the receiving of RF energy on the receive paths can be controlled by activating/deactivating components of the corresponding receive paths. The RX detected amplitude refers to the amplitude of the received signals at the corresponding receive path and at the corresponding time and the RX detected phase refers to the phase (or phase shift) of the received signals at the corresponding receive path and at the corresponding time. The TX and RX antenna 2D position refers to information about the 2D position of the antennas in the sensor system (e.g., the positions of the antennas relative to each other or the positions of the antennas relative to a common location) and the antenna orientation refers to antenna characteristics that may be specific to a particular polarization orientation. For example, a first set of antennas may be configured for vertical polarization while a second set of antennas is configured for horizontal polarization in order to achieve polarization diversity. Other antenna orientations and/or configurations are possible. As indicated in the table, antenna position and antenna orientation are fixed during stepped frequency scanning.

Figure 25:
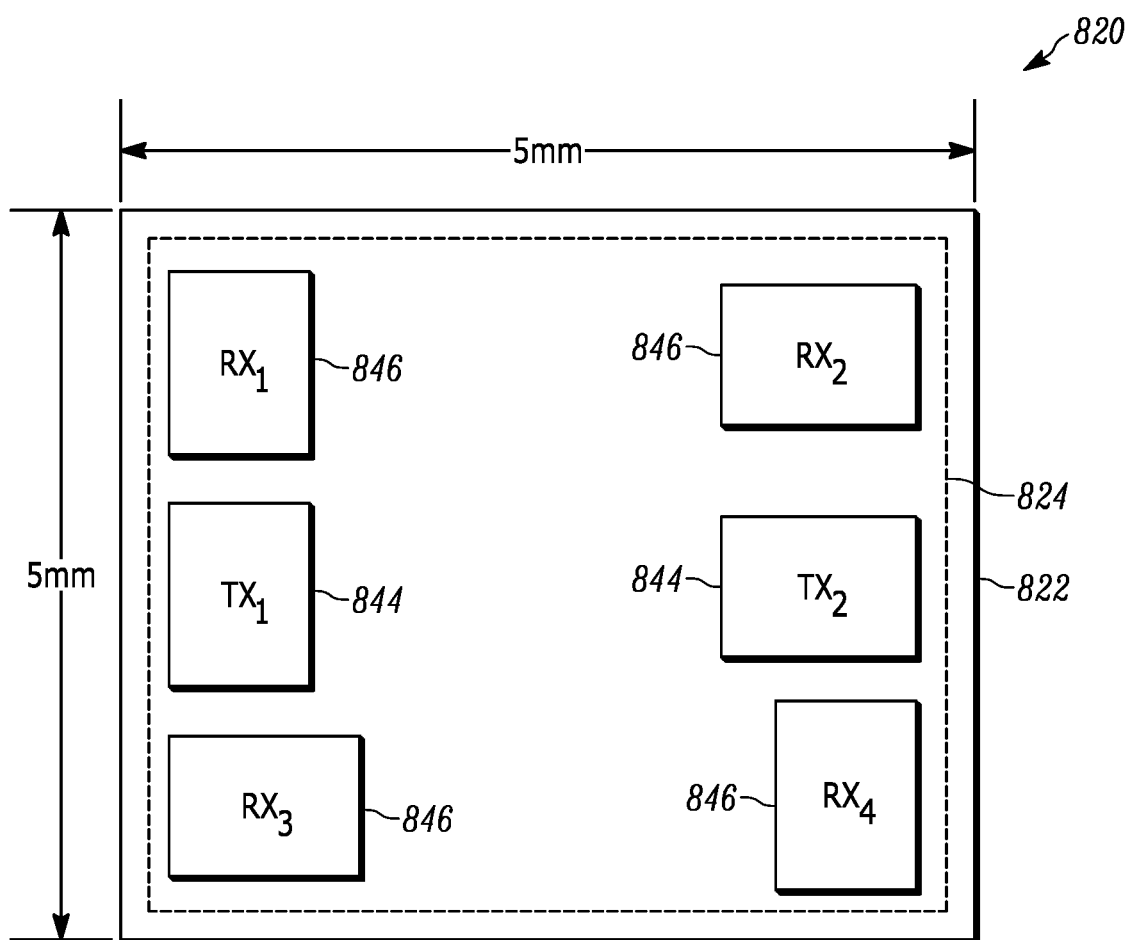
FIG. 25 depicts an embodiment of the IC device from FIG. 8A in which the antenna polarization orientation is illustrated by the orientation of the transmit and receive antennas.

FIG. 24 is a table of parameters similar to the table of FIG. 23 in which examples are associated with each parameter for a given step in a stepped frequency scanning operation in order to give some context to the table. As indicated in FIG. 24, the time is "t1" (e.g., some absolute time indication or a time increment) and the operating frequency is "X GHz," e.g., in the range of 2-6 GHz or 122-126 GHz. In the example of FIG. 24, TX1, RX1, and RX4 are active and TX2, RX2, and RX3 are inactive during this step in the stepped frequency scanning operation (e.g., at time t1). The detected amplitudes of RX1 and RX4 are indicated as "ampl1" and "ampl4" and the detected phases of RX1 and RX4 are indicated as "ph1" and "ph4." The detected amplitudes and phases of RX2 and RX3 are indicated as "n/a" since the receive paths are inactive. The positions of the transmit and receive antennas are indicated in the lower portion of the table and correspond to the configuration described above with reference to FIGS. 8A-8D and the antenna orientations are evenly distributed amongst vertical and horizontal orientations so as to enable polarization diversity. FIG. 25 depicts an embodiment of the IC device 820 from FIG. 8A in which the antenna polarization orientation is illustrated by the orientation of the transmit and receive antennas 844 and 846, respectively. In FIG. 25, rectangles with the long edges oriented vertically represent a vertical polarization orientation (e.g., antennas TX1, RX1, and RX4) and rectangles with the long edges oriented horizontally represent a horizontal polarization orientation (e.g., antennas TX2, RX2, and RX3). FIG. 24 reflects the same polarization orientations in which TX1 is configured to vertically polarize the transmitted RF energy and RX1 and RX4 are configured to receive vertically polarized RF energy and TX2 is configured to horizontally polarize the transmitted RF energy and RX2 and RX3 are configured to receive horizontally polarized RF energy. Although FIG. 24 is provided as an example, the parameter states of the variable parameters are expected to change during stepped frequency scanning and the fixed parameters may be different in different sensor system configurations.

In an embodiment, during a stepped frequency scanning operation, certain data, referred to herein as "raw data," is generated. For example, the raw data is generated as digital data that can be further processed by a digital data processor. FIG. 26 is a table of raw data (e.g., digital data) that is generated during stepped frequency scanning. The raw data depicted in FIG. 26 includes variable parameters of time, TX/RX frequency, RX1 amplitude/phase, RX2 amplitude/phase, RX3 amplitude/phase, and RX4 amplitude/phase. In the example of FIG. 26, the raw data corresponds to a set of data, referred to as a raw data record, which corresponds to one step in the stepped frequency scanning. For example, the raw data record corresponds to a particular frequency pulse as shown and described above with reference to FIG. 17. In an embodiment, a raw data record also includes some or all of the parameters identified in FIGS. 23 and 24. For example, the raw data record may include other variable and/or fixed parameters that correspond to the stepped frequency scanning operation. In an embodiment, multiple raw data records are accumulated and processed by a digital processor, which may include a DSP, an MCU, and/or a CPU as described above, for example, with reference to FIG. 5. Raw data (e.g., in the form of raw data records) may be used for machine learning.

As described above, it has been found that the combination of the amplitude and phase of reflected RF energy and some derived data, which is derived from amplitude and/or phase data (e.g., from the "raw data"), can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data is derived from the raw data records that include the data depicted in FIGS. 23, 24, and 26. For example, raw data records are accumulated over time and statistical data is derived from the accumulated raw data records. The statistical data, typically along with at least some portion of the raw data, is then used to determine a value of a health parameter of a person.

Although it has been found that derived data from the amplitude and/or phase data can provide improved correspondence to a health parameter, such as blood glucose level, the particular model that provides a desired level of correspondence (e.g., that meets a predetermined accuracy) may need to be learned in response to a specific set of operating conditions. Thus, in an embodiment, a learning process (e.g., machine learning) is implemented to identify and train a model that provides an acceptable correspondence to a health parameter such as blood glucose level.

Figure 27:
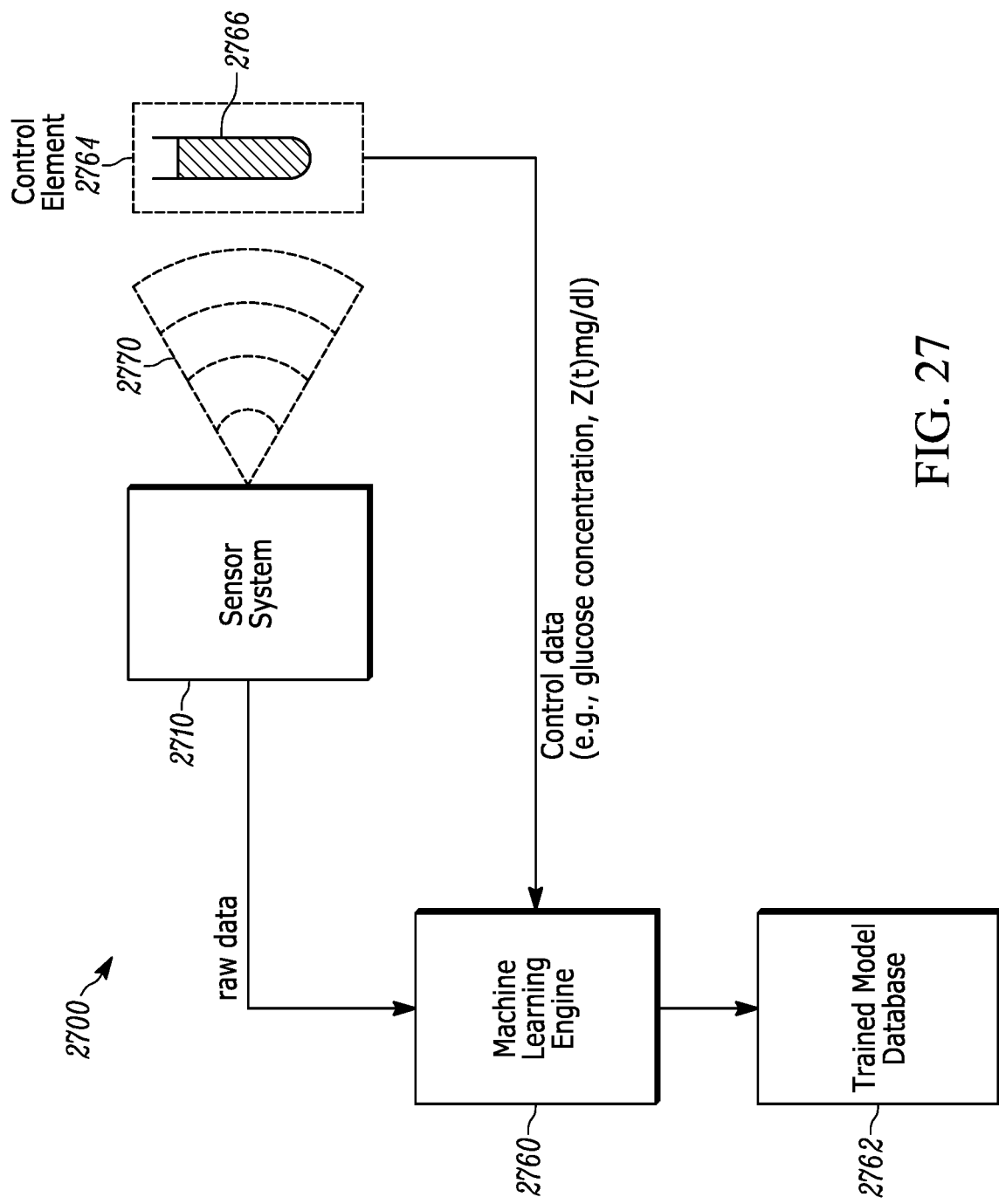
FIG. 27 illustrates a system and process for machine learning that can be used to identify and train a model that reflects correlations between raw data, derived data, and control data.

FIG. 27 illustrates a system 2700 and process for machine learning that can be used to identify and train a model that reflects correlations between raw data, derived data, and control data. For example, the machine learning process may be used to identify certain statistics (e.g., standard deviation of amplitude and/or phase over time) that can be used to improve the correspondence of determined values to actual health parameters (such as blood glucose levels) in a person. The machine learning process can also be used to train a model with training data so that the trained model can accurately and reliably determine values for health parameters such as blood glucose level, blood pressure, and/or heart rate in monitoring devices that are deployed in the field. With reference to FIG. 27, the system 2700 includes a sensor system 2710, a machine learning engine 2760, a trained model database 2762, and a control element 2764.

In an embodiment, the sensor system 2710 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the machine learning engine that can be accumulated and used as described below.

In an embodiment, the control element 2764 is configured to provide a control sample to the sensor system 2710. For example, the control element includes a sample material 2766 (e.g., a fluid) that has a known blood glucose level that is subjected to the sensor system. Additionally, in an embodiment, the control element is configured to provide control data to the machine learning engine that corresponds to the sample material. For example, the control element may include a sample material that has a known blood glucose level that changes as a function of time and the change in blood glucose level as a function of time (e.g., Z(t) mg/dL) is provided to the machine learning engine 2760 in a manner in which the raw data from the sensor system 2710 and the control data can be time matched (e.g., synchronized). In another embodiment, the control element 2764 includes a sample material that includes a static parameter, e.g., a static blood glucose level in mg/dL, and the static parameter is manually provided to the machine learning engine 2760 as the control data. For example, a particular sample is provided within range of RF energy 2770 that is transmitted from the sensor system (e.g., within a few millimeters), the concentration of the sample is provided to the machine learning engine (e.g., manually entered), and the sensor system accumulates digital data that corresponds to the received RF energy (including a reflected portion of the transmitted RF energy) and that is correlated to the sample. In one embodiment, the sample material is provided in a container such as a vial and in another embodiment, the control element includes a person that is simultaneously being monitored by the sensor system (e.g., for the purposes of machine learning) and by a second, trusted, control monitoring system. For example, the control element includes a person who's blood glucose level, blood pressure, and/or heart rate is being monitored by a known (e.g., clinically accepted) blood glucose level, blood pressure, and/or heart rate monitor while the person is simultaneously being monitored by the sensor system. The blood glucose level, blood pressure, and/or heart rate information from the known blood glucose level, blood pressure, and/or heart rate monitor is provided to the machine learning engine as control data.

In an embodiment, the machine learning engine 2760 is configured to process the raw data received from the sensor system 2710, e.g., as raw data records, and the control data received from the control element 2764 to learn a correlation, or correlations, that provides acceptable correspondence to a health parameter such as blood glucose levels. For example, the machine learning engine is configured to receive raw data from the sensor system, to derive data from the raw data such as statistical data, and to compare the derived data (and likely at least some portion of the corresponding raw data) to the control data to learn a correlation, or correlations, that provides acceptable correspondence between a determined value of a health parameter and a controlled, or known value, of the health parameter. In an embodiment, the machine learning engine is configured to derive statistics from the raw data such as a standard deviation, a moving average, and a moving mean. For example, the machine learning engine may derive the standard deviation of the amplitude and/or phase of the received RF energy and then correlate the derived statistic(s) and the raw data to the control data to find a correlation that provides an acceptable correspondence between the raw data, the derived data, and the actual value of the health parameter as provided in the control data. In an embodiment, correspondence between the raw data, the derived data, and the actual values of the health parameter in a control sample is expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set to accept only those correlations that produce correspondence that meets a desired correspondence threshold. In an embodiment, a correspondence threshold of a generated value to the value of a control sample of within ±10% of the control sample is acceptable correspondence. In another embodiment, a correspondence threshold of within ±10% of the control sample in 95% of the measurements is acceptable correspondence.

Figure 28:
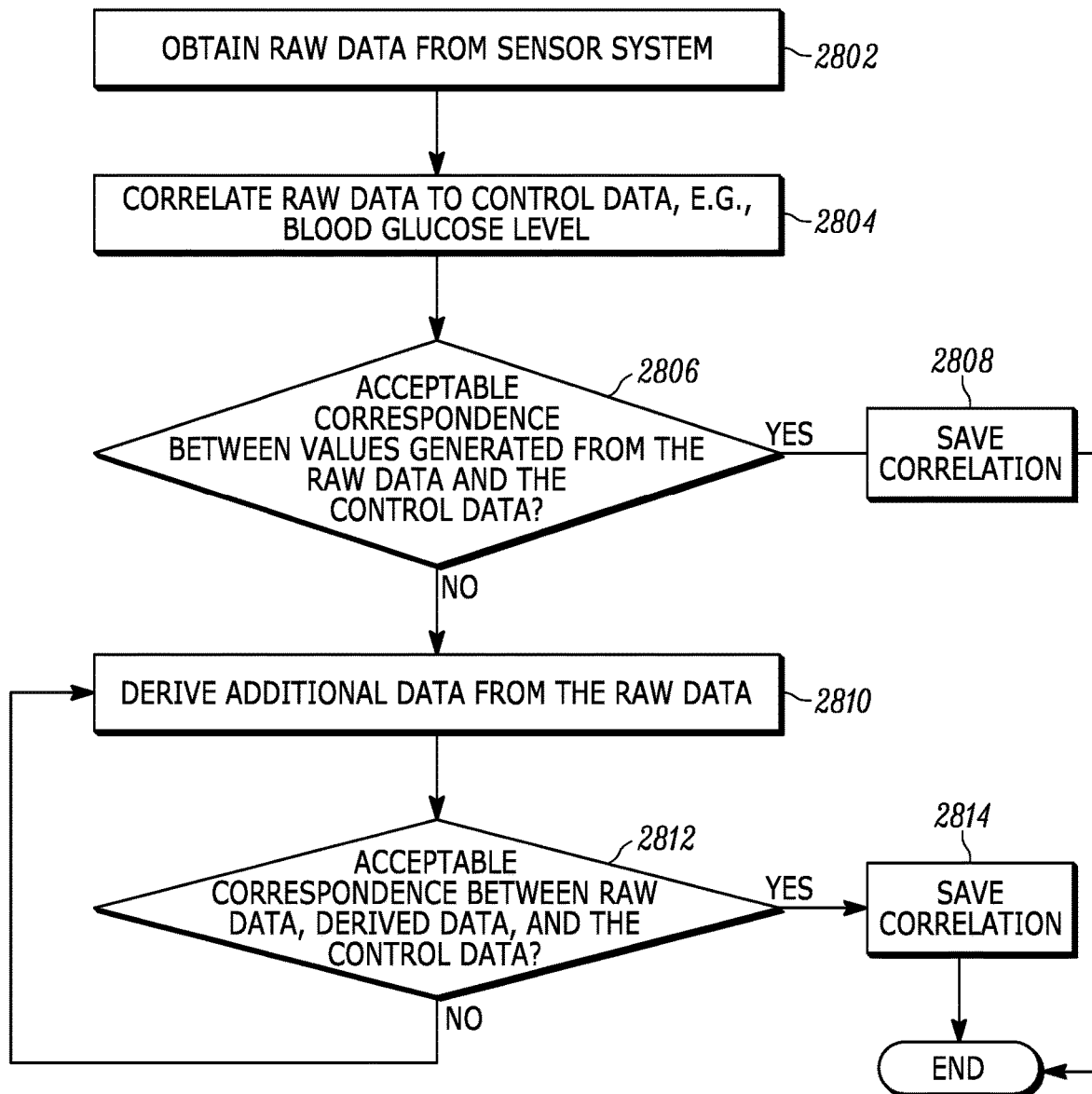
FIG. 28 is an example of a process flow diagram of a method for implementing machine learning.

FIG. 28 is an example of a process flow diagram of a method for implementing machine learning using, for example, the system described above with reference to FIG. 27 to select a correlation (e.g., a model or algorithm) that provides acceptable correspondence between values of a health parameter generated in response to the raw data, the derived data, and actual values of the health parameter in the control samples. At block 2802, raw data is obtained from the sensor system. At block 2804, the raw data is correlated to known control data, such as known blood glucose levels. At decision point 2806, it is determined whether a correlation between the raw data and the control data is acceptable, e.g., whether the correspondence is within an acceptable threshold. If it is determined that there is an acceptable correspondence, then the process proceeds to block 2808, where the correlation (e.g., a model or algorithm) is saved and then the initial learning process is ended. If at decision point 2806 it is determined that there is not an acceptable correspondence between the raw data and the control data (e.g., the correspondence is not within an acceptable threshold), then the process proceeds to block 2810. At block 2810, additional data is derived from the raw data. For example, the machine learning engine may derive a statistic or statistics from the raw data such as a standard deviation, a moving average, and a moving mean. For example, the machine learning engine may derive the standard deviation of the amplitude and/or phase of the received RF energy. At decision point 2812, it is determined whether a correlation between the raw data, the derived data, and the control data is acceptable (e.g., the correspondence is within an acceptable threshold). If it is determined that there is an acceptable correspondence between the raw data, the derived data, and the control data, then the process proceeds to block 2814, where the correlation (e.g., a model or algorithm) is saved and then the initial learning process is ended. If at decision point 2812 it is determined that there is not an acceptable correspondence between the raw data, the derived data, and the control data (e.g., the correspondence is not within an acceptable threshold), then the process returns to block 2810. At block 2810, additional data is derived from the raw data and/or from the derived data. For example, a different statistic, or statistics, is derived from the raw data and/or from the previously derived data. In an embodiment, the exploration of correlations between the raw data, the derived data, and the control data is an iterative process that converges on a correlation, or correlations, which provides acceptable correspondence between the raw data, the derived data, and the control data. In an embodiment, the machine learning process can be repeatedly used to continue to search for correlations that may improve the correspondence between the raw data, the derived data, and the control data to improve the accuracy of health parameter monitoring.

In an embodiment, the above-described process is used for algorithm selection and/or model building as is done in the field of machine learning. In an embodiment, algorithm selection and/or model building involves supervised learning to recognize patterns in the data (e.g., the raw data, the derived data, and/or the control data). In an embodiment, the algorithm selection process may involve utilizing regularized regression algorithms (e.g., Lasso Regression, Ridge Regression, Elastic-Net), decision tree algorithms, and/or tree ensembles (random forests, boosted trees).

In an embodiment, acceptable correlations that are learned by the machine learning engine are trained by the machine learning engine to produce a trained model, or trained models, that can be deployed in the field to monitor a health parameter of a person. Referring back to FIG. 27, a model that is trained by the machine learning engine 2760 is held in the trained model database 2762. In an embodiment, the trained model database may store multiple models that have been found to provide acceptable correspondence between generated values of a health parameter and the actual values of the health parameter as provided in the control data. Additionally, the trained model database 2762 may provide rules on how to apply the model in deployed sensor systems. For example, different models may apply to different deployment conditions, e.g., depending on the location of the RF front-end relative to a blood vessel, environmental conditions, etc.

In an embodiment, operation of the system 2700 shown in FIG. 27 to generate training data and to train a model using the training data involves providing a control sample in the control element 2764 and then operating the sensor system 2700 to implement stepped frequency scanning over a desired frequency range that is within, for example, the 2-6 GHz and/or 122-126 GHz frequency range. For example, control data corresponding to the control sample 2766 is provided to the machine learning engine 2760 and raw data generated from the sensor system 2710 is provided to the machine learning engine. The machine learning engine generates training data by combining the control data with the stepped frequency scanning data in a time synchronous manner. The machine learning engine processes the training data to train a model, or models, which provides an acceptable correspondence between generated values of a health parameter and the control data. The model, or models, is stored in the trained model database 2762, which can then be applied to a system 2700 that is deployed in the field to monitor a health parameter of a person. In an embodiment, the sensor system is exposed to multiple different samples under multiple different operating conditions to generate a rich set of training data.

In an embodiment, the goal of the training process is to produce a trained model that provides a high level of accuracy and reliability in monitoring a health parameter in a person over a wide set of parameter ranges and operational and/or environmental conditions. For example, the correspondence of a model during training can be expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set for a trained model so that the trained model produces correspondence that meets a desired correspondence threshold. In an embodiment, a correspondence threshold of a generated value to the value of a control sample of within ±10% of the control sample is acceptable correspondence for a trained model. In another embodiment, a correspondence threshold of within ±10% of the control sample in 95% of the measurements is acceptable correspondence for a trained model.

In an embodiment, the correspondence between the raw and/or derived data and the control data may change in response to different factors including, for example, over different blood glucose levels, different monitoring locations, different environmental conditions, etc. Thus, in some embodiments, the trained model database 2762 may include multiple different trained models that are applicable to certain conditions. Additionally, the trained model database may evolve over time as more information is gathered and/or as different correlations are discovered.

As described above, the model training process utilizes raw data (e.g., in the form of raw data records) as inputs into the machine learning engine. FIG. 29 is an example of a table of a raw data record (e.g., digital data) generated during stepped frequency scanning that is used to generate the training data. The raw data record includes time t1, a known blood glucose level (e.g., a control sample with a known concentration of glucose in mg/dL, Z mg/dL) at the time t1, TX/RX frequency at the time t1, RX1 amplitude/phase, RX2 amplitude/phase, RX3 amplitude/phase, and RX4 amplitude/phase at the time t1. In the example of FIG. 29, the raw data record includes the glucose level of the control sample at the same time the amplitude and phase of the RF energy was received by the sensor system, thus, the control data is combined with the stepped frequency scanning data in a time synchronous manner. In addition, the raw data records that are used to generate the training data may include some or all of the parameters identified in FIGS. 23 and 24. For example, the raw data records and the corresponding training data may include other variable and/or fixed parameters that correspond to the stepped frequency scanning operation to provide a rich set of parameters from which to generate the training data.

In a stepped frequency scanning operation, multiple raw data records are generated as the sensor system scans across a frequency range. FIGS. 30A-30D are tables of at least portions of raw data records that are generated during a learning process that spans the time of t1-tn, where n corresponds to the number (e.g., an integer of 2 or greater) of time intervals, T, in the stepped frequency scanning. Each of the raw data records includes control data (e.g., known glucose level, Z mg/dL) that is combined with stepped frequency scanning data in a time synchronous manner.

With reference to FIG. 30A, at time, t1, the raw data record includes the time, t1, a known blood glucose level (e.g., Z1 in mg/dL) at time t1, a TX/RX frequency (e.g., X GHz) at time t1, RX1 amplitude/phase at time t1 (ampl1-t1/ph1-t1), RX2 amplitude/phase at time t1 (ampl2-t1/ph2-t1), RX3 amplitude/phase at time t1 (ampl3-t1/ph3-t1), and RX4 amplitude/phase at time t1 (ampl4-t1/ph4-t1). In the stepped frequency scanning, at the next time, t2, the frequency is changed by one step size, e.g., incremented by $\Delta f$. In an embodiment, the stepped frequency scanning operation generates 200 raw data records per second, e.g., a sample rate of 200 samples/second. With reference to FIG. 30B, at time, t2, the raw data record includes the time, t2, a known blood glucose level (e.g., Z2 in mg/dL) at time t2, a TX/RX frequency (e.g., X+$\Delta f$ GHz) at time t2, RX1 amplitude/phase at time t2 (ampl1-t2/ph1-t2), RX2 amplitude/phase at time t2 (ampl2-t2/ph2-t2), RX3 amplitude/phase at time t2 (ampl3-t2/ph3-t2), and RX4 amplitude/phase at time t2 (ampl4-t2/ph4-t2). With reference to FIG. 30C, at time, t3, the raw data record includes the time, t3, a known blood glucose level (e.g., Z3 in mg/dL) at time t3, a TX/RX frequency (e.g., X+2$\Delta f$ GHz) at time t3, RX1 amplitude/phase at time t3 (ampl1-t3/ph1-t3), RX2 amplitude/phase at time t3 (ampl2-t3/ph2-t3), RX3 amplitude/phase at time t3

(ampl3-t3/ph3-t3), and RX4 amplitude/phase at time t3 (ampl4-t3/ph4-t3). With reference to FIG. 30D, at time, tn, the raw data record includes the time, tn, a known blood glucose level (e.g., Zn in mg/dL) at time tn, a TX/RX frequency (e.g., X+(n−1)Δf GHz) at time tn, RX1 amplitude/phase at time tn (ampl1-tn/ph1-tn), RX2 amplitude/phase at time tn (ampl2-tn/ph2-tn), RX3 amplitude/phase at time tn (ampl3-tn/ph3-tn), and RX4 amplitude/phase (ampl4-tn/ph4-tn) at time tn.

As illustrated above, raw data is collected on a per-antenna basis for the amplitude and/or phase of the received RF energy. Raw data collected on a per-antenna basis for amplitude and phase for the example of FIGS. 30A-30D may include:

ampl1: ampl1-t1, ampl1-t2, ampl1-t3, ..., ampl1-tn;
ampl2: ampl2-t1, ampl2-t2, ampl2-t3, ..., ampl2-tn;
ampl3: ampl3-t1, ampl3-t2, ampl3-t3, ..., ampl3-tn;
ampl4: ampl4-t1, ampl4-t2, ampl4-t3, ..., ampl4-tn;
ph1: ph1-t1, ph1-t2, ph1-t3, ..., ph1-tn;
ph2: ph2-t1, ph2-t2, ph2-t3, ..., ph2-tn;
ph3: ph3-t1, ph3-t2, ph3-t3, ..., ph3-tn); and
ph4: ph4-t1, ph4-t2, ph4-t3, ..., ph4-tn).

In the example of FIGS. 30A-30D, the standard deviation may be calculated on a per-antenna basis for the amplitude and phase and is a function of the following raw data elements:

$\sigma(ampl1) = f(ampl1\text{-}t1 + ampl1\text{-}t2 + ampl1\text{-}t3 + \ldots + ampl1\text{-}tn)$;
$\sigma(ampl2) = f(ampl2\text{-}t1 + ampl2\text{-}t2 + ampl2\text{-}t3 + \ldots + ampl2\text{-}tn)$;
$\sigma(ampl3) = f(ampl3\text{-}t1 + ampl3\text{-}t2 + ampl3\text{-}t3 + \ldots + ampl3\text{-}tn)$;
$\sigma(ampl4) = f(ampl4\text{-}t1 + ampl4\text{-}t2 + ampl4\text{-}t3 + \ldots + ampl4\text{-}tn)$;
$\sigma(ph1) = f(ph1\text{-}t1 + ph1\text{-}t2 + ph1\text{-}t3 + \ldots + ph1\text{-}tn)$;
$\sigma(ph2) = f(ph2\text{-}t1 + ph2\text{-}t2 + ph2\text{-}t3 + \ldots + ph2\text{-}tn)$;
$\sigma(ph3) = f(ph3\text{-}t1 + ph3\text{-}t2 + ph3\text{-}t3 + \ldots + ph3\text{-}tn)$; and
$\sigma(ph4) = f(ph4\text{-}t1 + ph4\text{-}t2 + ph4\text{-}t3 + \ldots + ph4\text{-}tn)$.

In an embodiment, data is derived on a per-antenna basis. In other embodiments, data such as statistics can be derived from data corresponding to different combinations of antennas.

Raw data records collected over time can be used as described above to learn correlations (e.g., a model or algorithm) between the raw data, derived data, and the control data and to train a model. In an embodiment, a rich set of training data is collected and processed to train a model that can provide accurate and reliable measurements of a health parameter such as blood glucose level, blood pressure, and/or heart rate. In an embodiment, the raw data including amplitude and phase and the derived data including the standard deviation of the amplitude has been found to correspond well to the health parameter of blood glucose level.

Figure 31:
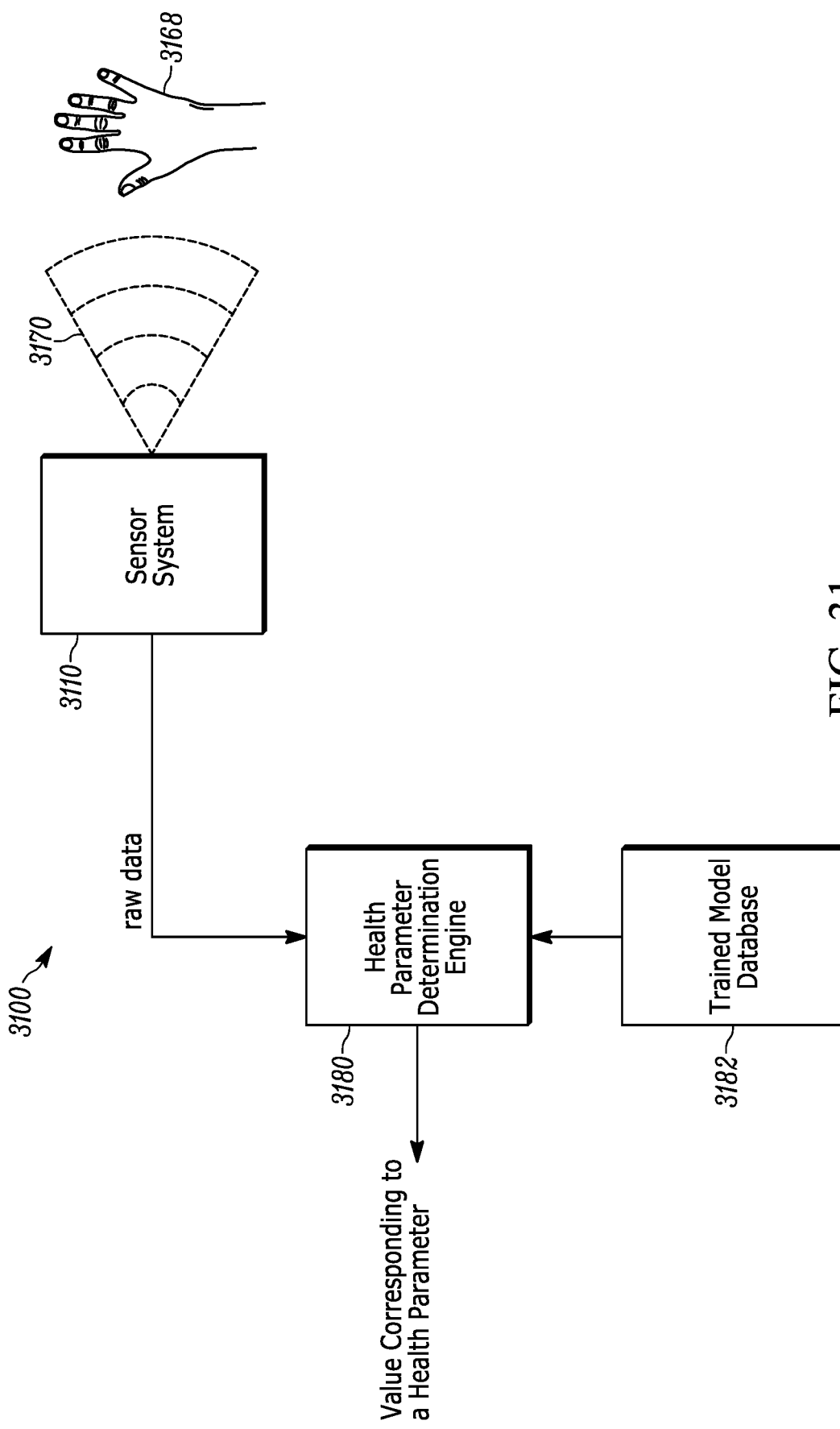
FIG. 31 illustrates a system for health parameter monitoring that utilizes a sensor system similar to or the same as the sensor system described with reference to FIGS. 5-7.

Once correlations between the raw data, the derived data, and the control data have been learned and a model has been trained, a sensor system can be deployed into the field for use in monitoring a health parameter of a person, such as the blood glucose level. FIG. 31 illustrates a system 3100 for health parameter monitoring that utilizes a sensor system similar to or the same as the sensor system described above. With reference to FIG. 31, the system includes a sensor system 3110, a health parameter determination engine 3180, and a trained model database 3182.

In an embodiment, the sensor system 3110 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the health parameter determination engine 3180 that can be accumulated and used to generate and output a value that corresponds to a health parameter.

A model (or models) that is trained by the machine learning engine as described above is held in the trained model database 3182. In an embodiment, the trained model database may store multiple models that have been trained to provide acceptable correspondence between a generated value of a health parameter and the actual value of the health parameter as provided in the control data. Additionally, the trained model database may provide rules on how to apply trained models in deployed sensor systems. In an embodiment, the trained model database includes memory for storing a trained model, or models. The memory may include, for example, RAM, SRAM, and/or SSD.

In an embodiment, the health parameter determination engine 3180 is configured to generate an output that corresponds to a health parameter in response to the raw data received from the sensor system 3110, derived data, and using a trained model that is stored in the trained model database 3182. For example, the health parameter determination engine 3180 outputs a value that indicates a blood glucose level in mg/dL or some other indication of the blood glucose level. In other embodiments, the health parameter determination engine may output a value that is an indication of a person's heart rate (e.g., in beats per minute) and/or an indication of a person's blood pressure (e.g., in millimeters of mercury, mmHg). In other embodiments, the "values" output by the health parameter determination engine may correspond to a health parameter in other ways. For example, the output value may indicate a value such as "high," "medium," "low" with respect to a health parameter (e.g., a high blood glucose level, a medium blood glucose level, or a low blood glucose level relative to a blood glucose scale), the output value may indicate a color, such as green, yellow, or red that indicates a health parameter, or the output value, may indicate a range of values, such as 130-140 mg/dL blood glucose, 70-80 beats per minute, or 110-120 mmHg blood pressure. In an embodiment, the health parameter determination engine recognizes patterns in the raw and/or derived data and applies the recognized patterns to the trained model to generate an output that corresponds to a health parameter in a person. The health parameter determination engine may be implemented by a digital processor, such as a CPU or MCU, in conjunction with computer readable instructions that executed by the digital processor.

In an embodiment, operation of the system 3100 shown in FIG. 31 involves bringing a portion of a person's anatomy 3186 (such as a wrist, arm, or ear area) into close proximity to the sensor system 3110 (or bringing the sensor system into close proximity to the portion of a person's anatomy) and operating the sensor system to implement stepped frequency scanning over a frequency range, e.g., in the range of 122-126 GHz such that transmitted RF energy 3170 penetrates below the surface of the person's skin. Raw data generated from implementing the stepped frequency scanning is output from the sensor system and received at the health parameter determination engine 3180. The health parameter determination engine processes the raw data in conjunction with at least one trained model from the trained model database 3182 to generate a value that corresponds to a health parameter of the person, e.g., a value that corresponds to the blood glucose level of the person. In an embodiment, the value that corresponds to the health parameter is output, for example, as a graphical indication of the blood glucose level. In an embodiment, the generated value may be stored in a health parameter database for subsequent access.

In an embodiment, the system 3100 depicted in FIG. 31 is implemented in a device such as a smartwatch or smartphone. In other embodiments, some portion of the system (e.g., the RF front-end) is implemented in a device, such as a dongle, a patch, a smartphone case, or some other device and the health parameter determination engine and the trained model correlations database is implemented in a nearby device such as a smartphone. For example, in one embodiment, the sensor system is embodied in a device that attaches near the ear of a person and raw data is communicated via a wireless connection to a device such as a smartphone that processes the raw data to generate a value that corresponds to the blood glucose level of the person.

Figure 32:
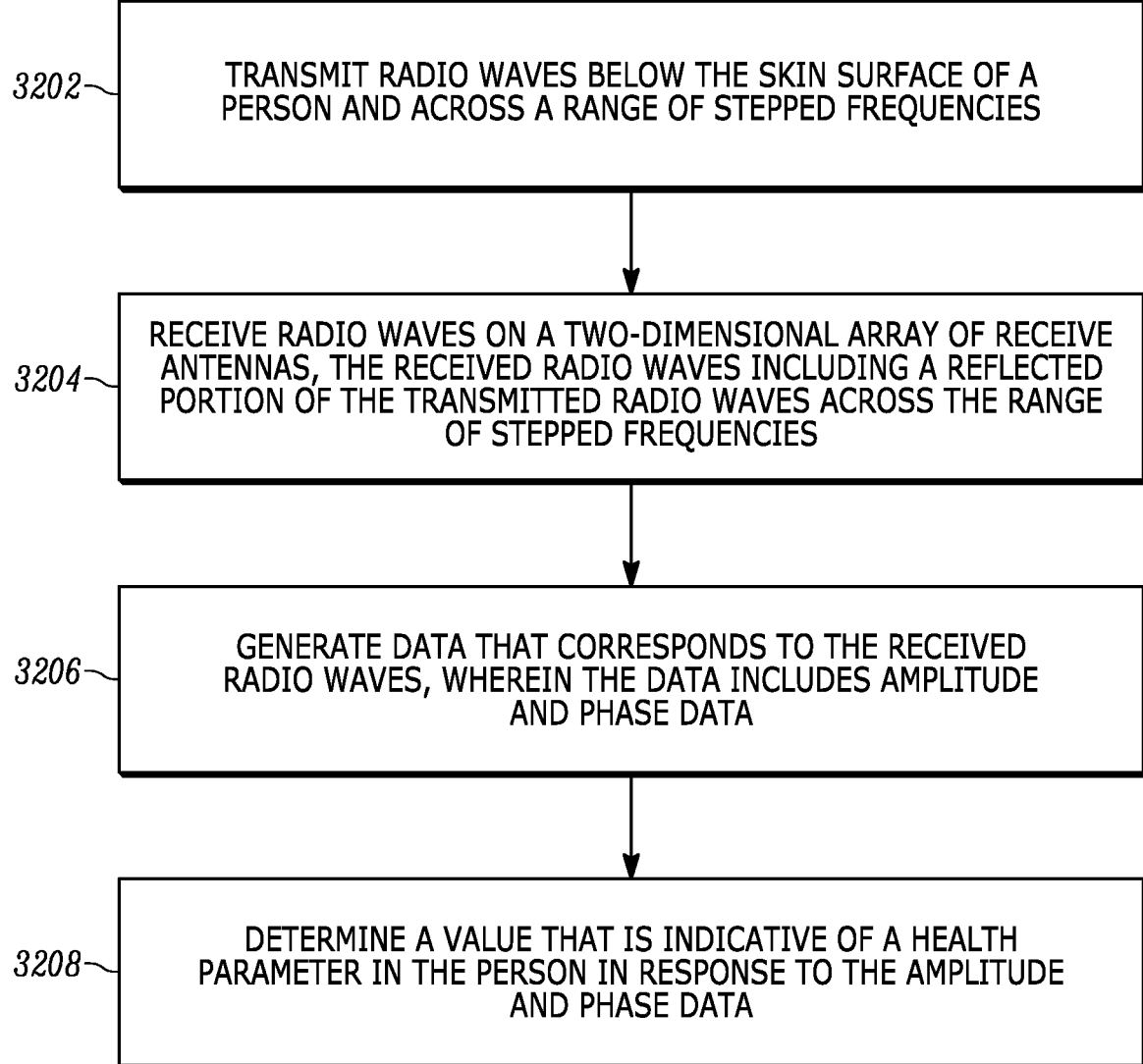
FIG. 32 is a process flow diagram of a method for monitoring a health parameter in a person.

FIG. 32 is a process flow diagram of a method for monitoring a health parameter in a person. At block 3202, radio waves are transmitted below the skin surface of a person and across a range of stepped frequencies. At block 3204, radio waves are received on a two-dimensional array of receive antennas, the received radio waves including a reflected portion of the transmitted radio waves across the range of stepped frequencies. At block 3206, data that corresponds to the received radio waves is generated, wherein the data includes amplitude and phase data. At block 3208, a value that is indicative of a health parameter in the person is determined in response to the amplitude and phase data.

Figure 33:
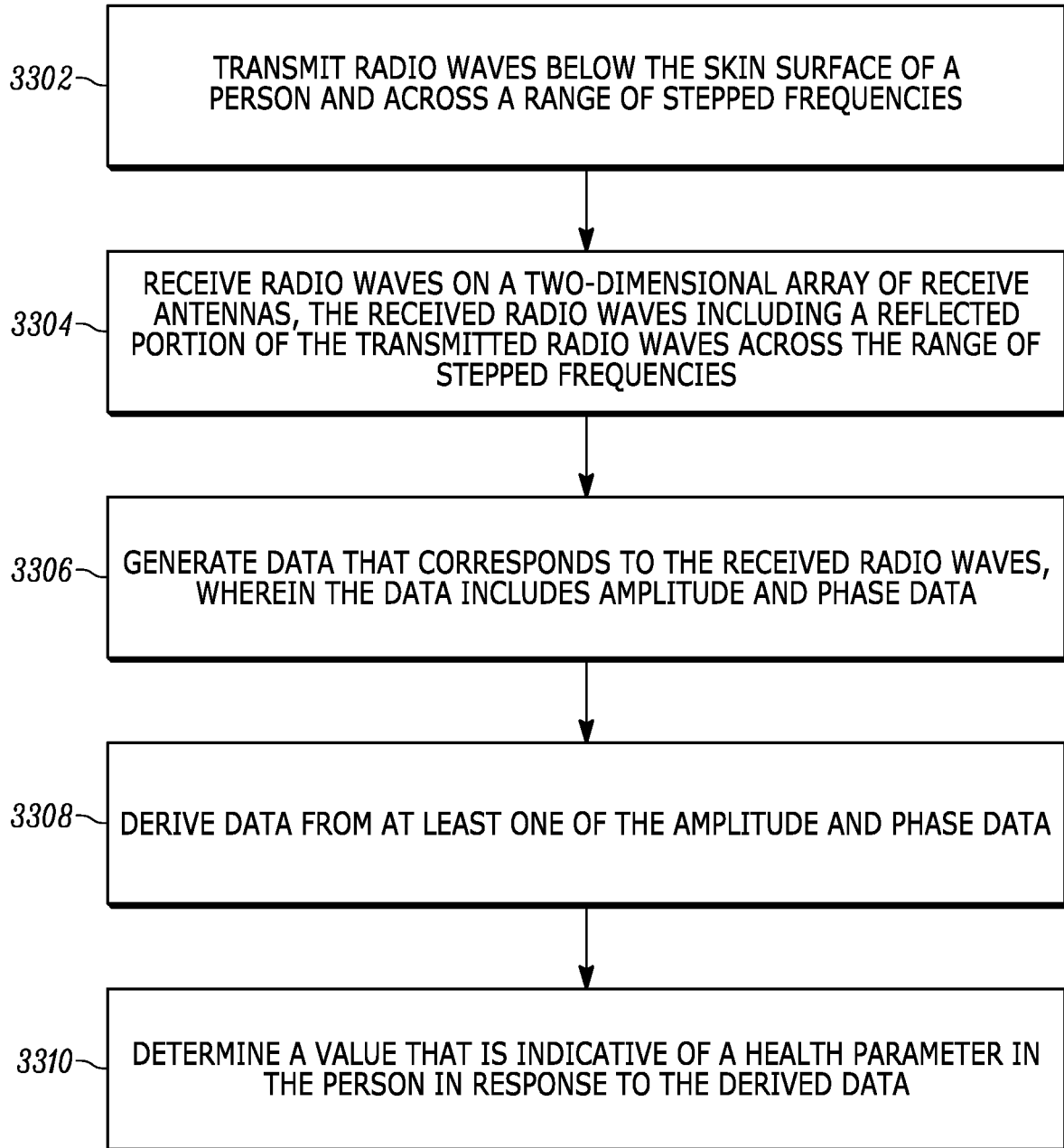
FIG. 33 is a process flow diagram of another method for monitoring a health parameter in a person.

FIG. 33 is a process flow diagram of another method for monitoring a health parameter in a person. At block 3302, radio waves are transmitted below the skin surface of a person and across a range of stepped frequencies. At block 3304, radio waves are received on a two-dimensional array of receive antennas, the received radio waves including a reflected portion of the transmitted radio waves across the range of stepped frequencies. At block 3306, data that corresponds to the received radio waves is generated, wherein the data includes amplitude and phase data. At block 3308, data is derived from at least one of the amplitude and phase data. At block 3310, a value that is indicative of a health parameter in the person is determined in response to the derived data.

Figure 34:
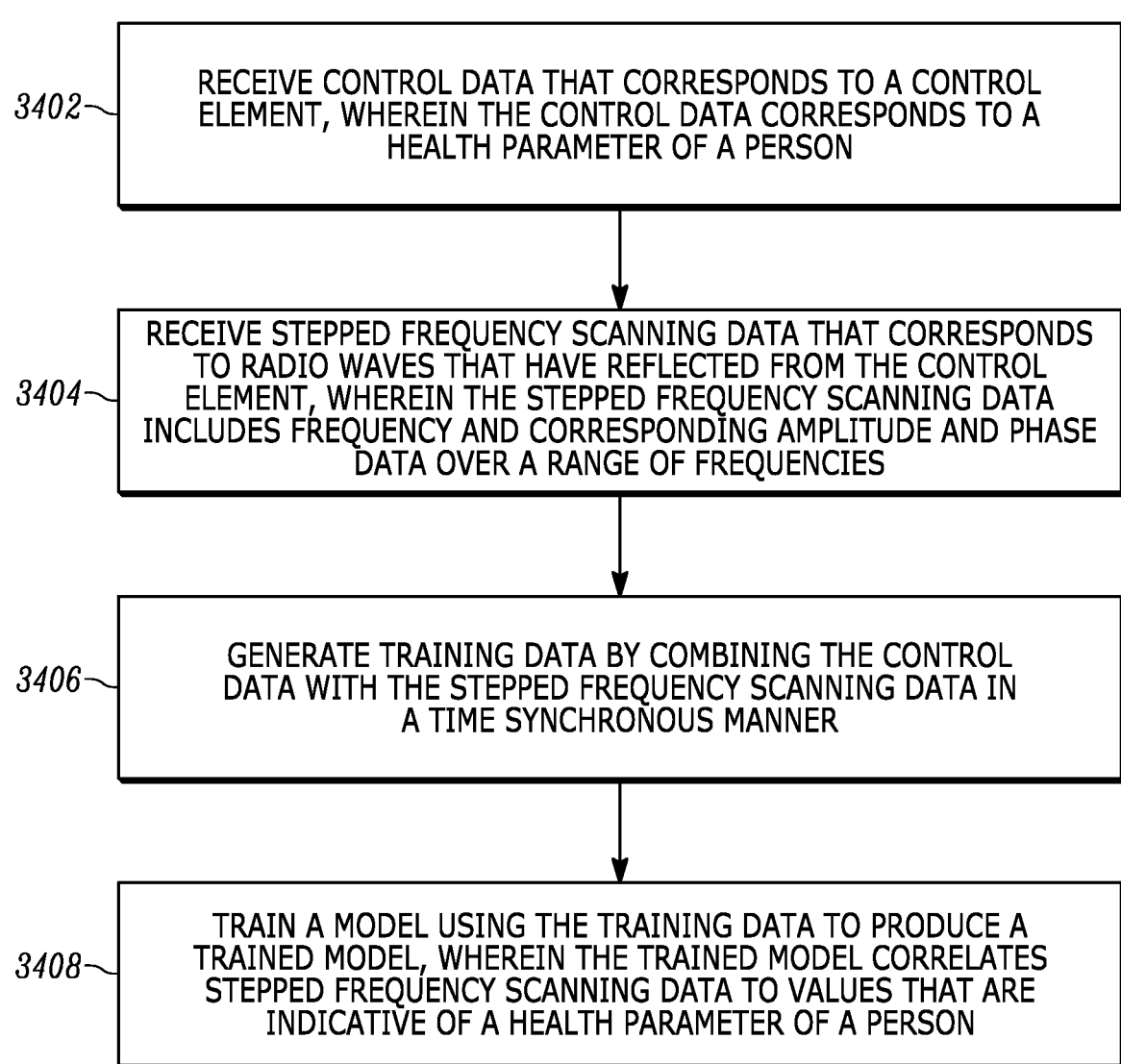
FIG. 34 is a process flow diagram of a method for training a model for use in monitoring a health parameter in a person.

FIG. 34 is a process flow diagram of a method for training a model for use in monitoring a health parameter in a person. At block 3402, control data that corresponds to a control element is received, wherein the control data corresponds to a health parameter of a person. At block 3404, stepped frequency scanning data that corresponds to radio waves that have reflected from the control element is received, wherein the stepped frequency scanning data includes frequency and corresponding amplitude and phase data over a range of frequencies. At block 3406, training data is generated by combining the control data with the stepped frequency scanning data in a time synchronous manner. At block 3408, a model is trained using the training data to produce a trained model, wherein the trained model correlates stepped frequency scanning data to values that are indicative of a health parameter of a person.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Alternatively, embodiments of the invention may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for monitoring a blood pressure level in a person, the method comprising:
   transmitting, from at least one transmit antenna of a wearable health monitoring device, millimeter range radio waves over a three-dimensional (3D) space below a skin surface of the person, wherein the millimeter range radio waves are transmitted in a stepped frequency pattern across a range of frequencies;
   receiving radio waves on multiple receive antennas of the wearable health monitoring device, the received radio waves including a reflected portion of the transmitted radio waves that is reflected by blood in a blood vessel in the 3D space;
   isolating a signal that corresponds to the portion of the transmitted radio waves that is reflected by the blood in the blood vessel in response to receiving the radio waves on the multiple receive antennas, wherein isolating the signal that corresponds to the portion of the transmitted radio waves that is reflected by the blood in the blood vessel involves implementing range discrimination in a digital signal processor (DSP) of the wearable health monitoring device to isolate electrical signals, which correspond to radio waves that are received on the multiple receive antennas directly from the at least one transmit antenna without first passing through the skin of the person, from the signal that corresponds to the portion of the transmitted radio waves that is reflected by the blood in the blood vessel; and
   outputting a signal from the wearable health monitoring device that corresponds to the blood pressure level in the person in response to the isolated signal, wherein the isolated signal represents a change in reflectivity of the blood in the blood vessel and wherein the change in reflectivity of the blood in the blood vessel is correlated to a change in the blood pressure level in the person.

2. The method of claim 1, wherein the range of frequencies is 122-126 GHz.

3. The method of claim 1, wherein isolating the signal that corresponds to the portion of the transmitted radio waves that is reflected by the blood in the blood vessel in response to receiving the radio waves on the multiple receive antennas comprises implementing beamforming signal processing to isolate the signal that corresponds to the radio waves reflected from the blood in the blood vessel.

4. The method of claim 1, wherein isolating the signal that corresponds to the portion of the transmitted radio waves that is reflected by the blood in the blood vessel in response to receiving the radio waves on the multiple receive antennas comprises using beamforming to focus a receive beam on the blood vessel.

5. The method of claim 1, wherein the transmitting, receiving, isolating, and outputting occurs in the wearable health monitoring device, which is attached to the person.

6. The method of claim 1, wherein the millimeter range radio waves are transmitted from the at least one transmit antenna configured for radio waves in a frequency range of 122-126 GHz and the received radio waves are received on the multiple receive antennas that are configured for the radio waves in the frequency range of 122-126 GHz, wherein the at least one transmit antenna and the multiple receive antennas are microstrip patch antennas having dimensions of no more than 1.3 mm×1.3 mm.

7. The method of claim 1, wherein transmitting the millimeter range radio waves over the 3D space below the skin surface of the person comprises first transmitting from a first transmit antenna and then subsequently transmitting from a second transmit antenna such that the first transmission does not overlap in time with the subsequent transmission.

8. The method of claim 1, wherein the stepped frequency pattern comprises a fixed increment at each step, and wherein the frequency range is 122-126 GHz and wherein the fixed increment ranges from 15.625 MHz to 62.5 MHz.

9. The method of claim 1, wherein isolating the signal that corresponds to the portion of the transmitted radio waves that is reflected by the blood in the blood vessel in response to receiving the radio waves on the multiple receive antennas comprises using Doppler effect processing, including fast Fourier transform (FFT) processing, to isolate signals that correspond to relative movement.

10. The method of claim 1, wherein isolating the signal that corresponds to the portion of the transmitted radio waves that is reflected by the blood in the blood vessel in response to receiving the radio waves on the multiple receive antennas comprises digitally combining the received signals from the multiple receive antennas.

11. The method of claim 1, wherein the millimeter range radio waves are transmitted from two transmit antennas and received at four receive antennas, wherein the two transmit antennas and the four receive antennas are microstrip patch antennas having dimensions of no more than 1.3 mm×1.3 mm.

12. The method of claim 1, wherein the millimeter range radio waves are transmitted at an initial power such that the initial power is diminished by at least one-half at a penetration depth below the skin surface of 6 mm or less.

13. The method of claim 1, further comprising outputting a signal that corresponds to a heart rate in the person in response to the isolated signal.

14. The method of claim 1, wherein implementing the range discrimination involves placing signals in range bins such that there is one complex sample per range bin per frequency across the range of frequencies.

15. A wearable health monitoring device for monitoring a blood pressure level in a person, the device comprising:
   a frequency synthesizer configured to generate millimeter range radio waves in a stepped frequency pattern over a range of frequencies;
   at least one transmit antenna configured to transmit the millimeter range radio waves over a three-dimensional (3D) space below a skin surface of the person;
   multiple receive antennas configured to receive radio waves, the received radio waves including a reflected portion of the transmitted radio waves that is reflected by blood in a blood vessel in the 3D space; and
   means for isolating a signal that corresponds to the portion of the transmitted radio waves that is reflected by the blood in the blood vessel in response to receiving the radio waves on the multiple receive antennas and outputting a signal that corresponds to the blood pressure level of the person in response to the isolated signal, wherein isolating the signal that corresponds to the portion of the transmitted radio waves that is reflected by the blood in the blood vessel involves implementing range discrimination to isolate electrical signals, which correspond to radio waves that are received on the multiple receive antennas directly from the at least one transmit antenna without first passing through the skin of the person, from the signal that corresponds to the portion of the transmitted radio waves that is reflected by the blood in the vessel, and wherein the isolated signal represents a change in reflectivity of the blood in the blood vessel and wherein the change in reflectivity of the blood in the blood vessel is correlated to a change in the blood pressure level in the person.

16. The wearable health monitoring device of claim 15, wherein the at least one transmit antenna and the multiple receive antennas are configured for radio waves in a frequency range of 122-126 GHz, and wherein the at least one transmit antenna and the multiple receive antennas are microstrip patch antennas having dimensions of no more than 1.3 mm×1.3 mm.

17. The wearable health monitoring device of claim 15, further comprising a semiconductor substrate with at least one transmit component and multiple receive components, wherein the at least one transmit component and the at least one transmit antenna comprise at least two transmit components and at least two transmit antennas and wherein the multiple receive components and the multiple receive antennas comprises four receive components and four receive antennas.

18. The wearable health monitoring device of claim 17, wherein the at least two transmit antennas are configured to transmit radio waves at two different polarization orientations and wherein a first set of the at least four receive antennas is configured to receive radio waves at one of the at least two different polarization orientations and a second set of the at least four receive antennas is configured to receive radio waves at a different one of the at least two different polarization orientations.

19. The wearable health monitoring device of claim 15, wherein implementing the range discrimination involves placing signals in range bins such that there is one complex sample per range bin per frequency across the range of frequencies.

* * * * *